(12) United States Patent
Graham et al.

(10) Patent No.: US 10,934,312 B2
(45) Date of Patent: Mar. 2, 2021

(54) TRICYCLIC HETEROCYCLE COMPOUNDS USEFUL AS HIV INTEGRASE INHIBITORS

(71) Applicant: Merck Sharp & Dohme Corp., Rahway, NJ (US)

(72) Inventors: Thomas H. Graham, Quincy, MA (US); Tao Yu, Edison, NJ (US); Sherman T. Waddell, Westfield, NJ (US); John A. McCauley, Maple Glen, PA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/465,614

(22) PCT Filed: Dec. 1, 2017

(86) PCT No.: PCT/US2017/064116
§ 371 (c)(1),
(2) Date: May 31, 2019

(87) PCT Pub. No.: WO2018/102634
PCT Pub. Date: Jun. 7, 2018

(65) Prior Publication Data
US 2020/0017524 A1 Jan. 16, 2020

Related U.S. Application Data

(60) Provisional application No. 62/429,376, filed on Dec. 2, 2016.

(51) Int. Cl.
| | |
|---|---|
| *A61K 31/53* | (2006.01) |
| *A61P 31/18* | (2006.01) |
| *C07D 471/16* | (2006.01) |
| *C07D 498/16* | (2006.01) |
| *C07D 491/22* | (2006.01) |
| *A61K 45/06* | (2006.01) |

(52) U.S. Cl.
CPC ............ *C07D 498/16* (2013.01); *A61P 31/18* (2018.01); *C07D 471/16* (2013.01); *C07D 491/22* (2013.01); *A61K 45/06* (2013.01)

(58) Field of Classification Search
CPC ........ A61K 31/53; A61P 31/18; C07D 487/16
See application file for complete search history.

(56) References Cited

U.S. PATENT DOCUMENTS

| | | |
|---|---|---|
| 9,643,982 B2 | 5/2017 | Coleman et al. |
| 2012/0208998 A1 | 8/2012 | Yoshida et al. |
| 2015/0329539 A1 | 11/2015 | Embrey et al. |
| 2016/0060272 A1 | 3/2016 | Graham et al. |
| 2018/0099967 A1 | 4/2018 | Yu |

FOREIGN PATENT DOCUMENTS

| | | |
|---|---|---|
| WO | 2014183532 A1 | 11/2014 |
| WO | 2014200880 A1 | 12/2014 |
| WO | 2015174511 A1 | 11/2015 |
| WO | 2016191239 A1 | 12/2016 |

OTHER PUBLICATIONS

International Search Report and Written Opinion for PCT/US2017/064116, dated Feb. 26, 2018, 8 pages.
Kawasuji, T.; et al., Carbamoyl Pyridone HIV-1 Integrase Inhibitors. 2. Bi- and Tricyclic Derivatives Result in Superior Antiviral and Pharmacokinetic Profiles, Journal of Medicinal Chemistry, 2013, pp. 1124-1135., vol. 56, No. 3.
Supplementary European Search Report for 17876015.3 dated May 6, 2020; 6 pages.

*Primary Examiner* — Brenda L Coleman
(74) *Attorney, Agent, or Firm* — Nicole M. Beeler; John C. Todaro

(57) ABSTRACT

The present invention relates to Tricyclic Heterocycle Compounds of Formula (I): and pharmaceutically acceptable salts or prodrug thereof, wherein A, X, Y, Z, $R^1$, $R^{7A}$, $R^{7B}$ and $R^8$ are as defined herein. The present invention also relates to compositions comprising at least one Tricyclic Heterocycle Compound, and methods of using the Tricyclic Heterocycle Compounds for treating or preventing HIV infection in a subject.

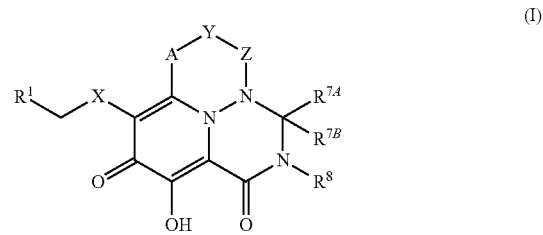

17 Claims, No Drawings

TRICYCLIC HETEROCYCLE COMPOUNDS USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2017/064116 filed Dec. 1, 2017, which claims priority from U.S. Ser. No. 62/429,376 filed Dec. 2, 2016.

FIELD OF THE INVENTION

The present invention relates to Tricyclic Heterocycle Compounds, compositions comprising at least one Tricyclic Heterocycle Compound, and methods of using the Tricyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references may be of interest as background:

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that may be useful as HIV integrase inhibitors.

U.S. Pat. Nos. 7,135,467 and 7,037,908 disclose certain pyrimidine carboxamides that may be useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that may be useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that may be useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that may be useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

U.S. Pat. Nos. 7,462,608 and 7,649,015 each disclose phosphate and phosphonate substituted heterocycles useful as HIV nNRTI inhibitors and HIV protease inhibitors, respectively.

SUMMARY OF THE INVENTION

In one aspect, the present invention provides Compounds of Formula (I):

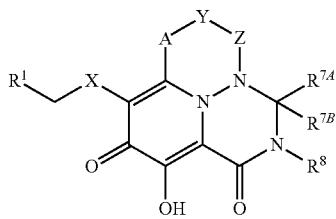

(I)

or a pharmaceutically acceptable salt thereof,
wherein:
A is —C($R^2$)—;
X is 5 or 6-membered monocyclic heteroaryl or —N($R^5$)C(O)—;
Y is selected from —O—, —N($R^5$)— or —CH($R^3$)—, or -A-Y— is —C($R^2$)═CH—;
Z is —C(O)—, —CH($R^4$)— or a bond, such that: (i) when Y is —O— or —N($R^5$)—, then Z is a bond, (b) when Y is —CH($R^3$)—, then Z is a bond or —CH($R^4$)—, and (iii) when -A-Y— is —C($R^2$)═CH—, then Z is a bond;
$R^1$ is a phenyl group which is optionally substituted with from 1 to 3 groups, each independently selected from $C_1$-$C_6$ alkyl, halo, —O—($C_1$-$C_6$ alkyl), $C_1$-$C_6$ haloalkyl, —O—($C_1$-$C_6$ haloalkyl), —CN, —$NO_2$, —N($R^4$)$_2$, —C(O)O$R^6$, —C(O)N($R^4$)$_2$ and —NHC(O)$R^6$;
$R^2$ is selected from H, $C_1$-$C_6$ alkyl, —O—($C_1$-$C_6$ alkyl) and —N($R^4$)$_2$;
$R^3$ is selected from H, $C_1$-$C_6$ alkyl and —O—($C_1$-$C_6$ alkyl);
each occurrence of $R^4$ is independently selected from H, $C_1$-$C_6$ alkyl and —O—($C_1$-$C_6$ alkyl);
each occurrence of $R^5$ is independently H or $C_1$-$C_6$ alkyl;
each occurrence of $R^6$ is independently selected from H, $C_1$-$C_6$ alkyl and $C_3$-$C_7$ cycloalkyl;
$R^{7A}$ is H;
$R^{7B}$ is H, or $R^{7A}$ and $R^{7B}$, together with the common carbon atom to which they are each attached, join to form a spirocyclic $C_3$-$C_7$ cycloalkyl group or a spirocyclic 4- to 7-membered monocyclic heterocycloalkyl group; and
$R^8$ is selected from $C_1$-$C_6$ alkyl, —($C_1$-$C_6$ alkylene)-O—($C_1$-$C_6$ alkyl), $C_3$-$C_7$ cycloalkyl and —($C_1$-$C_6$ alkylene)-$C_3$-$C_7$ cycloalkyl.

The Compounds of Formula (I) (also referred to herein as the "Tricyclic Heterocycle Compounds") and pharmaceutically acceptable salts or prodrugs thereof may be useful, for example, for inhibiting HIV viral replication or replicon activity, or for treating or preventing HIV infection in a subject. Without being bound by any specific theory, it is believed that the Tricyclic Heterocycle Compounds inhibit HIV viral replication by inhibiting HIV Integrase.

Accordingly, the present invention provides methods for treating or preventing HIV infection in a subject, comprising administering to the subject an effective amount of at least one Tricyclic Heterocycle Compound.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Tricyclic Heterocycle Compounds, compositions comprising at least one Tricyclic Heterocycle Compound, and methods of using the Tricyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tricyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)—alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_1$-C$_3$ alkylene" refers to an alkylene group having from 1 to 3 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group is optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group is optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

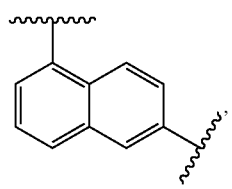 [SMILES: *c1ccc2c(*)cccc2c1]

is understood to represent both:

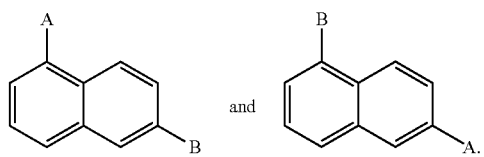

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

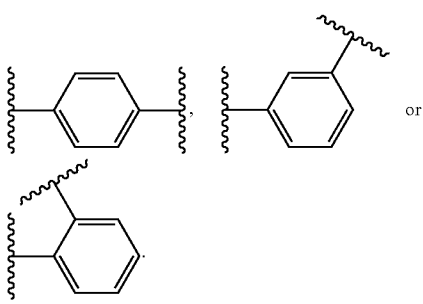

Unless otherwise indicated, an arylene group is unsubstituted.

The term "cycloalkyl," as used herein, refers to a non-aromatic mono- or multicyclic saturated ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group is optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

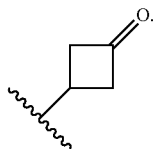 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. A heteroaryl group is optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group is optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

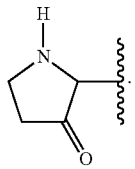

In one embodiment, a heterocycloalkyl group is a 5-membered monocyclic heterocycloalkyl. In another embodiment, a heterocycloalkyl group is a 6-membered monocyclic heterocycloalkyl. The term "4 to 7-membered monocyclic heterocycloalkyl" refers to a monocyclic heterocycloalkyl group having from 4 to 7 ring atoms. The term "5 to 8-membered monocyclic heterocycloalkyl" refers to a monocyclic heterocycloalkyl group having from 5 to 8 ring atoms. The term "8 to 11-membered bicyclic heterocycloalkyl" refers to a bicyclic heterocycloalkyl group having from 8 to 11 ring atoms. Unless otherwise indicated, a heterocycloalkyl group is unsubstituted.

The term "heterocycloalkenyl," as used herein, refers to an heterocycloalkyl group, as defined above, which is non-aromatic and contains at least one endocyclic double bond between two adjacent ring atoms. A heterocycloalkenyl group can be joined via a ring carbon, ring silicon atom or ring nitrogen atom. In one embodiment, a heterocycloalkenyl group is monocyclic and has from about 3 to about 7 ring atoms. In another embodiment, a heterocycloalkenyl group is monocyclic has from about 5 to about 8 ring atoms. In another embodiment, a heterocycloalkenyl group is bicyclic and has from about 8 to about 11 ring atoms. In still another embodiment, a heterocycloalkenyl group is monocyclic and has 5 or 6 ring atoms. In one embodiment, a heterocycloalkenyl group is monocyclic. In another embodiment, a heterocycloalkenyl group is bicyclic. There are no adjacent oxygen and/or sulfur atoms present in the ring system. Any —NH group in a heterocycloalkenyl ring may be substituted or may exist protected such as, for example, as an —N(BOC), —N(Cbz), —N(Tos) group and the like; such protected heterocycloalkenyl groups are considered part of this invention. The term "heterocycloalkenyl" also encompasses a heterocycloalkenyl group, as defined above, which is fused to an aryl (e.g., benzene) or heteroaryl ring. A heterocycloalkenyl group is optionally substituted by one or more "ring system substituents" which may be the same or different, and are as defined herein below. The nitrogen or sulfur atom of the heterocycloalkenyl can be optionally oxidized to the corresponding N-oxide, S-oxide or S,S-dioxide.

A ring carbon atom of a heterocycloalkenyl group may be functionalized as a carbonyl group. An illustrative example of such a heterocycloalkenyl group is:

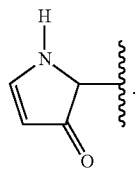 [SMILES: *C1NC=CC1=O]

In one embodiment, a heterocycloalkenyl group is a 5-membered monocyclic heterocycloalkenyl. In another embodiment, a heterocycloalkenyl group is a 6-membered monocyclic heterocycloalkenyl. The term "4 to 7-membered monocyclic heterocycloalkenyl" refers to a monocyclic heterocycloalkenyl group having from 4 to 7 ring atoms. The term "5 to 8-membered monocyclic heterocycloalkenyl" refers to a monocyclic heterocycloalkenyl group having from 5 to 8 ring atoms. The term "8 to 11-membered bicyclic heterocycloalkenyl" refers to a bicyclic heterocycloalkenyl group having from 8 to 11 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O—alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$) (Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

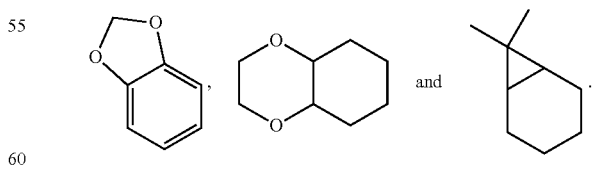

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$ and $R^5$) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tricyclic Heterocycle Compound or a pharmaceutically acceptable salt of the compound. The transformation may occur by various mechanisms (e.g., by metabolic or chemical processes), such as, for example, through hydrolysis in blood. For example, if a Tricyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl, and the like.

Similarly, if a Tricyclic Heterocycle Compound contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Tricyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C($Y^4$) $Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tricyclic Heterocycle Compounds can form salts which are also within the scope of this invention. Reference to a Tricyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tricyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tricyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tricyclic Heterocycle Compounds may be atropisomers (e.g., substituted biaryls) and are considered as part of this invention. Enantiomers can also be directly separated using chiral chromatographic techniques.

It is also possible that the Tricyclic Heterocycle Compounds may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tricyclic Heterocycle Compound incorporates a double bond or a fused ring, both the cis- and trans-forms, as well as mixtures, are embraced within the scope of the invention.

When a subsituent on a chiral carbon atom is depicted as a racemate (by using a straight line bond to a chiral center), it it to be understood that both the alpha and beta configurations of said subtituent group are to be considered part of the present invention. For example, the compound of the present invention, which is drawn as follows:

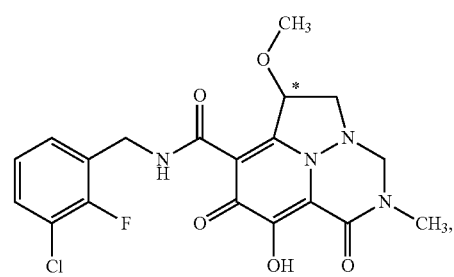 [SMILES: COC1CN2CN(C)C(=O)c3c(O)c(=O)c(C(=O)NCc4cccc(Cl)c4F)c1n32]

is understood to encompass both stereoisomers at the indicated chiral center, the structures of which are as follows:

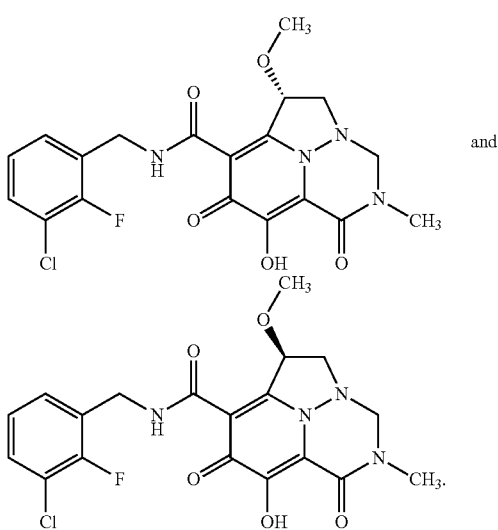

In the Examples section below, compounds of the present invention that have been purified as individual stereoisomers are sometimes depicted in racemic form but identified using one or more of the terms: "diastereomer 1," "diastereomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Tricyclic Heterocycle Compounds may be useful in human and veterinary medicine for treating or preventing HIV infection in a subject. In one embodiment, the Tricyclic Heterocycle Compounds can be inhibitors of HIV viral replication. In a specific embodiment, the Tricyclic Heterocycle Compounds are inhibitors of HIV-1. Accordingly, the Tricyclic Heterocycle Compounds may be useful for treating HIV infections and AIDS. In accordance with the invention, the Tricyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Tricyclic Heterocycle Compound or a pharmaceutically acceptable salt thereof. In a specific embodiment, the present invention provides methods for treating AIDS in a subject comprising administering to the subject an effective amount of at least one Tricyclic Heterocycle Compound or a pharmaceutically acceptable salt thereof.

List of Abbreviations

Ac=acetyl
ACN=acetonitrile
AcOH=acetic acid
Bn=benzyl
Boc=t-butyloxycarbonyl
Boc$_2$O=t-butyloxycarbonyl anhydride
CDI=N,N'-carbonyl diimidazole
DAST=(diethylamino)sulfurtrifluoride
Dess-Martin reagent=1,1,1-Triacetoxy-1,1-dihydro-1,2-benziodoxol-3(1H)-one
DIPEA=N,N-diisopropylethylamine
DMB=2,4-dimethoxybenzyl
DMF=dimethylformamide
DMSO=dimethyl sulfoxide
Et=ethyl
EtOAc=ethyl acetate
hour(s)
HATU=1-[bis(dimethylamino)methylene]-1H-1,2,3-triazolo[4,5-b]pyridinium 3-oxid hexafluorophosphate
HCl=hydrochloric acid
HOAT=1-hydroxy-7-azabenzotriazole
HPLC=high-pressure liquid chromatography
KHMDS=potassium hexamethyldisilazane
LCMS=liquid chromatography-mass spectrometry
IPA=isopropanol
LiHMDS=lithium hexamethyldisilazane
m-CPBA=meta-chloroperoxybenzoic acid
MeOH=methanol
MS=mass spectroscopy
Me=methyl
MeI=iodomethane
min=minute(s)
MSCl=methanesulfonyl chloride
NBS=N-bromosuccinimide
NIS=N-iodosuccinimide
NHS=normal human serum
NMO=N-methylmorpholine-N-oxide
NMR=nuclear magnetic resonance spectroscopy
Pd/C=palladium on carbon
Pd(OAc)$_2$=palladium(II)acetate
Ph=phenyl
pySO$_3$=sulfur trioxide-pyridine complex
Pd(PPh$_3$)$_4$=tetrakis (triphenylphoshpine) palladium(0)
RP-HPLC=reverse-phase high-pressure liquid chromatography
rt=room temperature
SFC=supercritical fluid chromatography
TBAF=tetra-n-butylammonium fluoride TEMPO=2,2,6,6-tetramethylpiperidine-N-oxide
TFA=trifluoroacetic acid
THF=tetrahydrofuran
THP=tetrahydropyranyl
TLC=thin-layer chromatography The Compounds of Formula (I)

The present invention provides Tricyclic Heterocycle Compounds of Formula (I):

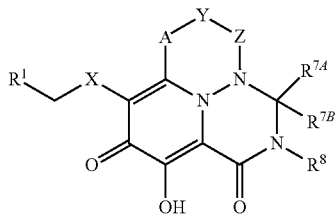
(I)

and pharmaceutically acceptable salts thereof, wherein A, X, Y, Z, $R^1$, $R^{7A}$, $R^{7B}$ and $R^8$ are defined above for the Compounds of Formula (I).

In one embodiment, the present invention provides compounds of formula (I):

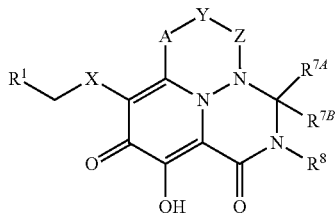
(I)

or a pharmaceutically acceptable salt thereof,
wherein:
the group -A-Y—Z— is selected from is —CH($R^2$)—, —CH$_2$—N($R^5$)—C(O)—CH$_2$—, —CH($R^2$)—CH($R^3$)—CH($R^4$)— and —C($R^2$)=CH—;
X is diazolyl or —N($R^5$)C(O)—;
$R^1$ is a phenyl group which is optionally substituted with from 1 to 3 groups, each independently selected from Cl and F;
$R^2$ is H or —O—(C$_1$-C$_6$ alkyl);
each occurrence of $R^4$ is independently selected from H and C$_1$-C$_6$ alkyl;
each occurrence of $R^5$ is independently H or C$_1$-C$_6$ alkyl;
$R^{7A}$ is H;
$R^{7B}$ is H, or $R^{7A}$ and $R^{7B}$, together with the common carbon atom to which they are each attached, join to form a spirocyclic 4- to 7-membered monocyclic heterocycloalkyl group; and
$R^8$ is selected from C$_1$-C$_6$ alkyl, —(C$_1$-C$_6$ alkylene)-O—(C$_1$-C$_6$ alkyl) and —(C$_1$-C$_6$ alkylene)-C$_3$-C$_7$ cycloalkyl.

In one embodiment, A is —CH$_2$—.
In another embodiment, A is —CH(—O—C$_1$-C$_6$ alkyl)-.
In another embodiment, A is —CH(—OCH$_3$)—.
In one embodiment, Y is —CH$_2$—.
In another embodiment, Y is —N(C$_1$-C$_6$ alkyl)-.
In another embodiment, Y is —N(CH$_3$)—.
In one embodiment, Z is —CH$_2$—.

In another embodiment, Z is —C(O)—
In another embodiment, Z is a bond.
In one embodiment, the -A-Y—Z— group is —CH($R^2$)—CH$_2$—.
In another embodiment, the -A-Y—Z— group is —CH$_2$—N($R^5$)—C(O)—CH$_2$—.
In another embodiment, the -A-Y—Z— group is —CH($R^2$)—CH($R^3$)—CH($R^4$)—.
In another embodiment, the -A-Y—Z— group is —C($R^2$)=CH—.
In one embodiment, the -A-Y—Z— group is —CH(—OCH$_3$)—CH$_2$—.
In another embodiment, the -A-Y—Z— group is —CH$_2$—N(CH$_3$)—C(O)—.
In another embodiment, the -A-Y—Z— group is —CH$_2$—CH$_2$—CH$_2$—.
In another embodiment, the -A-Y—Z— group is —CH=CH—.
In one embodiment, X is —NHC(O)—.
In another embodiment, X is 5 or 6-membered heteroaryl.
In another embodiment, X is 5-membered heteroaryl.
In still another embodiment, X is diazolyl or thiadiazolyl.
In another embodiment, X is diazolyl.
In one embodiment, $R^1$ is phenyl, which is substituted with from 1 to 3 groups, each independently selected from C$_1$-C$_6$ alkyl, halo and —O—(C$_1$-C$_6$ alkyl);
In one embodiment, $R^1$ is phenyl, which is substituted with 1 to 3 groups, each independently selected from Cl and F.
In another embodiment, $R^1$ is selected from:

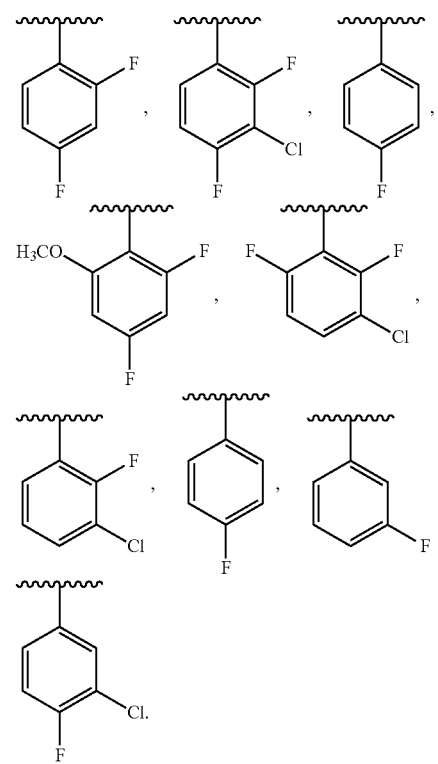

In one embodiment, $R^{7A}$ and $R^{7B}$ are each H.
In another embodiment, $R^{7A}$ and $R^{7B}$, together with the common carbon atoms to which they are attached, join to form a spirocyclic 4 to 7-membered heterocycloalkyl group.

In another embodiment, $R^{7A}$ and $R^{7B}$, together with the common carbon atoms to which they are attached, join to form a spirocyclic tetrahydrofuranyl group.

In one embodiment, $R^8$ is $C_1$-$C_6$ alkyl.

In another embodiment, $R^8$ is —($C_1$-$C_6$ alkylene)-O—($C_1$-$C_6$ alkyl).

In another embodiment, $R^8$ is —($C_1$-$C_6$ alkylene)-$C_3$-$C_7$ cycloalkyl

In still another embodiment, $R^8$ is selected methyl, ethyl, isopropyl, —$CH_2CH_2OCH_3$ and —$CH_2$-cyclopropyl.

In one embodiment, variables A, X, Y, Z, $R^1$, $R^{7A}$, $R^{7B}$ and $R^8$ for the Compounds of Formula (I) are selected independently of each other.

In another embodiment, the Compounds of Formula (I) are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors and HIV NNRTI inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors and HIV NNRTI inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HIV antiviral agents, immunomodulators, and anti-infective agents.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula (I) and (ii) a second therapeutic agent selected from the group consisting of HIV antiviral agents, immunomodulators, and anti-infective agents; wherein the pharmaceutically acceptable salt of the Compound of Formula (I) and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula (I).

(r) A method of treating HIV infection and/or reducing the likelihood or severity of symptoms of HIV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NSSB polymerase inhibitors.

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following: (w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula (I) and (ii) or a pharmaceutically acceptable salt thereof, a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula (I) or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula (I) or a pharmaceutically acceptable salt thereof.

(dd) The method of (cc), wherein the Compound of Formula (I) or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w) (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w) (x) or (y) or the combination of (z) or (aa).

The present invention also includes a compound of the present invention for use (i) in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula (I) include compounds 2-40 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the Schemes below. Alternative synthetic pathways and analogous structures will be apparent to those skilled in the art of organic synthesis.

Scheme 1 describes methods useful for preparing the compounds of Formula (I), wherein the -A-Y—Z— group is —CH(—O—$C_1$-$C_6$ alkyl)-$CH_2$—.

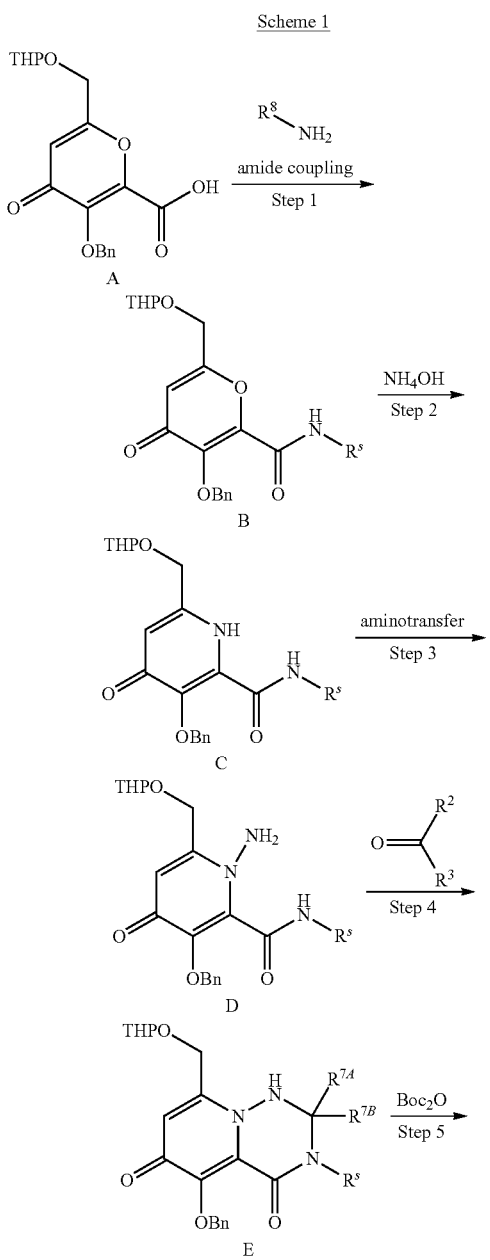

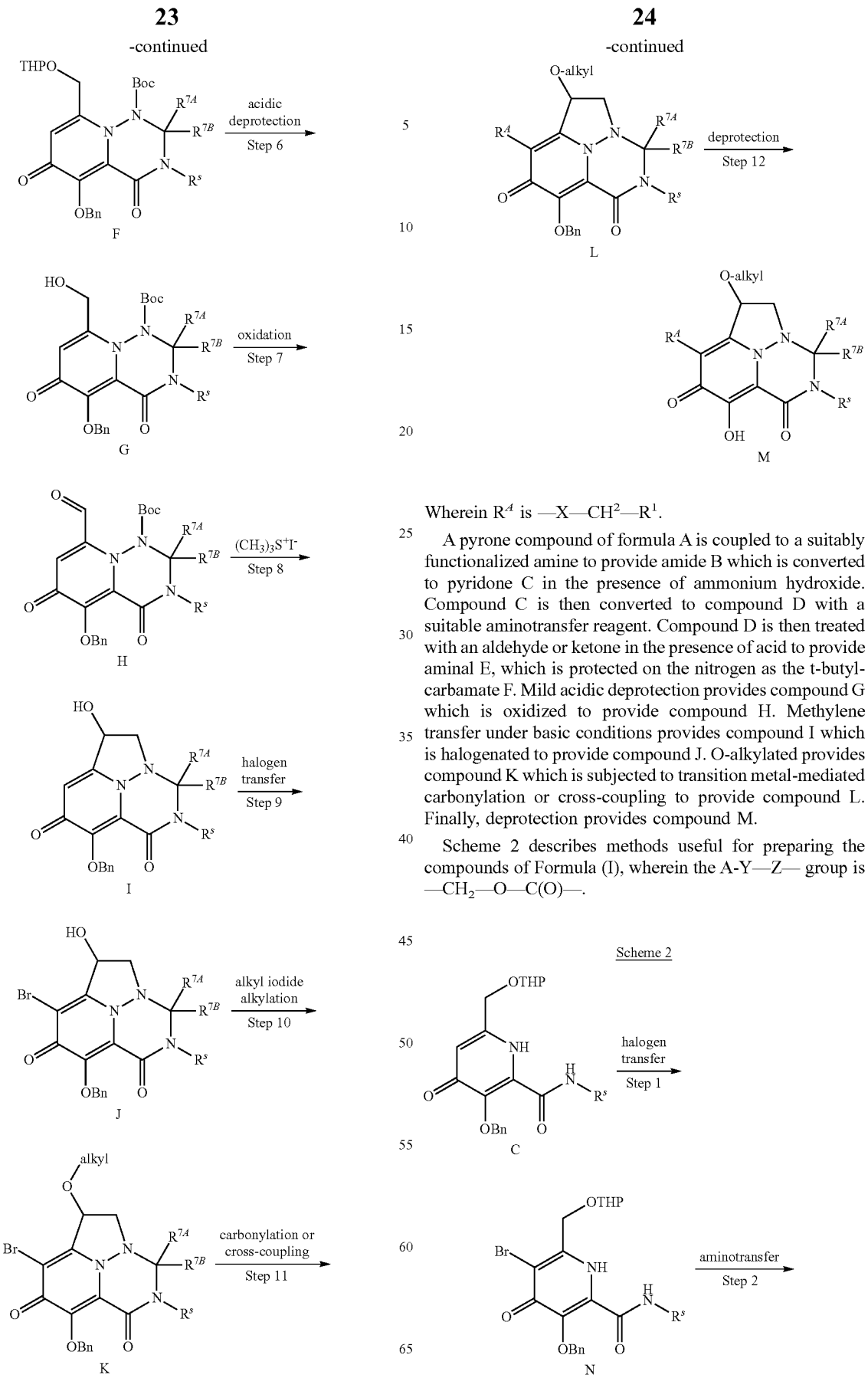

Wherein $R^A$ is —X—CH$^2$—R$^1$.

A pyrone compound of formula A is coupled to a suitably functionalized amine to provide amide B which is converted to pyridone C in the presence of ammonium hydroxide. Compound C is then converted to compound D with a suitable aminotransfer reagent. Compound D is then treated with an aldehyde or ketone in the presence of acid to provide aminal E, which is protected on the nitrogen as the t-butyl-carbamate F. Mild acidic deprotection provides compound G which is oxidized to provide compound H. Methylene transfer under basic conditions provides compound I which is halogenated to provide compound J. O-alkylated provides compound K which is subjected to transition metal-mediated carbonylation or cross-coupling to provide compound L. Finally, deprotection provides compound M.

Scheme 2 describes methods useful for preparing the compounds of Formula (I), wherein the A-Y—Z— group is —CH$_2$—O—C(O)—.

25

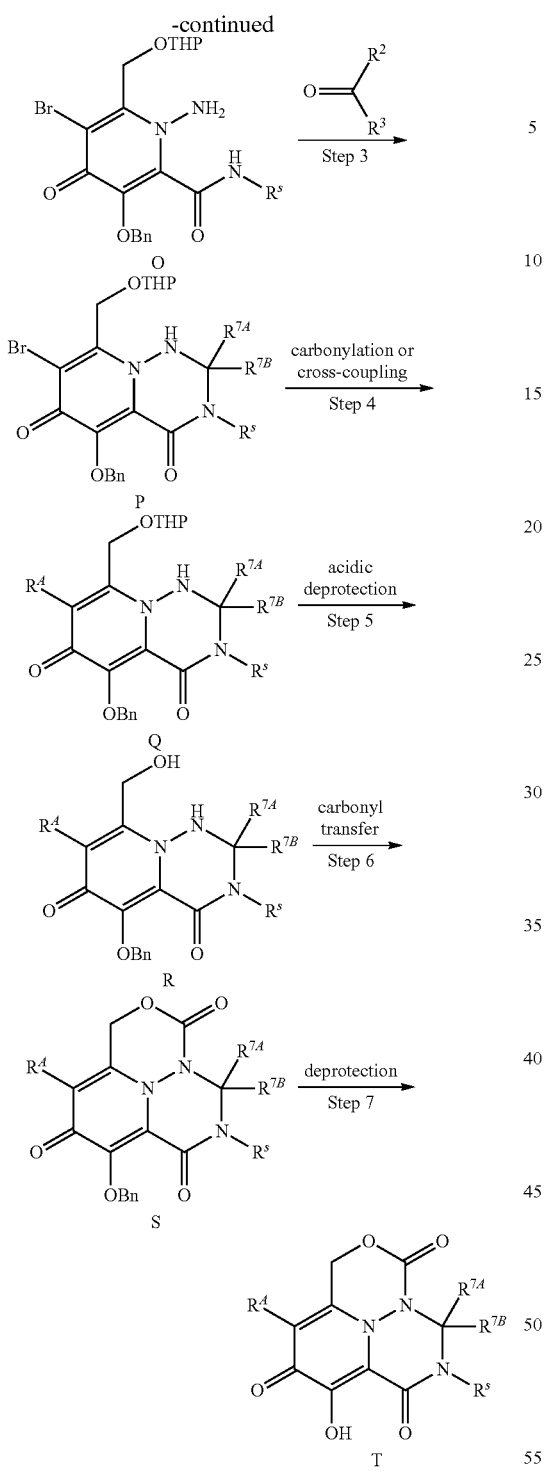

26

Scheme 3 describes methods useful for preparing the compounds of Formula (I), wherein the -A-Y—Z— group is —$CH_2$—N($R^5$)—C(O)—.

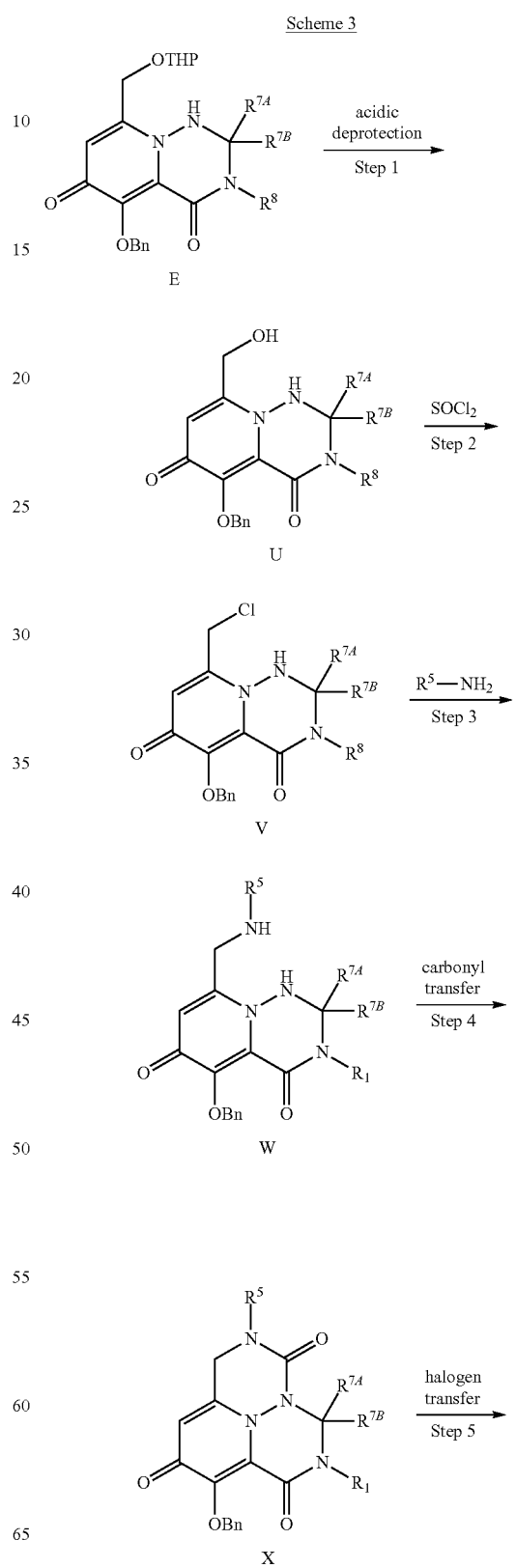

Wherein $R^A$ is —X—$CH_2$—$R^1$.

Compound C (from Scheme 1) is subjected to a suitable halogen transfer reagent to provide compound N. Compound N is then converted to compound O with a suitable aminotransfer reagent. Compound O is then treated with an aldehyde or ketone in the presence of acid to provide aminal P, which is subjected to transition metal-mediated carbonylation or cross-coupling to provide compound Q. Mild acidic deprotection provides compound R which is cyclized using a carbonyl transfer reagent to provide compound S. Finally, deprotection provides compound T.

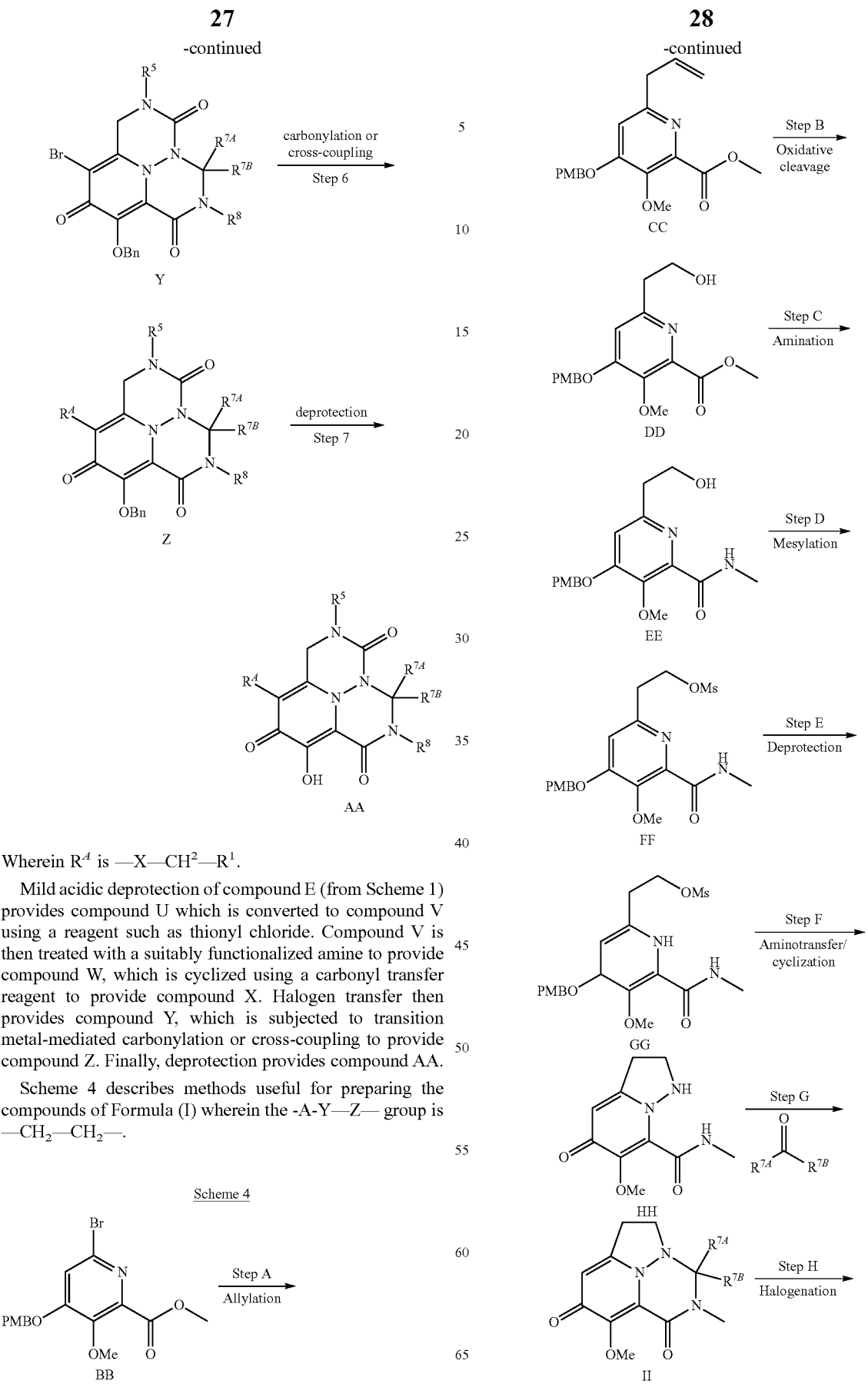

Wherein $R^A$ is —X—CH$_2$—R$^1$.

Mild acidic deprotection of compound E (from Scheme 1) provides compound U which is converted to compound V using a reagent such as thionyl chloride. Compound V is then treated with a suitably functionalized amine to provide compound W, which is cyclized using a carbonyl transfer reagent to provide compound X. Halogen transfer then provides compound Y, which is subjected to transition metal-mediated carbonylation or cross-coupling to provide compound Z. Finally, deprotection provides compound AA.

Scheme 4 describes methods useful for preparing the compounds of Formula (I) wherein the -A-Y—Z— group is —CH$_2$—CH$_2$—.

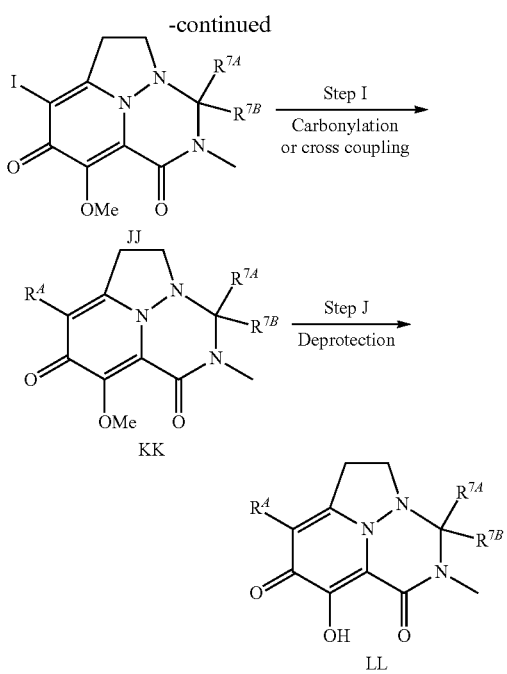

Wherein $R^A$ is —X—$CH^2$—$R^1$.

Allylation of BB yields CC, which is then converted to DD by oxidative cleavage. DD undergoes amination, with a reagent such as methanamine in THF, to yield EE. Mesylation of EE provides FF, which is then deprotected to yield GG. Aminotransfer and cyclization of GG provides HH, which is then treated with an aldehyde or ketone in the presence of acid to provide II. II undergoes halogenation with a reagent such as NIS, to yield JJ. JJ undergoes either carbonylation or cross coupling to provide KK, which is then deprotected to provide LL.

EXAMPLES

General Methods

The compounds described herein may be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures may be used to prepare these compounds. Concentration refers to the removal of the volatile components at reduced pressure (e.g. rotary evaporation) unless otherwise noted. All temperatures are degrees Celsius unless otherwise noted. Mass spectra (MS) were measured by electrospray ion-mass spectroscopy (ESI) in positive ion detection mode and m/z refers to the $[M+H]^+$ ion unless otherwise noted. $^1$H NMR spectra were recorded at 400-500 MHz at ambient temperature unless otherwise noted. RP-HPLC refers to reverse-phase HPLC on C18-functionalized preparative or semi-preparative columns with gradient elution using acetonitrile and water modified with trifluoroacetic acid as eluents and fractions were lyophilized or concentrated in vacuo by rotary evaporation unless otherwise noted. Purification by column chromatography on silica gel was accomplished using a flash chromatography system (e.g. ISCO or Biotage) and commercial pre-packed silica gel columns with elution using the stated solvent systems. Compounds described herein were synthesized as the racemates unless otherwise noted in the experimental procedures and compound tables. For stereoisomers, enantiomer A refers to the earlier eluting enantiomer and enantiomer B refers to the later eluting enantiomer at the point of separation and this nomenclature is maintained through the remainder of a synthetic sequence for a given enantiomeric series regardless of the possibility that subsequent intermediates and final compounds may have the same or opposite orders of elution. Diastereomer 1 refers to the earlier eluting diastereomer and diastereomer 2 refers to the later eluting diastereomer and this nomenclature is maintained through the remainder of a synthetic sequence for a given diastereomeric series regardless of the possibility that subsequent intermediates and final compounds may have the same or opposite orders of elution.

Example 1

Preparation of Intermediate Compound 1

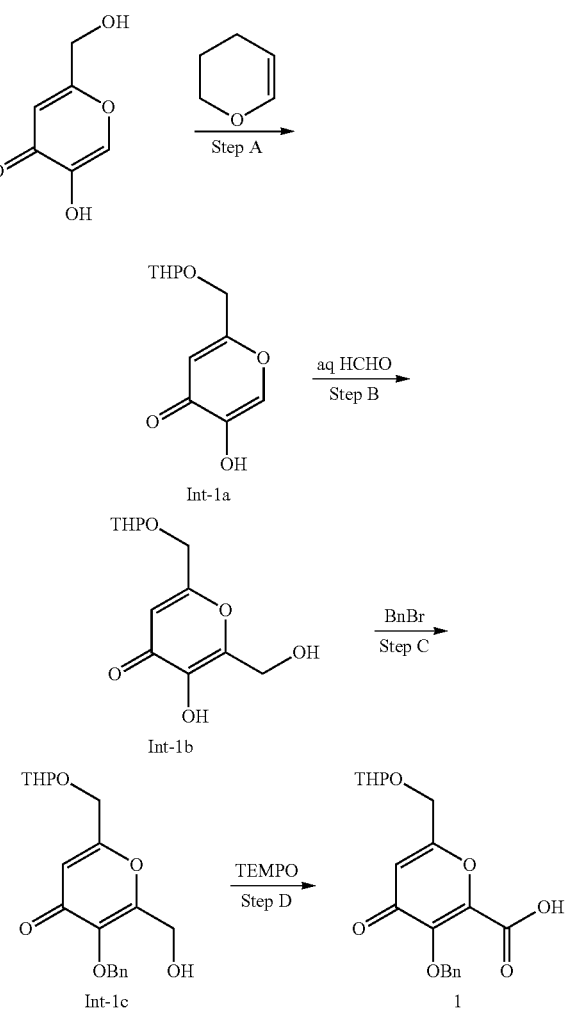

Step A Synthesis of Intermediate Compound Int-1a

Into a 100-L reactor purged and maintained with an inert atmosphere of nitrogen, was charged a solution of 5-hydroxy-2-(hydroxymethyl)-4H-pyran-4-one (5 kg, 35.18 mol, 1.00 equiv) in dichloromethane (50 L) and 3,4-dihydro-2H-pyran (3.54 kg, 42.08 mol, 1.20 equiv). This was followed by the addition of p-toluenesulfonic acid monohydrate (60 g, 315 mmol, 0.01 equiv) in several batches at 10° C. in 20 min. The resulting solution was stirred for 3 hours at room temperature. The solution was adjusted to pH 7 with sodium hydroxide (5 mol/L). The organic phase was washed with 1×10 L of brine and concentrated in vacuo to provide Int-1a, which was used without further purification.

Step B—Synthesis of Intermediate Compound Int-1b

Into a 50-L 4-necked round-bottom flask purged and maintained with an inert atmosphere of nitrogen, was placed a solution of Int-1a (5.5 kg, 24.31 mol, 1.00 equiv) in water (27.5 L), sodium hydroxide (973.5 g, 24.34 mol, 1.00 equiv), formaldehyde (2.15 kg, 26.49 mol, 1.09 equiv, 37% aqueous). The resulting solution was stirred overnight at room temperature then adjusted to pH 5 using acetic acid. The resulting solution was extracted with 5×20 L of ethyl acetate and the organic layers combined. The resulting mixture was washed with 5 L of brine, then dried over anhydrous sodium sulfate and concentrated in vacuo to provide Int-1b, which was used without further purification.

Step C—Synthesis of Intermediate Compound Int-1c

Into a 50-L, 4-necked, round-bottom flask purged and maintained with an inert atmosphere of nitrogen, was placed a solution of Int-1b (5.6 kg, 21.85 mol, 1.00 equiv) in N,N-dimethylformamide (20 L), potassium carbonate (6.04 kg, 43.70 mol, 2.00 equiv) and benzyl bromide (3.93 kg, 22.98 mol, 1.05 equiv). The resulting solution was stirred overnight at room temperature. The reaction was then quenched by pouring into 100 L of water. The resulting solution was extracted with 3×20 L of ethyl acetate and the organic layers combined and concentrated in vacuo to provide Int-1c, which was used without further purification.

Step C—Synthesis of Intermediate Compound 1

Into a 50-L, 4-necked, round-bottom flask, was charged a solution of Int-1c (5 kg, 14.44 mol, 1.00 equiv) in dichloromethane (25 L), a solution of KBr (343.6 g, 2.89 mol, 0.20 equiv) in water (5 L), a solution of KHCO$_3$ (5.058 kg, 50.58 mol, 3.50 equiv) in water (20 L) and 2,2,6,6-tetramethylpiperidine 1-oxyl (TEMPO) (40.75 g, 0.02 equiv). This was followed by the dropwise addition of NaClO (30 kg, 32%) with stirring at 5° C. over 4 hr. The resulting solution was stirred overnight at room temperature. The resulting solution was extracted with 2×10 L of dichloromethane and the aqueous layers combined. The pH value of the solution was adjusted to 3 with aqueous hydrogen chloride (6 mol/L). The resulting solution was extracted with 3×20 L of ethyl acetate and the organic layers combined and dried over anhydrous sodium sulfate and concentrated in vacuo to provide Intermediate Compound 1. $^1$H NMR (400 MHz, CDCl$_3$) δ 7.50 (5H, m), 6.66 (1H, s), 5.65 (2H, s), 4.76 (1H, s), 4.64 (1H, m), 4.45 (1H, m), 3.82 (1H, m), 3.58 (1H, m), 1.69-1.90 (6H, m). Mass Calc'd for C$_{19}$H$_{20}$O$_7$: 360.1, found 361.1 (M+H)$^+$.

Example 2

Preparation of Compound 2

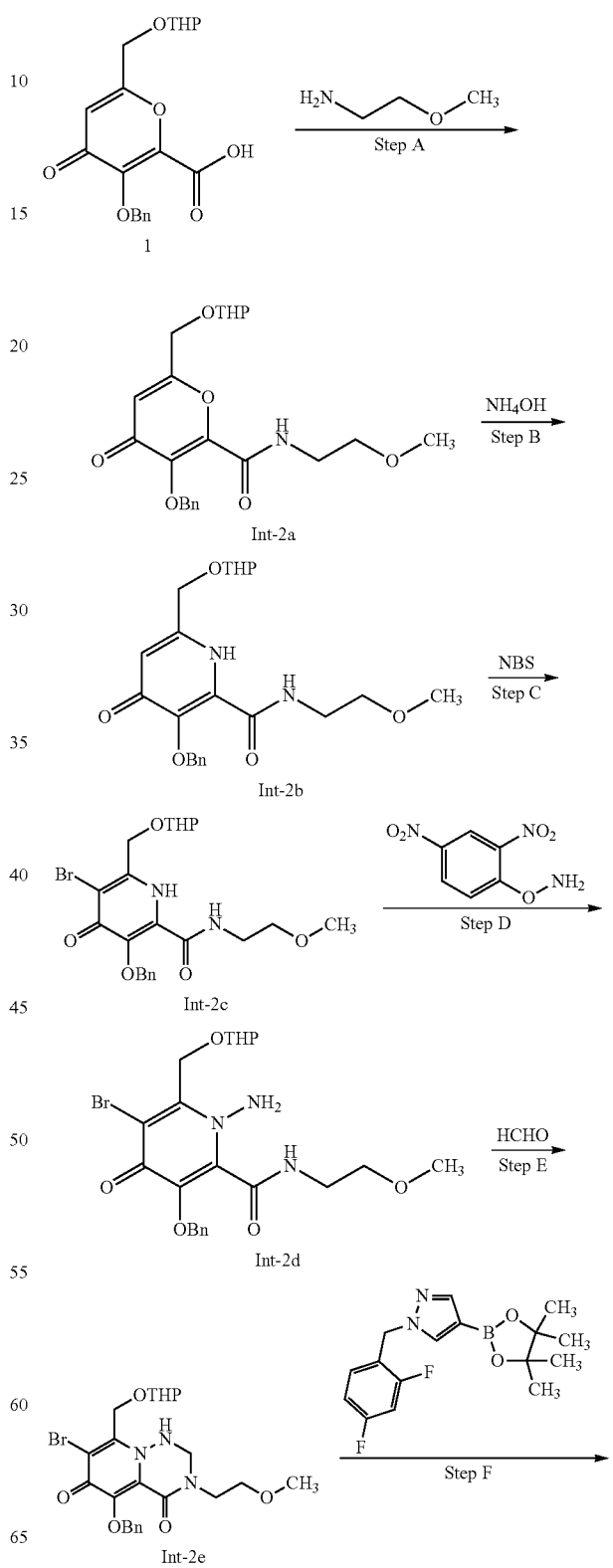

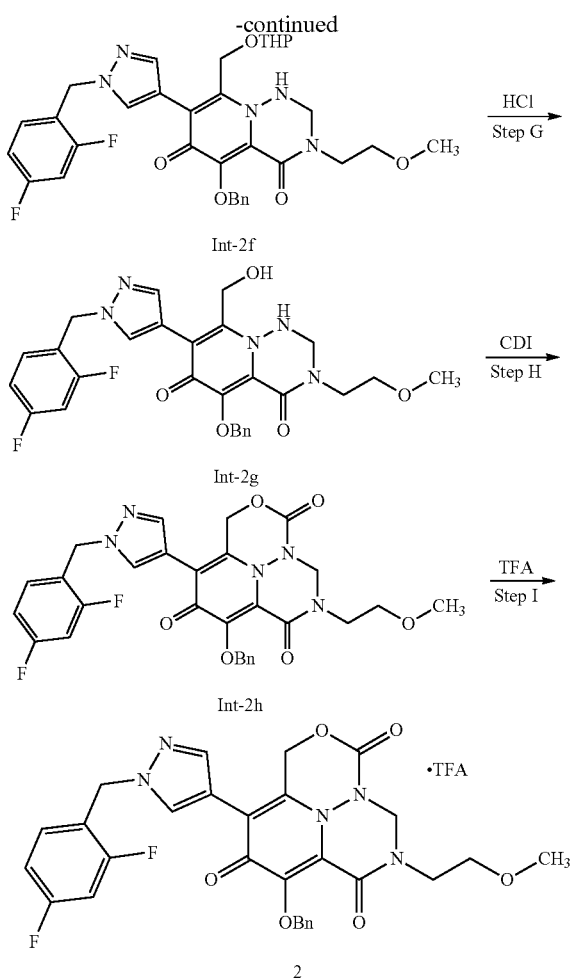

Step A—Synthesis of Intermediate Compound Int-2a

To a solution of intermediate compound 1 (3.0 g, 8.3 mmol) in anhydrous N,N-dimethylformamide (30 mL) was added 2-methoxyethanamine (750 mg, 10.0 mmol), 1-[bis (dimethylamino)methylene]-1H-1,2,3-triazolo[4,5-b]pyridinium 3-oxid hexafluorophosphate (1.7 g, 10.0 mmol) and N,N-diisopropylethylamine (2.6 g, 20 mmol). The mixture was allowed to stir at room temperature for 16 hours, diluted with water and extracted with ethyl acetate. The combined organic portions were washed with brine, dried over anhydrous $Na_2SO_4$, filtered and the filtrate was concentrated in vacuo. The crude product was purified using column chromatography (petroleum ether:ethyl acetate=5:1) to provide Int-2a. Mass Calc'd for $C_{22}H_{27}NO_7$: 417.2, found 418.2 $(M+H)^+$.

Step B—Synthesis of Intermediate Compound Int-2b

To a solution of Int-2a (2.5 g, 5.9 mmol) in ethanol (30 mL) was added ammonium hydroxide (28% aqueous, 3 mL) and the mixture was allowed to stir at room temperature for 2 days. The mixture was concentrated to provide crude compound Int-2b, which was used without further purification. Mass Calc'd for $C_{22}H_{28}N_2O_6$: 416.2, found 417.2 $(M+H)^+$.

Step C—Synthesis of Intermediate Compound Int-2c

To a solution of Int-2b (2.0 g, 4.8 mmol) in dichloromethane (15 mL) was added N-bromosuccinimide (885 mg, 5 mmol) at 0° C. The mixture was allowed to stir at 20° C. for 16 hours, quenched with saturated aqueous $NaHCO_3$, extracted with dichloromethane. The combined organic portions were concentrated in vacuo to provide Int-2c, which was used without further purification. Mass Calc'd for $C_{22}H_{27}BrN_2O_6$: 494.1, 496.1 found 495.1, 497.1 $(M+H)^+$.

Step D—Synthesis of Intermediate Compound Int-2d

To a solution of Int-2c (1.9 g, 3.85 mmol) and $K_2CO_3$ (690 mg, 5 mmol) in N,N-dimethylformamide (20 mL) was added O-(2,4-dinitrophenyl)hydroxylamine (895 mg, 4.5 mmol). The mixture was allowed to stir at 20° C. for 3 days. After filtration and concentration, the resulting residue was purified using preparative RP-HPLC to provide Int-2d. Mass Calc'd for $C_{22}H_{28}BrN_3O_6$: 509.1, 511.1 found 510.1, 512.1 $(M+H)^+$.

Step E—Synthesis of Intermediate Compound Int-2e

To a solution of Int-2d (700 mg, 1.38 mmol) and acetic acid (3 mL) in tetrahydrofuran (20 mL) was added paraformaldehyde (41 mg, 1.38 mmol). The mixture was allowed to stir at 70° C. for 12 hours. After concentration, the resulting residue was purified using preparative TLC on silica gel (100% ethyl acetate) to provide Int-2e. $^1$H NMR (400 MHz, $CD_3CN$) δ 7.55-7.57 (m, 2H), 7.31-7.40 (m, 3H), 5.89-5.93 (t, J=8.0 Hz, 1H), 5.17 (s, 2H), 5.06-5.09 (m, 1H), 4.84-4.87 (m, 1H), 4.75-4.77 (t, J=4.0 Hz, 1H), 4.52-4.54 (m, 2H), 3.80-3.85 (m, 1H), 3.62-3.65 (m, 2H), 3.47-3.54 (m, 3H), 3.32 (s, 3H), 1.58-1.78 (m, 2H), 1.53-1.57 (m, 4H). Mass Calc'd for $C_{23}H_{28}BrN_3O_6$: 521.1, 523.1, found 522.1, 524.1, $(M+H)^+$.

Step F—Synthesis of Intermediate Compound Int-2f

To a solution of Int-2e (100 mg, 0.19 mmol) in dioxane (10 mL) was added 1-(2,4-difluorobenzyl)-4-(4,4,5,5-tetramethyl-1,3,2-dioxaborolan-2-yl)-1H-pyrazole (96 mg, 0.3 mmol), $Cs_2CO_3$ (78 mg, 0.24 mmol) and $Pd(PPh_3)_4$ (21 mg, 0.019 mmol). The mixture was allowed to stir at 80° C. for 16 hours, cooled to room temperature, diluted with water and extracted with ethyl acetate. The combined organic portions were dried over anhydrous $Na_2SO_4$, filtered and the filtrate was concentrated in vacuo. The resulting residue was purified using preparative TLC on silica gel (100% ethyl acetate) to provide Int-2f, which was used without further purification. Mass Calc'd for $C_{33}H_{35}F_2N_5O_6$: 635.3, found 636.1 $(M+H)^+$.

Step G—Synthesis of Intermediate Compound Int-2g

To a solution of Int-2f (80 mg, 0.13 mmol) in ethyl acetate (15 mL) was added a solution of HCl in ethyl acetate (4 M, 1 mL, 4.0 mmol) at 0° C. The mixture was allowed to stir at 20° C. for 1 hour and concentrated in vacuo to provide Int-2g, which was used without further purification. Mass Calc'd for $C_{28}H_{27}F_2N_5O_5$: 551.2, found 552.1 $(M+H)^+$.

Step H—Synthesis of Intermediate Compound Int-2h

To a solution of Int-2g (60 mg, 0.11 mmol) in dichloromethane (15 mL) was added 1,1'-carbonyldiimidazole (24 mg, 0.15 mmol) at 0° C. The mixture was allowed to stir at 20° C. for 3 hours and then concentrated in vacuo to provide Int-2h, which was used without further purification. Mass Calc'd for $C_{29}H_{25}F_2N_5O_6$: 577.2, found 578.1 $(M+H)^+$.

Step I—Synthesis of Compound 2

To a solution of Int-2h (43 mg, 0.07 mmol) in dichloromethane (5 mL) was added trifluoroacetic acid (1 mL). The mixture was allowed to stir at 20° C. for 3 hours. The mixture was concentrated in vacuo and the resulting residue was purified using preparative RP-HPLC to provide compound 2. $^1$H NMR (400 MHz, $CD_3CN$) 7.98 (s, 1H), 7.56 (s, 1H), 7.28-7.34 (m, 1H), 6.96-7.03 (m, 2H), 5.38 (s, 2H), 5.37 (s, 2H), 5.31 (s, 2H), 3.74-3.76 (t, J=4.0 Hz, 2H), 3.60-3.62 (t, J=4.0 Hz, 2H), 3.34 (s, 3H). Mass Calc'd for $C_{22}H_{19}F_2N_5O_6$: 487.1, found 488.1 (M+H)+.

Example 3

Preparation of Compound 3

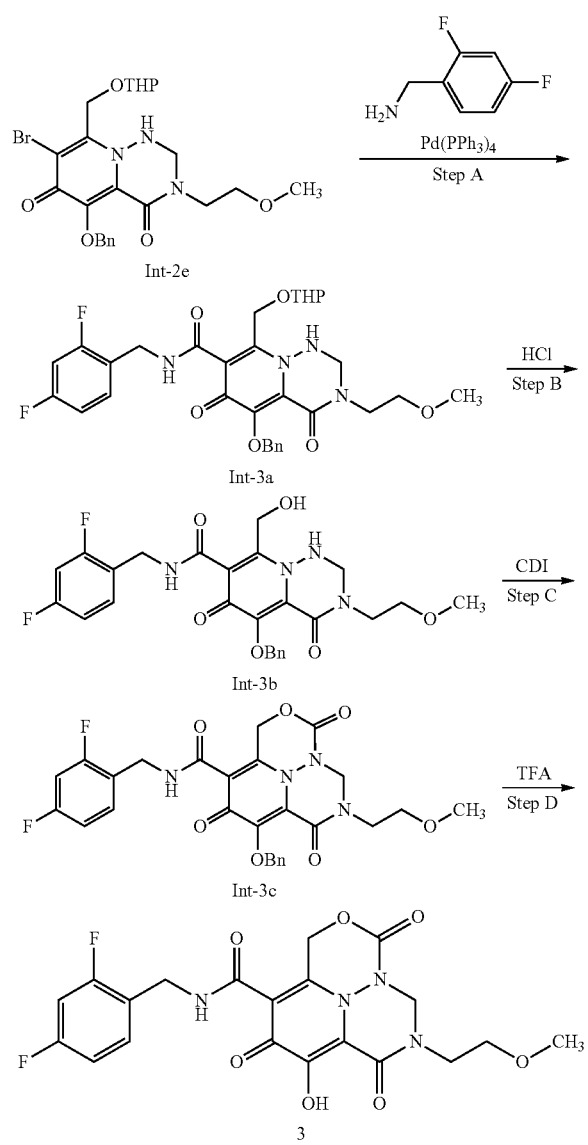

Step A—Synthesis of Intermediate Compound Int-3a

To a solution of Int-2e (40 mg, 0.08 mmol) in dimethylsulfoxide (1 mL) and methanol (4 mL) was added (2,4-difluorophenyl)methanamine (55 mg, 0.38 mmol). The mixture was allowed to stir at 80° C. under carbon monoxide (1 atm) for 16 hours. The mixture was partitioned between ethyl acetate and water. The organic layer was separated and concentrated in vacuo. The resulting residue was purified using preparative TLC on silica gel (dichloromethane:ethyl acetate=1:1) to provide compound Int-3a. $^1$H NMR (400 MHz, CDCl$_3$) δ 10.07 (s, 1H), 7.44-7.63 (m, 2H), 7.30-7.36 (m, 4H), 6.80-7.26 (m, 1H), 5.31-5.54 (m, 1H), 5.23-5.29 (m, 3H), 4.67-4.80 (m, 1H), 4.64 (d, J=5.6 Hz, 2H), 4.51 (d, J=8.0 Hz, 2H), 3.79-3.81 (m, 1H), 3.67-3.70 (m, 5H), 3.50 (s, 3H), 1.72-1.76 (m, 2H), 1.60 (s, 3H), 1.25 (m, 2H). Mass Calc'd for $C_{31}H_{34}F_2N_4O_7$: 612.2, found 613.2 (M+H)+.

Step B—Synthesis of Intermediate Compound Int-3b

To a solution of Int-3a (30 mg, 0.05 mmol) in ethyl acetate (1 mL) was added a solution of HCl in ethyl acetate (4 M, 0.3 mL) at 0° C. The mixture was allowed to stir at room temperature for 5 min and then concentrated in vacuo to provide crude Int-3b, which was used without further purification. Mass Calc'd for $C_{26}H_{26}F_2N_4O_6$: 528.2, found 529.1 (M+H)+.

Step C—Synthesis of Intermediate Compound Int-3c

To a solution of Int-3b (20 mg, 0.04 mmol) and 4-dimethylaminopyridine (40 mg, 0.32 mmol) in dichloromethane (2 mL) was added 1,1'-carbonyldiimidazole (40 mg, 0.24 mmol) at 20° C. The mixture was allowed to stir at 20° C. for 16 hours and then extracted from water with ethyl acetate. The combined organic portions were washed with 10% aqueous HCl, concentrated in vacuo and the resulting residue was purified using preparative TLC on silica gel (dichloromethane:ethyl acetate=1:1) to provide Int-3c. Mass Calc'd for $C_{27}H_{24}F_2N_4O_7$: 554.2, found 555.1 (M+H)+.

Step D—Synthesis of Compound 3

A solution of Int-3c (16 mg, 0.032 mmol) in trifluoroacetic acid (2 mL) and dichloromethane (1 mL) was allowed to stir at 20° C. for 1 hour. The mixture was concentrated in vacuo and the resulting residue was purified using preparative RP-HPLC to provide compound 3. $^1$H NMR (400 MHz, CD$_3$OD) δ 7.44-7.48 (m, 1H), 6.93-6.98 (m, 2H), 5.95 (s, 2H), 5.49 (s, 2H), 4.60 (s, 2H), 3.77-3.83 (m, 2H), 3.65-3.67 (m, 2H), 3.38 (s, 3H). Mass Calc'd for $C_{20}H_{18}F_2N_4O_7$: 464.1, found 465.1 (M+H)+.

Example 4

Preparation of Compound 4

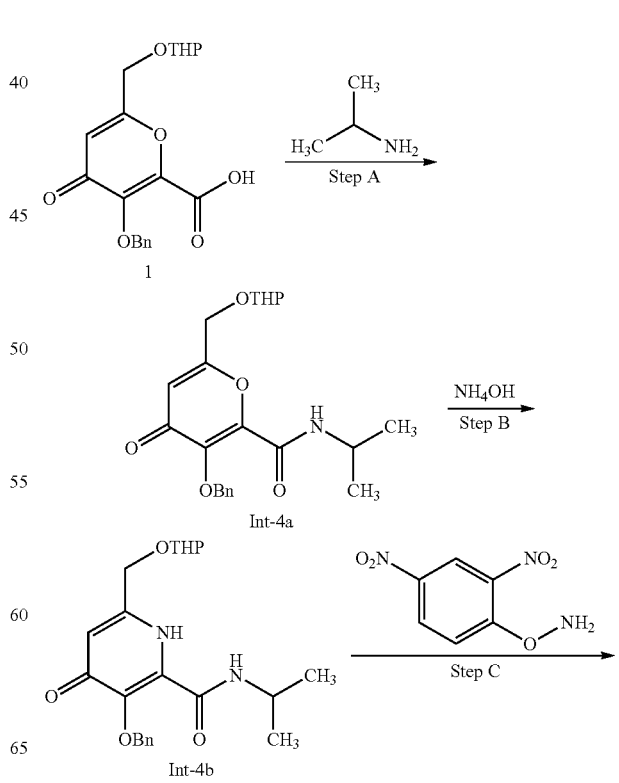

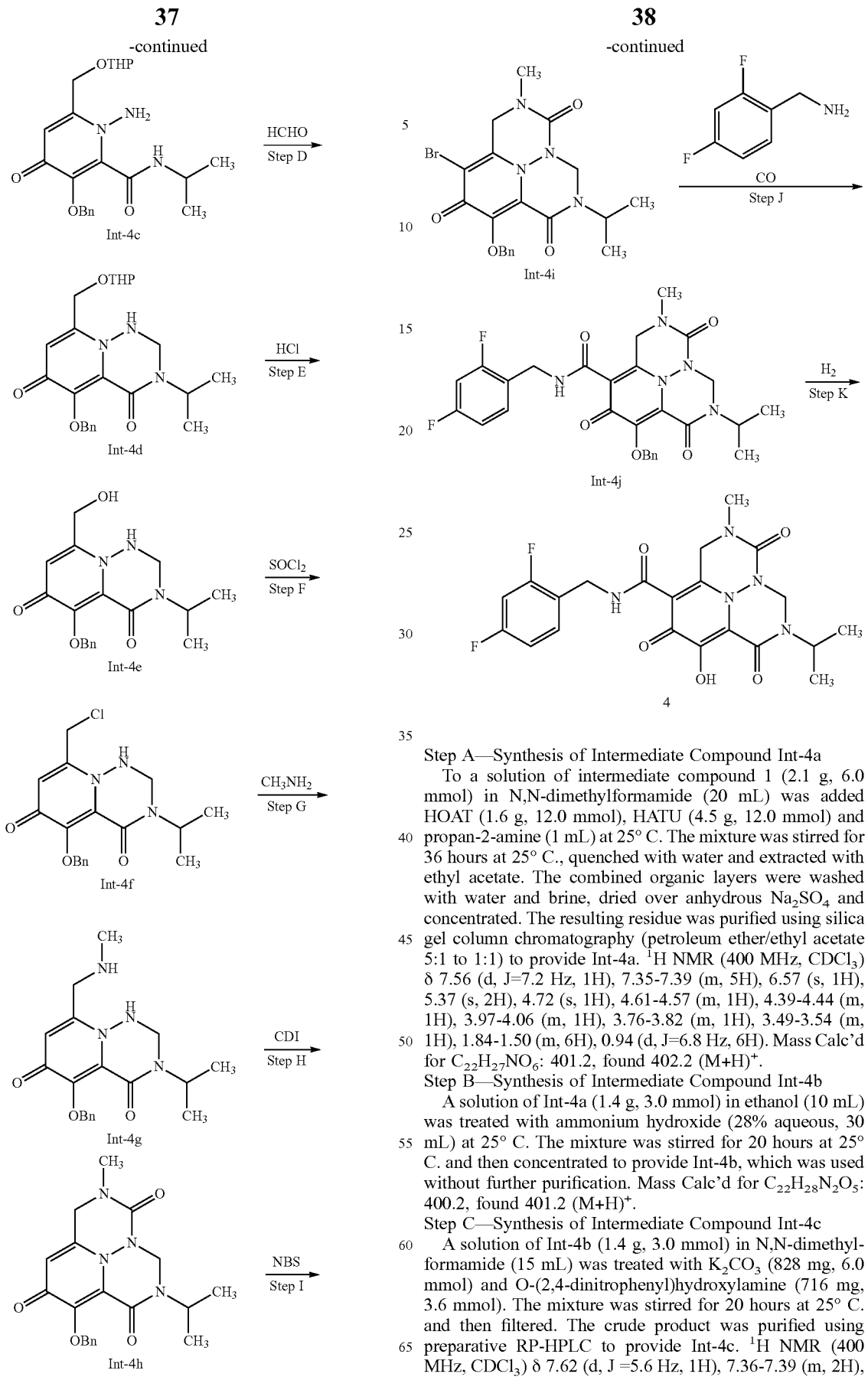

Step A—Synthesis of Intermediate Compound Int-4a

To a solution of intermediate compound 1 (2.1 g, 6.0 mmol) in N,N-dimethylformamide (20 mL) was added HOAT (1.6 g, 12.0 mmol), HATU (4.5 g, 12.0 mmol) and propan-2-amine (1 mL) at 25° C. The mixture was stirred for 36 hours at 25° C., quenched with water and extracted with ethyl acetate. The combined organic layers were washed with water and brine, dried over anhydrous $Na_2SO_4$ and concentrated. The resulting residue was purified using silica gel column chromatography (petroleum ether/ethyl acetate 5:1 to 1:1) to provide Int-4a. $^1$H NMR (400 MHz, $CDCl_3$) δ 7.56 (d, J=7.2 Hz, 1H), 7.35-7.39 (m, 5H), 6.57 (s, 1H), 5.37 (s, 2H), 4.72 (s, 1H), 4.61-4.57 (m, 1H), 4.39-4.44 (m, 1H), 3.97-4.06 (m, 1H), 3.76-3.82 (m, 1H), 3.49-3.54 (m, 1H), 1.84-1.50 (m, 6H), 0.94 (d, J=6.8 Hz, 6H). Mass Calc'd for $C_{22}H_{27}NO_6$: 401.2, found 402.2 $(M+H)^+$.

Step B—Synthesis of Intermediate Compound Int-4b

A solution of Int-4a (1.4 g, 3.0 mmol) in ethanol (10 mL) was treated with ammonium hydroxide (28% aqueous, 30 mL) at 25° C. The mixture was stirred for 20 hours at 25° C. and then concentrated to provide Int-4b, which was used without further purification. Mass Calc'd for $C_{22}H_{28}N_2O_5$: 400.2, found 401.2 $(M+H)^+$.

Step C—Synthesis of Intermediate Compound Int-4c

A solution of Int-4b (1.4 g, 3.0 mmol) in N,N-dimethylformamide (15 mL) was treated with $K_2CO_3$ (828 mg, 6.0 mmol) and O-(2,4-dinitrophenyl)hydroxylamine (716 mg, 3.6 mmol). The mixture was stirred for 20 hours at 25° C. and then filtered. The crude product was purified using preparative RP-HPLC to provide Int-4c. $^1$H NMR (400 MHz, $CDCl_3$) δ 7.62 (d, J =5.6 Hz, 1H), 7.36-7.39 (m, 2H), 7.28-7.30 (m, 3H), 6.39 (s, 1H), 5.33 (s, 2H), 5.07-5.11 (m, 2H), 4.68-4.73 (m, 2H), 4.49 (d, J=14.4 Hz, 1H), 4.03-4.12 (m, 1H), 3.79-3.85 (m, 1H), 3.51-3.56 (m, 1H), 1.54-1.86 (m, 6H), 1.08 (d, J=6.4 Hz, 6H). Mass Calc'd for $C_{22}H_{29}N_3O_5$: 415.2, found 416.2 (M+H)$^+$.

Step D—Synthesis of Intermediate Compound Int-4d

To a solution of compound Int-4c (100 mg, 0.24 mmol) in tetrahydrofuran (20 mL) was added paraformaldehyde (18 mg, 0.6 mmol) and acetic acid (0.8 mL). The mixture was heated to 80° C. for 3 hours and then concentrated in vacuo to provide the crude product Int-4d which was used without further purification. $^1$H NMR (400 MHz, CD$_3$OD) δ 7.45-7.46 (m, 2H), 7.29-7.30 (m, 3H), 6.68 (s, 1H), 5.19 (s, 2H), 4.76-4.78 (m, 2H), 4.61-4.64 (s, 3H), 4.07-4.08 (m, 1H), 3.82-3.84 (m, 1H), 3.52-3.55 (m, 1H), 1.57-2.00 (m, 6H), 1.22 (d, J=6.8 Hz, 6H); Mass Calc'd for $C_{23}H_{29}N_3O_5$: 427.2, found 428.2 (M+H)$^+$.

Step E—Synthesis of Intermediate Compound Int-4e

To a solution of compound Int-4d (52 mg, 0.121 mmol) in ethyl acetate (5 mL) was added a solution of HCl in ethyl acetate (4 M, 1.5 mL) at 0° C. The mixture was stirred for 20 min at 0° C. and then concentrated in vacuo to provide crude Int-4e, which was used in the next step without further purification. Mass Calc'd for $C_{18}H_{21}N_3O_4$: 343.2, found 344.2 (M+H)$^+$.

Step F—Synthesis of Intermediate Compound Int-4f

To a solution of compound Int-4e (40 mg, 0.116 mmol) in dichloromethane (12 mL) was added SOCl$_2$ (0.1 mg, 0.166 mmol) at 0° C. The mixture was stirred for 4 hours at 25° C. and then concentrated in vacuo to provide crude Int-4f, which was used without further purification. Mass Calc'd for $C_{18}H_{20}ClN_3O_3$: 361.1, found 362.2 (M+H)$^+$.

Step G—Synthesis of Intermediate Compound Int-4g

Compound Int-4f (40 mg, 0.086 mmol) was dissolved with MeNH$_2$ in methanol (5 mL), the mixture was allowed to stir at room temperature for 20 min. The reaction mixture was concentrated in vacuo to provide the crude product Int-4g (37 mg, yield: 94.8%), which was used in the next step without further purification. Mass Calc'd for $C_{19}H_{24}N_4O_3$: 356.2, found 357.2 (M+H)$^+$.

Step H—Synthesis of Intermediate Compound Int-4h

To a solution of crude Int-4g (37 mg, 0.103 mmol) in dimethylsulfoxide/dichloromethane (1 mL/10 mL) was added 4-dimethylaminopyridine (101 mg, 0.82 mmol) and CDI (101 mg, 0.62 mmol). The mixture was allowed to stir at room temperature for 3 days and then diluted with dichloromethane (20 mL), washed with 0.5% aqueous HCl and water (15 mL), dried with anhydrous Na$_2$SO$_4$, filtered and the filtrate was concentrated in vacuo give crude Int-4h, which was used without further purification. Mass Calc'd for $C_{20}H_{22}N_4O_4$: 382.2, found 383.2 (M+H)$^+$.

Step I—Synthesis of Intermediate Compound Int-4i

To a solution of compound Int-4h (30 mg, 0.078 mmol) in acetonitrile (20 mL) was added N-bromosuccinimide (20 mg, 0.12 mmol). The mixture was allowed to stir at room temperature for 1 hour and then concentrated in vacuo. The resulting residue was purified using preparative TLC (100% ethyl acetate) to provide compound Int-4i. $^1$H NMR (400 MHz, CD$_3$OD) δ 7.53-7.55 (m, 2H), 7.34-7.37 (m, 3H), 5.26 (s, 2H), 5.17 (s, 2H), 4.64-4.65 (s, 2H), 4.64 (m, 1H), 3.06 (s, 3H), 1.30 (d, J=8 Hz, 6H). Mass Calc'd for $C_{20}H_{21}BrN_4O_4$: 460.1, found 461.1 (M+H)$^+$.

Step J—Synthesis of Intermediate Compound Int-4j

A solution of Int-4i (17 mg, 0.037 mmol) in dimethylsulfoxide (2 mL) and methanol (6 mL) was treated with (2,4-difluorophenyl)methanamine (26 mg, 0.184 mmol), N,N-diisopropylethylamine (24 mg, 0.18 mmol) and Pd(PPh$_3$)$_4$ (1.53 mg, 0.0013 mmol). The mixture was stirred under carbon monoxide (1 atm) at 80° C. for 15 hours, cooled to rt and quenched with water (4 mL). The mixture extracted with ethyl acetate and the organic portions were washed with water and concentrated in vacuo. The resulting residue was purified using preparative-TLC on silica gel (dichloromethane:MeOH=20:1) to provide Int-4j. Mass Calc'd for $C_{28}H_{27}F_2N_5O_5$: 551.2, found 552.2 (M+H)$^+$.

Step K—Synthesis of Compound 4

A solution of Int-4j (17 mg, 0.031 mmol) in dichloromethane (1 mL) was treated with trifluoroacetic acid (2 mL) at 25° C. The mixture was allowed to stir at 25° C. for 1 hour and then concentrated in vacuo. The resulting residue was purified using preparative RP-HPLC to provide compound 4. $^1$H NMR (400 MHz, CD$_3$OD) δ 7.45-7.50 (m, 1H), 6.94-7.00 (m, 2H), 5.37 (s, 2H), 5.13 (s, 2H), 4.75-4.80 (m, 1H), 4.62 (s, 2H), 3.02 (s, 3H), 1.36 (t, J=6.8 Hz, 6H). Mass Calc'd for $C_{21}H_{21}F_2N_5O_5$: 461.2, found 462.2 (M+H)$^+$.

Example 5

Preparation of Compound 5

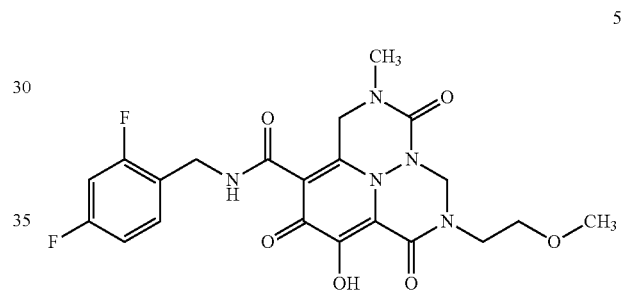

Compound 5 was made using the methods described in Example 4. $^1$H NMR (400 MHz, CD$_3$OD) δ 7.45-7.51 (m, 1H), 6.94-7.00 (m, 2H), 5.43 (s, 2H), 5.13 (s, 2H), 4.62 (s, 2H), 3.82 (t, J=9.6 Hz, 2H), 3.68 (t, J=9.6 Hz, 2H), 3.40 (m, 3H), 3.02 (s, 3H). Mass Calc'd for $C_{21}H_{21}F_2N_5O_6$: 477.1, found 478.2 (M+H)$^+$.

Example 6

Preparation of Compound 6

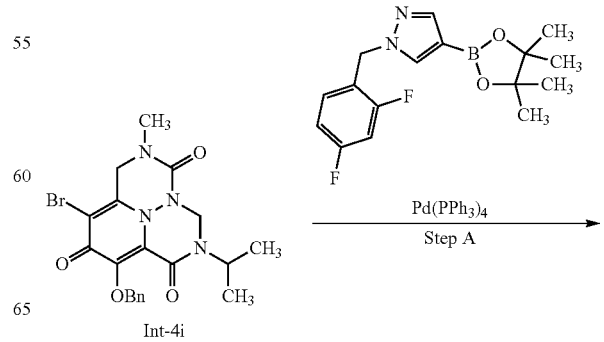

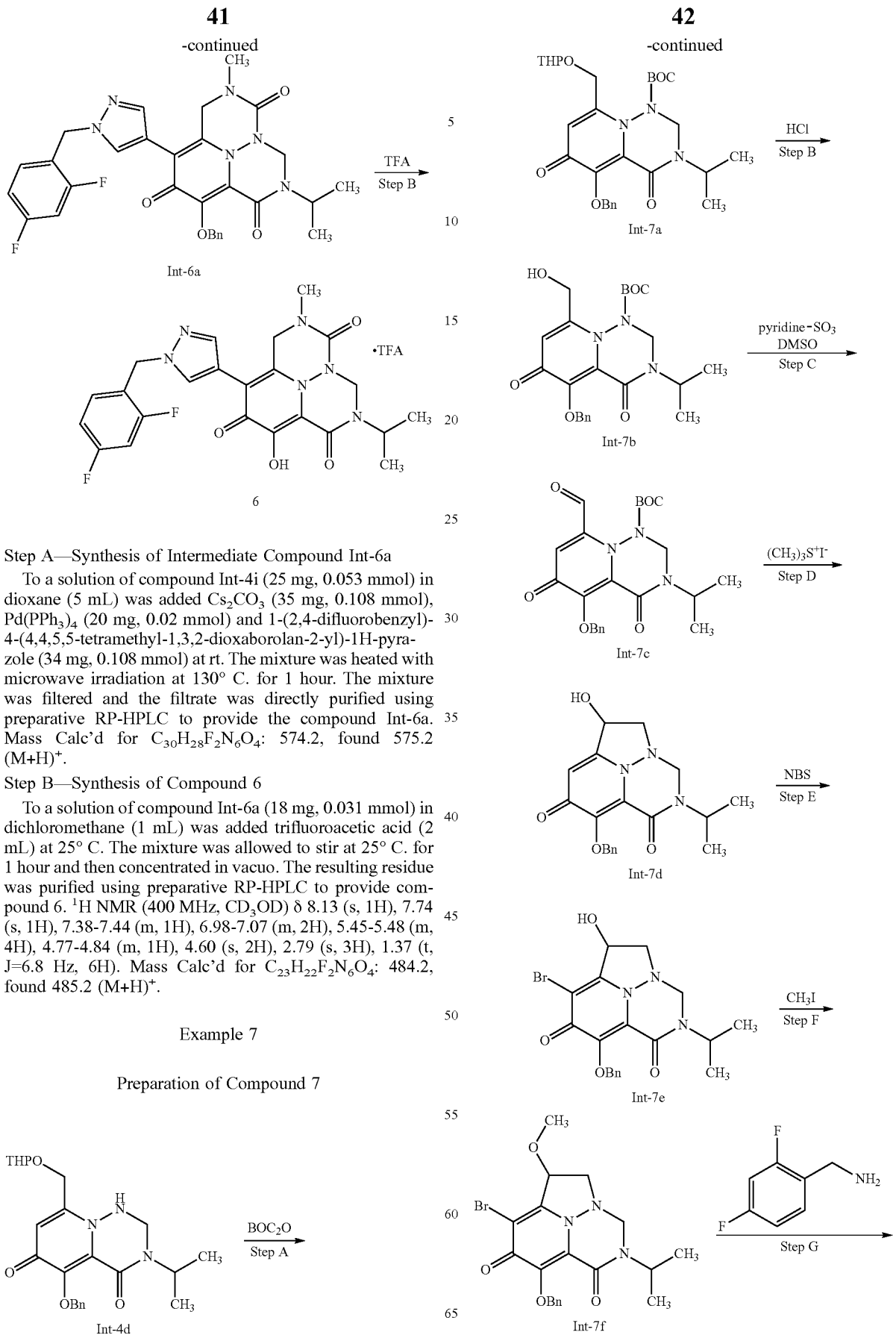

Step A—Synthesis of Intermediate Compound Int-6a

To a solution of compound Int-4i (25 mg, 0.053 mmol) in dioxane (5 mL) was added $Cs_2CO_3$ (35 mg, 0.108 mmol), $Pd(PPh_3)_4$ (20 mg, 0.02 mmol) and 1-(2,4-difluorobenzyl)-4-(4,4,5,5-tetramethyl-1,3,2-dioxaborolan-2-yl)-1H-pyrazole (34 mg, 0.108 mmol) at rt. The mixture was heated with microwave irradiation at 130° C. for 1 hour. The mixture was filtered and the filtrate was directly purified using preparative RP-HPLC to provide the compound Int-6a. Mass Calc'd for $C_{30}H_{28}F_2N_6O_4$: 574.2, found 575.2 $(M+H)^+$.

Step B—Synthesis of Compound 6

To a solution of compound Int-6a (18 mg, 0.031 mmol) in dichloromethane (1 mL) was added trifluoroacetic acid (2 mL) at 25° C. The mixture was allowed to stir at 25° C. for 1 hour and then concentrated in vacuo. The resulting residue was purified using preparative RP-HPLC to provide compound 6. $^1$H NMR (400 MHz, $CD_3OD$) δ 8.13 (s, 1H), 7.74 (s, 1H), 7.38-7.44 (m, 1H), 6.98-7.07 (m, 2H), 5.45-5.48 (m, 4H), 4.77-4.84 (m, 1H), 4.60 (s, 2H), 2.79 (s, 3H), 1.37 (t, J=6.8 Hz, 6H). Mass Calc'd for $C_{23}H_{22}F_2N_6O_4$: 484.2, found 485.2 $(M+H)^+$.

Example 7

Preparation of Compound 7

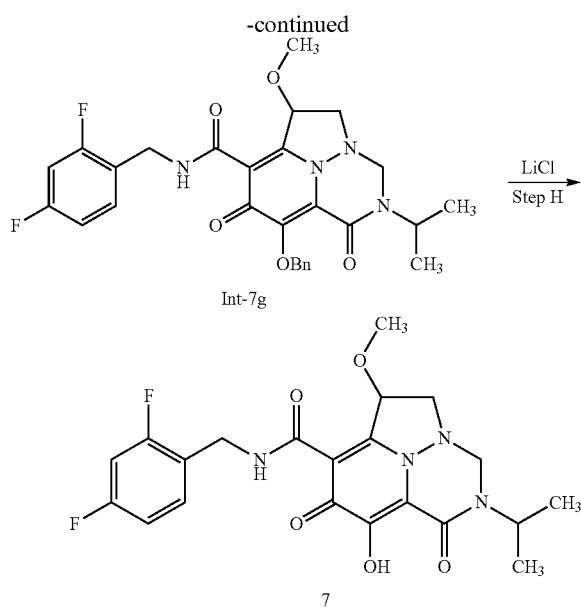

Int-7g

7

Step A—Synthesis of Intermediate Compound Int-7a

To a solution of Int-4d (900 mg, 2.105 mmol) in dichloromethane (50 mL) was added 4-dimethylaminopyridine (25.7 mg, 0.211 mmol) and di-tert-butyl dicarbonate (689 mg, 3.16 mmol). The mixture was allowed to stir at room temperature for 16 hours and then concentrated in vacuo. The resulting residue was purified using preparative TLC on silica gel (petroleum ether:ethyl acetate=1:1) to provide Int-7a. $^1$H NMR (400 MHz, CD$_3$OD) δ 7.47-7.48 (m, 2H), 7.30-7.31 (m, 3H), 6.66 (d, J=16.0 Hz, 1H), 5.25 (s, 2H), 4.71-4.73 (m, 5H), 4.42-4.57 (m, 1H), 3.78-3.83 (m, 1H), 3.52-3.54 (m, 1H), 1.57-1.87 (m, 6H), 1.45 (s, 9H), 1.20 (dd, J=6.8, 6.8 Hz, 6H).

Step B—Synthesis of Intermediate Compound Int-7b

A solution of Int-7a (450 mg, 0.855 mmol) in ethyl acetate (20 mL) was treated with a solution of HCl in ethyl acetate (4 M, 6 mL). The mixture was allowed to stir at 0° C. for 2 hours and then concentrated in vacuo. The resulting residue was purified using preparative TLC (100% ethyl acetate) to provide Int-7b. $^1$H NMR (400 MHz, CD$_3$OD) δ 7.46-7.48 (m, 2H), 7.30-7.31 (m, 3H), 6.67 (s, 1H), 5.16-5.34 (m, 2H), 4.60-4.68 (m, 3H), 1.45 (s, 9H), 1.20 (dd, J=6.8, 6.8 Hz, 6H).

Step C—Synthesis of Intermediate Compound Int-7c

To a solution of Int-7b (250 mg, 0.564 mmol) in dichloromethane (15 mL) was added N,N-diisopropylethylamine (947 mg, 7.33 mmol), dimethylsulfoxide (881 mg, 11.27 mmol) and pyridine-SO$_3$ (219 mg, 1.378 mmol). The mixture was allowed to stir at room temperature for 16 hours, washed with aqueous HCl (0.5 M), dried over anhydrous Na$_2$SO$_4$, filtered and the filtrate was concentrated in vacuo to provide the crude Int-7c, which was used without further purification. $^1$H NMR (400 MHz, CD$_3$OD) δ 7.46-7.48 (m, 2H), 7.30-7.31 (m, 3H), 6.78 (s, 1H), 5.16-5.19 (m, 2H), 4.56-4.61 (m, 2H), 1.43 (s, 9H), 1.24 (m, 6H).

Step D—Synthesis of Intermediate Compound Int-7d

To a solution of trimethylsulfonium iodide (285 mg, 1.812 mmol) in dimethylsulfoxide (6 mL) was added sodium hydride (54.4 mg, 2.265 mmol) and the mixture was allowed to stir at room temperature for 40 min. A solution of Int-7c (200 mg, 0.453 mmol) in dimethylsulfoxide (2 mL) was added to the mixture and stirred at room temperature for 30 min. The mixture was diluted with water (4 mL) at 0° C. and filtered. The filtrate was purified using prep-HPLC to provide Int-7d. $^1$H NMR (400 MHz, CD$_3$OD) δ 7.49-7.50 (m, 2H), 7.33-7.34 (m, 3H), 7.15 (s, 1H), 5.54 (t, J=13.2 Hz, 1H), 5.29 (s, 2H), 4.80-4.82 (m, 1H), 4.50-4.59 (m, 2H), 3.82-3.86 (m, 1H), 3.38-3.42 (m, 1H), 1.24 (d, J=6.4 Hz, 1H); Mass Calc'd for C$_{19}$H$_{21}$N$_3$O$_4$: 355.2, found 356.2 (M+H)$^+$.

Step E—Synthesis of Intermediate Compound Int-7e

To a solution of Int-7d (30 mg, 0.084 mmol) in acetonitrile (8 mL) was added N-bromosuccinimide (22.54 mg, 0.127 mmol). The mixture was allowed to stir at room temperature for 30 min, concentrated in vacuo and the resulting residue was purified using preparative TLC on silica gel (100% ethyl acetate) to provide Int-7e. $^1$H NMR (400 MHz, CD$_3$OD) δ 7.50-7.51 (m, 2H), 7.30-7.32 (m, 3H), 5.51 (t, J=13.2 Hz, 1H), 5.26 (dd, J=6.8, 6.8 Hz, 2H), 4.67-4.70 (m, 3H), 4.18-4.19 (m, 1H), 3.61-3.64 (m, 1H), 1.18-1.26 (m, 6H); Mass Calc'd for C$_{19}$H$_{20}$BrN$_3$O$_4$: 433.1, found 434.2 (M+H)$^+$.

Step F—Synthesis of Intermediate Compound Int-7f

To a solution of Int-7e (20 mg, 0.046 mmol) in N,N-dimethylformamide (3 mL) was added sodium hydride (1.105 mg, 0.046 mmol) at 0° C. The mixture was allowed to stir at 0° C. for 30 min, treated with iodomethane (6.54 mg, 0.046 mmol), stirred at 0° C. for 2 hours, quenched with water and extracted with ethyl acetate. The combined organic portions were dried over anhydrous Na$_2$SO$_4$, filtered, and the filtrate was concentrated in vacuo. The resulting residue was purified using preparative TLC on silica gel (100% ethyl acetate) to provide Int-7f. $^1$H NMR (400 MHz, CD$_3$OD) δ 7.48-7.50 (m, 2H), 7.28-7.30 (m, 3H), 5.51 (t, J=13.2 Hz, 1H), 5.17-5.25 (m, 2H), 4.04-4.12 (m, 3H), 3.83-3.86 (m, 1H), 3.52 (s, 3H), 1.16 (d, J=7.2 Hz, 6H); Mass Calc'd for C$_{20}$H$_{22}$BrN$_3$O$_4$: 447.1, found 448.2 (M+H)$^+$.

Step G—Synthesis of Intermediate Compound Int-7g

To a solution of Int-7f (20 mg, 0.045 mmol) in methanol (3 mL) and dimethylsulfoxide (1 mL) was added Pd(PPh$_3$)$_4$ (11.60 mg, 0.010 mmol), (2,4-difluorophenyl)methanamine (12.8 mg, 0.09 mmol) and N,N-diisopropylethylamine (5.6 mg, 0.05 mmol). The mixture was allowed to stir at 90° C. for 2 h under carbon monoxide (1 atm), filtered and the filtrate was concentrated in vacuo. The resulting residue was purified using preparative TLC (ethyl acetate) to provide Int-7g. $^1$H NMR (400 MHz, CD$_3$OD) 7.43-7.60 (m, 6H), 6.91-6.95 (m, 2H), 5.95 (d, J=4.2 Hz, 1H), 5.26 (dd, J=6.8, 6.8 Hz, 2H), 4.77-4.79 (m, 2H), 4.58-4.63 (m, 3H), 4.03-4.06 (m, 1H), 3.86-3.89 (m, 1H), 3.45 (s, 1H), 1.16-1.24 (m, 6H); Mass Calc'd for C$_{28}$H$_{28}$F$_2$N$_4$O$_5$: 538.2, found 539.3 (M+H)$^+$.

Step H—Synthesis of Compound 7

A solution of Int-7g (15 mg, 0.028 mmol) in N,N-dimethylformamide (3 mL) was treated with lithium chloride (11.8 mg, 0.28 mmol) at rt. The mixture was allowed to stir at 110° C. for 30 min, cooled to rt and directly purified using preparative RP-HPLC to provide compound 7. $^1$H NMR (400 MHz, CD$_3$OD) δ 7.45-7.46 (m, 1H), 6.95-6.98 (m, 2H), 5.98-6.00 (d, 1H), 5.10-5.20 (m, 1H), 4.63-4.66 (m, 2H), 4.29-4.32 (m, 3H), 3.94-3.97 (m, 1H), 3.49 (s, 3H), 3.30-3.40 (m, 2H), 1.24-1.35 (m, 6H); Mass Calc'd for C$_{21}$H$_{22}$F$_2$N$_4$O$_5$: 448.2, found 449.2 (M+H)$^+$.

Example 8
Preparation of Compound 8
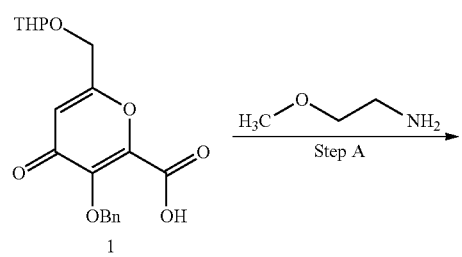
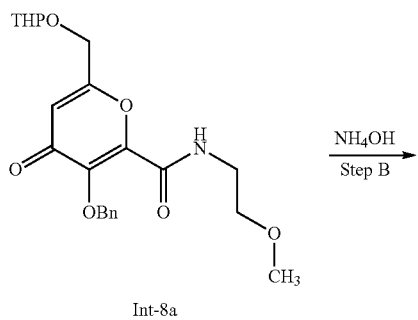
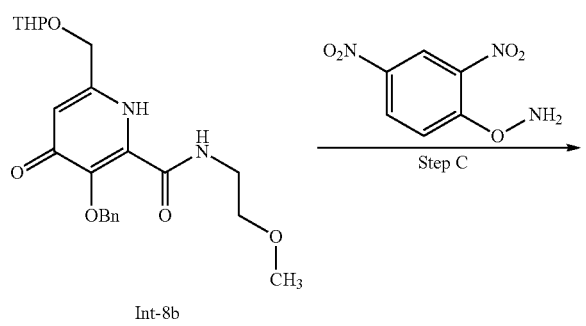
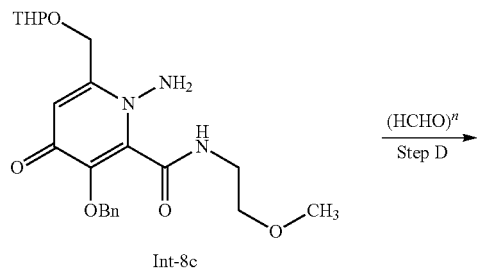
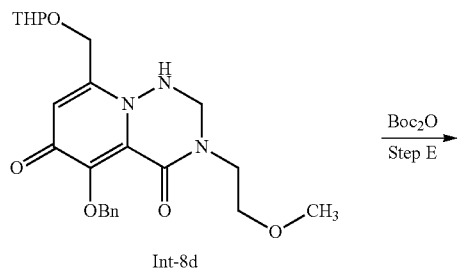
-continued
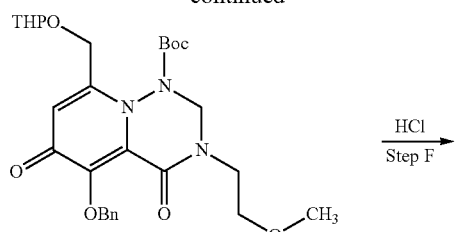
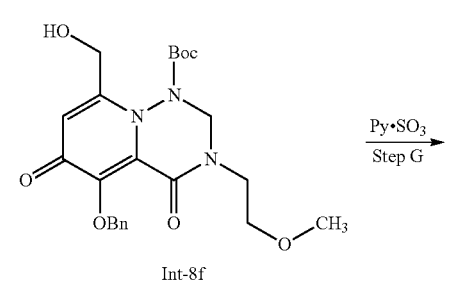
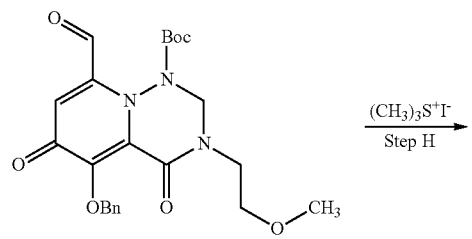
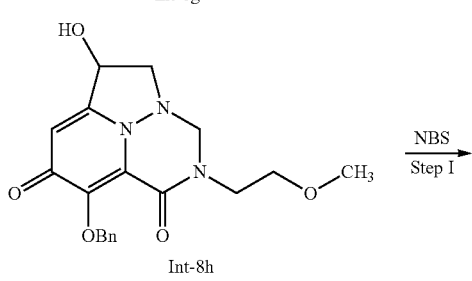
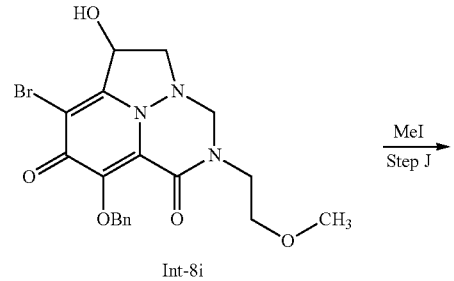
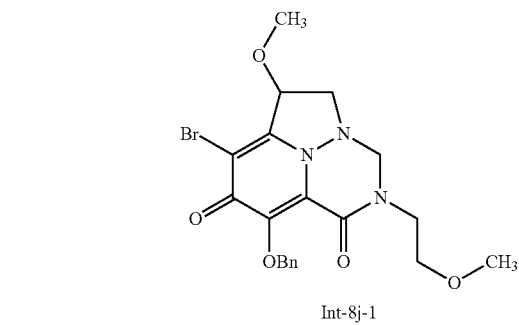

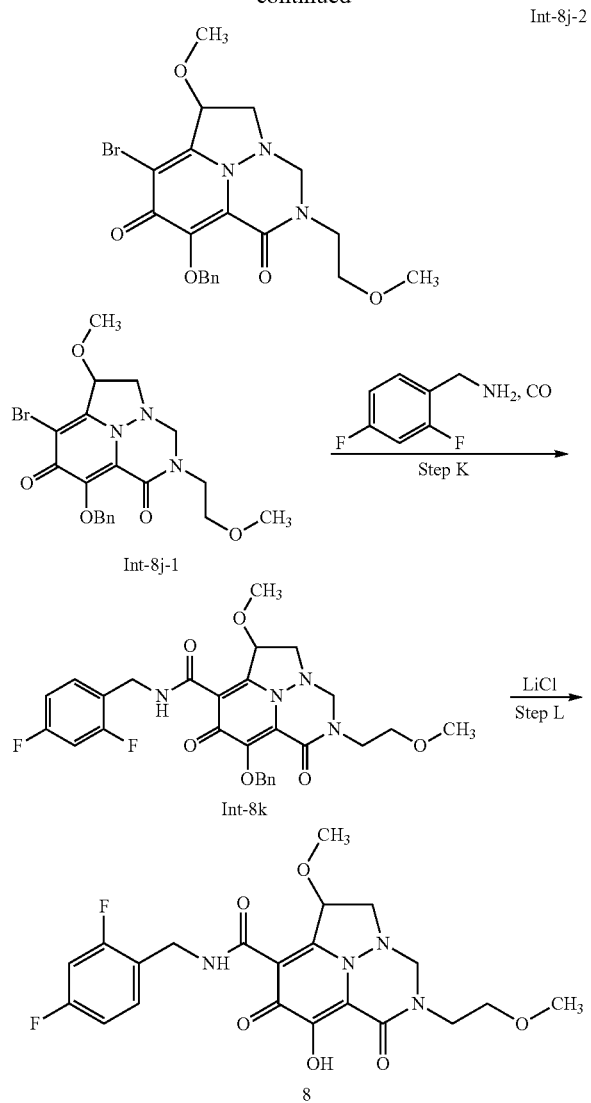

Step A—Synthesis of Intermediate Compound Int-8a

To a solution of compound 1 (72 g, 199.7 mmol), 2-methoxyethanamine (30 g, 398 mmol), HOAT (35.4 g, 259.7 mmol), HATU (98.78 g, 261.1 mmol) in N,N-dimethylformamide (500 mL) was added N,N-diisopropylethylamine (71.02 g, 600 mmol) at 0° C. The mixture was allowed to stir at 20° C. for 16 hours, diluted with water and extracted with ethyl acetate. The combined organic portions were washed with brine (150 mL), dried over anhydrous $Na_2SO_4$, filtered and the filtrate was concentrated in vacuo. The resulting residue was purified using column chromatography on silica gel (petroleum ether:ethyl acetate=1.5:1) to provide Int-8a. $^1$H NMR (400 MHz, $CD_3OD$) δ 8.09 (brs, 1H), 7.28-7.51 (m, 5H), 6.59 (s, 1H), 5.41 (s, 2H), 4.69-4.78 (m, 1H), 4.61 (d, J=15.3 Hz, 1H), 4.42 (d, J=15.3 Hz, 1H), 3.77-3.86 (m, 1H), 3.45-3.58 (m, 3H), 3.36-3.43 (m, 2H), 3.28 (s, 3H), 1.51-1.78 (m, 6H). Mass Calc'd for $C_{22}H_{27}NO_7$: 417.2, found 418.1 (M+H)$^+$.

Step B—Synthesis of Intermediate Compound Int-8b

A solution of Int-8a (24 g, 57.5 mmol) and ammonium hydroxide (28% aqueous, 77 mL) in ethanol (50 mL) was allowed to stir at 25° C. for 20 hours. The mixture was concentrated in vacuo to provide Int-8b, which was used without further purification. $^1$H NMR (400 MHz, $CDCl_3$) δ 8.60 (s, 1H), 7.23-7.52 (m, 5H), 6.29-6.43 (m, 1H), 5.49 (s, 2H), 4.35-4.77 (m, 4H), 3.93 (m, 1H), 3.39-3.69 (m, 4H), 3.18-3.36 (m, 3H), 1.54-1.92 (m, 6H). Mass Calc'd for $C_{22}H_{28}N_2O_6$: 416.2, found 417.2 (M+H)$^+$.

Step C—Synthesis of Intermediate Compound Int-8c

A solution of Int-8b (23 g, 45.2 mmol) and $K_2CO_3$ (12.50 g, 90 mmol) in N,N-dimethylformamide (200 mL) was added O-(2,4-dinitrophenyl)hydroxylamine (13.51 g, 67.8 mmol) in portions with stirring at 25° C. The mixture was allowed to stir at 25° C. for 26 hours. The progress of the reaction was monitored by TLC (ethyl acetate). The mixture was filtered and the filtrate was purified using preparative RP-HPLC (water with 0.05% $NH_4OH$/acetonitrile) to provide Int-8c. $^1$H NMR (400 MHz, $CDCl_3$) δ 10.15-10.35 (m, 1H), 8.59 (s, 1H), 7.20-7.48 (m, 5H), 6.36 (s, 1H), 5.47 (s, 2H), 4.45-4.69 (m, 3H), 3.90-3.99 (m, 1H), 3.36-3.64 (m, 4H), 3.21-3.34 (m, 3H), 1.47-1.86 (m, 6H). Mass Calc'd for $C_{22}H_{29}N_3O_6$: 431.2, found 432.3 (M+H)$^+$.

Step D—Synthesis of Intermediate Compound Int-8d

To a solution of Int-8c (12.5 g, 29.0 mmol) in acetic acid (10 mL) and tetrahydrofuran (100 mL) was added paraformaldehyde (0.869 g, 29.0 mmol). The mixture was allowed to stir at 80° C. for 18 hours. The mixture was concentrated in vacuo and the resulting residue was dissolved in dichloromethane, washed with saturated aqueous $NaHCO_3$ and brine, dried over $Na_2SO_4$, filtered and the filtrate was concentrated in vacuo. The resulting residue was purified using column chromatography on silica gel (ethyl acetate to ethyl acetate:methanol=9:1) to provide Int-8d. $^1$H NMR (400 MHz, $CD_3OD$) δ 7.48 (d, J=5.5 Hz, 2H), 7.29 (d, J=5.9 Hz, 3H), 6.65 (s, 1H), 5.37 (t, J=6.3 Hz, 1H), 5.23 (s, 2H), 4.48 (s, 2H), 3.73 (s, 2H), 3.49-3.62 (m, 3H), 3.34 (s, 3H), 3.18-3.24 (m, 1H), 2.88 (s, 2H), 1.47-1.86 (m, 6H). Mass Calc'd for $C_{23}H_{29}N_3O_6$: 443.2, found 444.2 (M+H)$^+$.

Step E—Synthesis of Intermediate Compound Int-8e

A solution of Int-8d (9 g, 20.3 mmol), triethylamine (8.49 mL, 60.9 mmol) and di-tert-butyl dicarbonate (9.42 mL, 40.6 mmol) in dichloromethane (100 mL) was treated with 4-dimethylaminopyridine (0.248 g, 2.029 mmol). The mixture was allowed to stir at 25° C. for 16 hours, concentrated in vacuo and the resulting residue was purified using column chromatography on silica gel (petroleum ether:ethyl acetate=1:1 to 1:2) to provide Int-8e. $^1$H NMR (400 MHz, $CD_3OD$) δ 7.20-7.57 (m, 5H), 6.63 (d, J=12.9 Hz, 1H), 5.10-5.36 (m, 3H), 4.84 (d, J=3.5 Hz, 1H), 4.67-4.73 (m, 1H), 4.53 (s, 1H), 3.99 (d, J=13.7 Hz, 1H), 3.51 (d, J=5.1 Hz, 2H), 3.42 (dd, J=6.26, 12.5 Hz, 1H), 3.29 (brs, 6H), 1.54-1.98 (m, 6H), 1.06-1.50 (m, 9H). Mass Calc'd for $C_{28}H_{37}N_3O_8$: 543.3, found 544.2 (M+H)$^+$.

Step F—Synthesis of Intermediate Compound Int-8f

To a solution of Int-8e (9 g, 16.56 mmol) in ethyl acetate (10 mL) was added a solution of HCl in ethyl acetate (4 M, 4.14 mL) at 0° C. The mixture was allowed to stir at 25° C. for 10 min and then concentrated in vacuo. The resulting residue was purified using column chromatography on silica gel (ethyl acetate:methanol=100:2) to provide Int-8f. $^1$H NMR (400 MHz, $CDCl_3$) δ 7.60 (d, J=6.4 Hz, 2H), 7.30-7.40 (m, 3H), 7.17 (s, 1H), 5.33 (d, J=9.2 Hz, 1H), 5.19 (d, J=9.2 Hz, 1H), 5.12 (d, J=11.2 Hz, 2H), 4.97 (s, 1H), 4.77 (d, J=14.8 Hz, 1H), 4.39 (d, J=14.8 Hz, 1H), 3.94 (d, J=12.8 Hz, 2H), 3.47 (s, 2H), 3.26-3.34 (m, 3H), 1.42 (s, 9H). Mass Calc'd for $C_{23}H_{29}N_3O_7$: 459.2, found 460.2 (M+H)$^+$.

Step G—Synthesis of Intermediate Compound Int-8g

A solution of Int-8f (9 g, 10.88 mmol), dimethylsulfoxide (15.44 mL, 217 mmol) and N,N-diisopropylethylamine (24.7 mL, 141.6 mmol) in dichloromethane (150 mL) was treated with sulfur trioxide pyridine complex (37.4 g, 235 mmol). The mixture was allowed to stir at 25° C. for 16 hours, diluted with dichloromethane, washed with aqueous HCl (1 N) and brine, dried over anhydrous $Na_2SO_4$, filtered and the filtrate was concentrated in vacuo to provide Int-8g, which was used without further purification. $^1$H NMR (400 MHz, $CDCl_3$) δ 9.81 (s, 1H), 7.52 (d, J=6.4 Hz, 2H), 7.21-7.32 (m, 3H), 6.81-6.88 (m, 1H), 5.50 (d, J=10.6 Hz, 1H), 5.24-5.36 (m, 2H), 4.79 (d, J=13.6 Hz, 1H), 4.19 (d, J=14.4 Hz, 1H), 3.43-3.53 (m, 3H), 3.26-3.31 (m, 3H), 1.35 (s, 9H). Mass Calc'd for $C_{23}H_{27}N_3O_7$: 457.2, found 458.2 $(M+H)^+$.

Step H—Synthesis of Intermediate Compound Int-8h

To a solution of trimethylsulfonium iodide (2140 mg, 10.48 mmol) in N,N-dimethylformamide (8 mL) was added NaH (840 mg, 21 mmol) and the mixture was stirred under a nitrogen atmosphere at 25° C. for 2 hours. The mixture was treated dropwise with a solution of Int-8g (1.2 g, 2.62 mmol) in N,N-dimethylformamide (15 mL) at 0° C. and the mixture was allowed to stir at 0° C. for 10 min under a nitrogen atmosphere. The mixture was diluted with water (4 mL) at 0° C. and filtered. The filtrate was directly purified using preparative RP-HPLC to provide Int-8h. $^1$H NMR (400 MHz, $CD_3OD$) δ 7.48 (d, J=5.1 Hz, 2H), 7.29 (d, J=5.6 Hz, 3H), 6.65 (s, 1H), 5.37 (t, J=6.4 Hz, 1H), 5.23 (s, 2H), 4.48 (s, 2H), 3.73 (s, 2H), 3.62 (s, 1H), 3.55 (t, J=4.8 Hz, 2H), 3.34 (s, 3H), 3.23 (s, 1H). Mass Calc'd for $C_{19}H_{21}N_3O_5$: 371.1, found 372.2 $(M+H)^+$.

Step I—Synthesis of Intermediate Compound Int-8i

N-bromosuccinimide (144 mg, 0.808 mmol) was added to a solution of Int-8h (200 mg, 0.539 mmol) in acetonitrile (10 mL). The mixture was allowed to stir at 25° C. for 3 hours and then concentrated in vacuo. The resulting residue was purified using preparative TLC on silica gel (ethyl acetate:methanol=8:1) to provide Int-8i. $^1$H NMR: (400 MHz, $CD_3OD$) δ 7.49-7.51 (m, 2H), 7.29-7.30 (m, 3H), 5.47-5.49 (m, 1H), 5.28 (d, J=10.4 Hz 1H), 5.20 (d, J=10.4 Hz 1H), 4.63-4.66 (m, 1H), 4.37-4.40 (m, 1H), 3.64-3.84 (m, 1H), 3.56-3.63 (m, 4H), 3.32-3.34 (m, 4H). Mass Calc'd for $C_{19}H_{20}BrN_3O_5$: 449.1, 451.1, found 450.1, 452.1 $(M+H)^+$.

Step J—Synthesis of Intermediate Compound Int-8j-1 (Enantiomer A) and Int-8j-2 (Enantiomer B)

A solution of Int-8i (100 mg, 0.222 mmol) in N,N-dimethylformamide (5 mL) was treated with sodium hydride (6.92 mg, 0.289 mmol) at 0° C. After stirring at 0° C. for 30 min, iodomethane (47.3 mg, 0.332 mmol) was added. The reaction mixture was allowed to stir at 0° C. for 10 min, diluted with water and extracted with ethyl acetate. The combined organic portions were dried over anhydrous $Na_2SO_4$, filtered and the filtrate was concentrated in vacuo. The resulting residue was purified using preparative TLC on silica gel (100% ethyl acetate) to provide Int-8j as the racemate. $^1$H NMR (400 MHz, $CD_3OD$) δ 7.52 (d, J=6.4 Hz, 2H), 7.25-7.36 (m, 3H), 5.25-5.35 (m, 2H), 5.21 (d, J=10.4 Hz, 1H), 4.62-4.73 (m, 2H), 4.39 (d, J=10.4 Hz, 1H), 3.79-3.96 (m, 3H), 3.50-3.64 (m, 5H), 3.36 (s, 3H). Mass Calc'd for $C_{20}H_{22}BrN_3O_5$: 463.1, 465.1, found 464.0, 466.0 $(M+H)^+$.

Resolution to the enantiomers was accomplished with SFC (AD, 250 mm×30 mm, 10 μm, $SC-CO_2$/methanol=55/45 at 80 mL/min) to provide Int-8j-1 (enantiomer A) and Int-8j-1 (enantiomer B).

Step K—Synthesis of Intermediate Compound Int-8k

To a solution of Int-8j-1 (enantiomer A) (20 mg, 0.043 mmol), (2,4-difluorophenyl)methanamine (18.50 mg, 0.129 mmol) and N,N-diisopropylethylamine (0.038 mL, 0.215 mmol) in dimethylsulfoxide (2 mL) and methanol (2 mL) was treated with $Pd(Ph_3P)_4$ (24.89 mg, 0.022 mmol). The mixture was allowed to stir at 89° C. under carbon monoxide (1 atm) for 3 hours. The mixture was cooled to room temperature, diluted with aqueous HCl (1N, 5 mL) and extracted with ethyl acetate. The combined organic portions were washed with brine, dried over anhydrous $Na_2SO_4$, filtered and the filtrate was concentrated in vacuo. The resulting residue was purified using preparative TLC on silica gel (100% ethyl acetate) to provide Int-8k. $^1$H NMR: (400 MHz, $CD_3OD$) δ 7.52-7.59 (m, 2H), 7.45-7.52 (m, 1H), 7.30-7.38 (m, 3H), 6.94-7.04 (m, 2H), 5.95 (d, J=5.6 Hz, 1H), 5.20-5.35 (m, 2H), 4.74 (d, J=11.2 Hz, 1H), 4.65 (d, J=7.2 Hz, 2H), 4.35-4.39 (m, 1H), 3.84-3.94 (m, 2H), 3.61-3.69 (m, 1H), 3.57-3.61 (m, 2H), 3.48-3.52 (m, 3H), 3.38 (s, 3H), 3.12 (dd, J=5.2, 11.0 Hz, 1H). Mass Calc'd for $C_{28}H_{28}F_2N_4O_6$: 554.2, found 555.2 $(M+H)^+$.

Step L—Synthesis of Compound 8

A solution of Int-8k (5 mg, 0.009 mmol) and lithium chloride (3.82 mg, 0.09 mmol) in N,N-dimethylformamide (2 mL) was allowed to stir at 80° C. for 5 hours. The mixture was cooled to room temperature, filtered and the filtrate was directly purified using preparative RP-HPLC to provide compound 8. $^1$H NMR 0361628-0112-1: (400 MHz, $CD_3OD$) δ 7.36-7.48 (m, 1H), 6.83-7.01 (m, 2H), 5.91 (d, J=4.4 Hz, 1H), 4.44-4.70 (m, 3H), 3.88 (d, J=10.4 Hz, 2H), 3.52-3.75 (m, 3H), 3.30-3.51 (m, 6H), 3.09-3.27 (m, 2H). Mass Calc'd for $C_{21}H_{22}F_2N_4O_6$: 464.2, found 465.2 $(M+H)^+$.

Example 9

Preparation of Compound 9

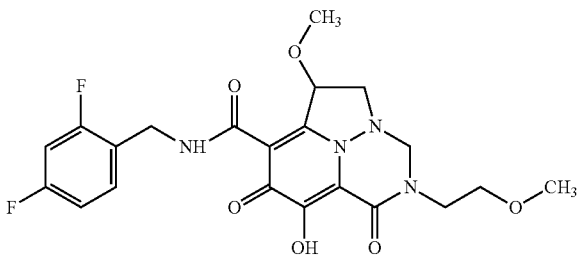

Compound 9 was prepared from Int-8j-2 (enantiomer B) using the methods described in Example 8.

$^1$H NMR (400 MHz, $CD_3OD$) δ 7.36-7.49 (m, 1H), 6.82-7.02 (m, 2H), 5.90 (d, J=4.4 Hz, 1H), 4.83 (s, 1H), 4.45-4.71 (m, 3H), 3.88 (d, J=10.4 Hz, 2H), 3.50-3.73 (m, 3H), 3.29-3.49 (m, 6H), 3.09-3.19 (m, 1H). Mass Calc'd for $C_{21}H_{22}F_2N_4O_6$: 464.2, found 465.2 $(M+H)^+$.

The following compounds of the present invention were prepared using the methods described in Examples 8 and 9 and substituting the appropriate reactants and/or reagents.

| Compound | Structure | Stereochemistry | Exact Mass [M + H]⁺ |
|---|---|---|---|
| 10 | 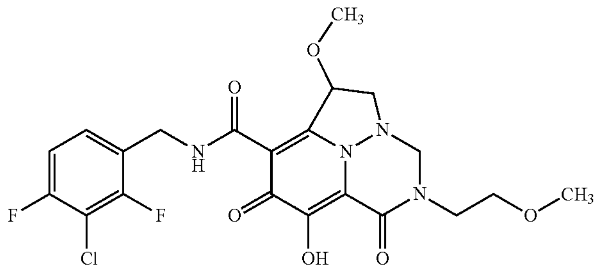 [SMILES: COCCN1CN2CC(OC)c3c(C(=O)NCc4ccc(F)c(Cl)c4F)c(=O)c(O)c(n32)C1=O] | enantiomer A | Calc'd 499.1, found 499.1 |
| 11 | 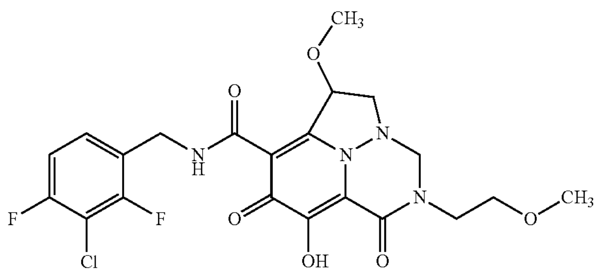 [SMILES: COCCN1CN2CC(OC)c3c(C(=O)NCc4ccc(F)c(Cl)c4F)c(=O)c(O)c(n32)C1=O] | enantiomer B | Calc'd 499.1, found 499.1 |
| 12 | 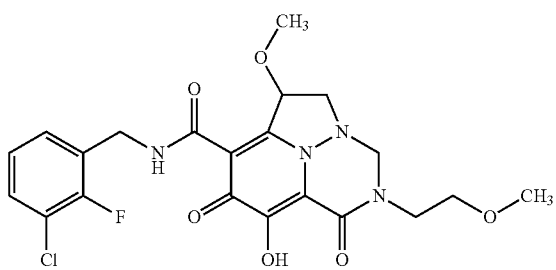 [SMILES: COCCN1CN2CC(OC)c3c(C(=O)NCc4cccc(Cl)c4F)c(=O)c(O)c(n32)C1=O] | enantiomer A | Calc'd 481.1, found 481.1 |
| 13 | 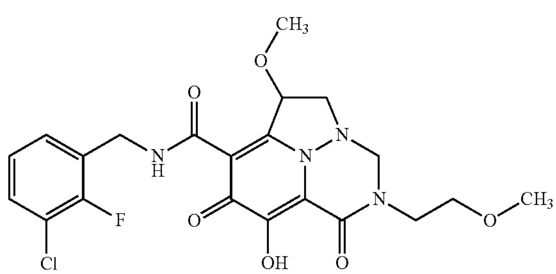 [SMILES: COCCN1CN2CC(OC)c3c(C(=O)NCc4cccc(Cl)c4F)c(=O)c(O)c(n32)C1=O] | enantiomer B | Calc'd 481.1, found 481.1 |
| 14 | 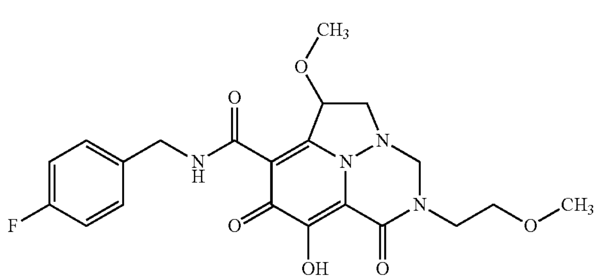 [SMILES: COCCN1CN2CC(OC)c3c(C(=O)NCc4ccc(F)cc4)c(=O)c(O)c(n32)C1=O] | enantiomer A | Calc'd 447.2, found 447.2 |

| Compound | Structure | Stereochemistry | Exact Mass [M + H]+ |
|---|---|---|---|
| 15 | 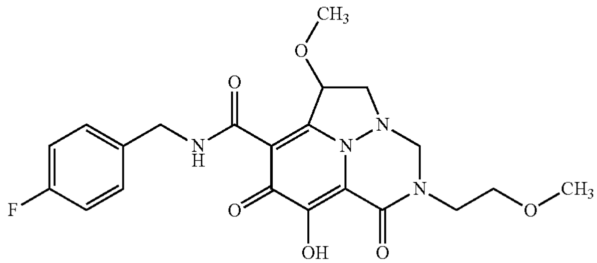 [SMILES: COCCN1CN2CC(OC)c3c(C(=O)NCc4ccc(F)cc4)c(=O)c(O)c(n32)C1=O] | enantiomer B | Calc'd 447.2, found 447.2 |
| 16 | 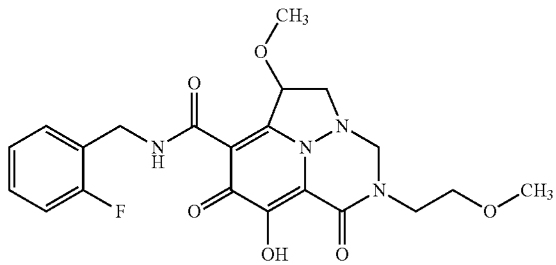 [SMILES: COCCN1CN2CC(OC)c3c(C(=O)NCc4ccccc4F)c(=O)c(O)c(n32)C1=O] | enantiomer B | Calc'd 447.2, found 447.2 |

| Compound # | ¹H NMR |
|---|---|
| 10 | ¹H NMR (400 MHz, CD₃OD) δ 7.35-7.41 (m, 1H), 7.06-7.10 (m, 1H), 5.92 (d, J = 5.2 Hz, 1H), 4.50-4.67 (m, 3H), 3.89 (d, J = 11.2 Hz, 2H), 3.59-3.70 (m, 3H), 3.45 (s, 3H), 3.36 (s, 3H), 3.15-3.18 (m, 2H) |
| 11 | ¹H NMR (400 MHz, CD₃OD) δ 7.35-7.41 (m, 1H), 7.06-7.10 (m, 1H), 5.91 (d, J = 5.2 Hz, 1H), 4.50-4.70 (m, 3H), 3.90 (d, J = 11.2 Hz, 2H), 3.59-3.67 (m, 3H), 3.45 (s, 3H), 3.35 (s, 3H), 3.16-3.18 (m, 2H) |
| 12 | ¹H NMR (400 MHz, CD₃OD) δ 7.33-7.36 (m, 2H), 7.11-7.12 (m, 1H), 5.93 (d, J = 4.40 Hz, 1H), 4.48-4.66 (m, 3H), 3.88 (d, J = 11.2 Hz, 2H), 3.55-3.62 (m, 3H), 3.45 (s, 3H), 3.34 (s, 3H), 3.11-3.13 (m, 2H) |
| 13 | ¹H NMR (400 MHz, CD₃OD) δ 7.31-7.38 (m, 2H), 7.09-7.13 (m, 1H), 5.92 (d, J = 4.40 Hz, 1H), 4.49-4.73 (m, 3H), 3.88 (d, J = 11.2 Hz, 2H), 3.60-3.68 (m, 3H), 3.44 (s, 3H), 3.34 (s, 3H), 3.12-3.16 (m, 2H) |
| 14 | ¹H NMR (400 MHz, CD₃OD) δ 7.34-7.38 (m, 2H), 7.01-7.06 (m, 2H), 5.94 (d, J = 5.2 Hz, 1H), 4.52-4.58 (m, 3H), 3.89 (d, J = 10.56 Hz, 2H), 3.60-3.70 (m, 3H), 3.46 (s, 3H), 3.35 (s, 3H), 3.13-3.18 (m, 2H) |
| 15 | ¹H NMR (400 MHz, CD₃OD) δ 7.34-7.37 (m, 2H), 7.01-7.05 (m, 2H), 5.91 (d, J = 5.2 Hz, 1H), 4.49-4.61 (m, 3H), 3.88 (d, J = 8 Hz, 2H), 3.52-3.75 (m, 3H), 3.45 (s, 3H), 3.34 (s, 3H), 3.12-3.17 (m, 2H) |
| 16 | ¹H NMR (400 MHz, CD₃OD) δ 7.39-7.43 (m, 1H), 7.28-7.21 (m, 1H), 7.10-7.16 (m, 2H), 5.95 (d, J = 4.8 Hz, 1H), 4.51-4.72 (m, 3H), 3.88 (d, J = 10.8 Hz, 2H), 3.62-3.70 (m, 3H), 3.47 (s, 3H), 3.36 (s, 3H), 3.15-3.157 (m, 2H) |

Example 10

Preparation of Compound 17

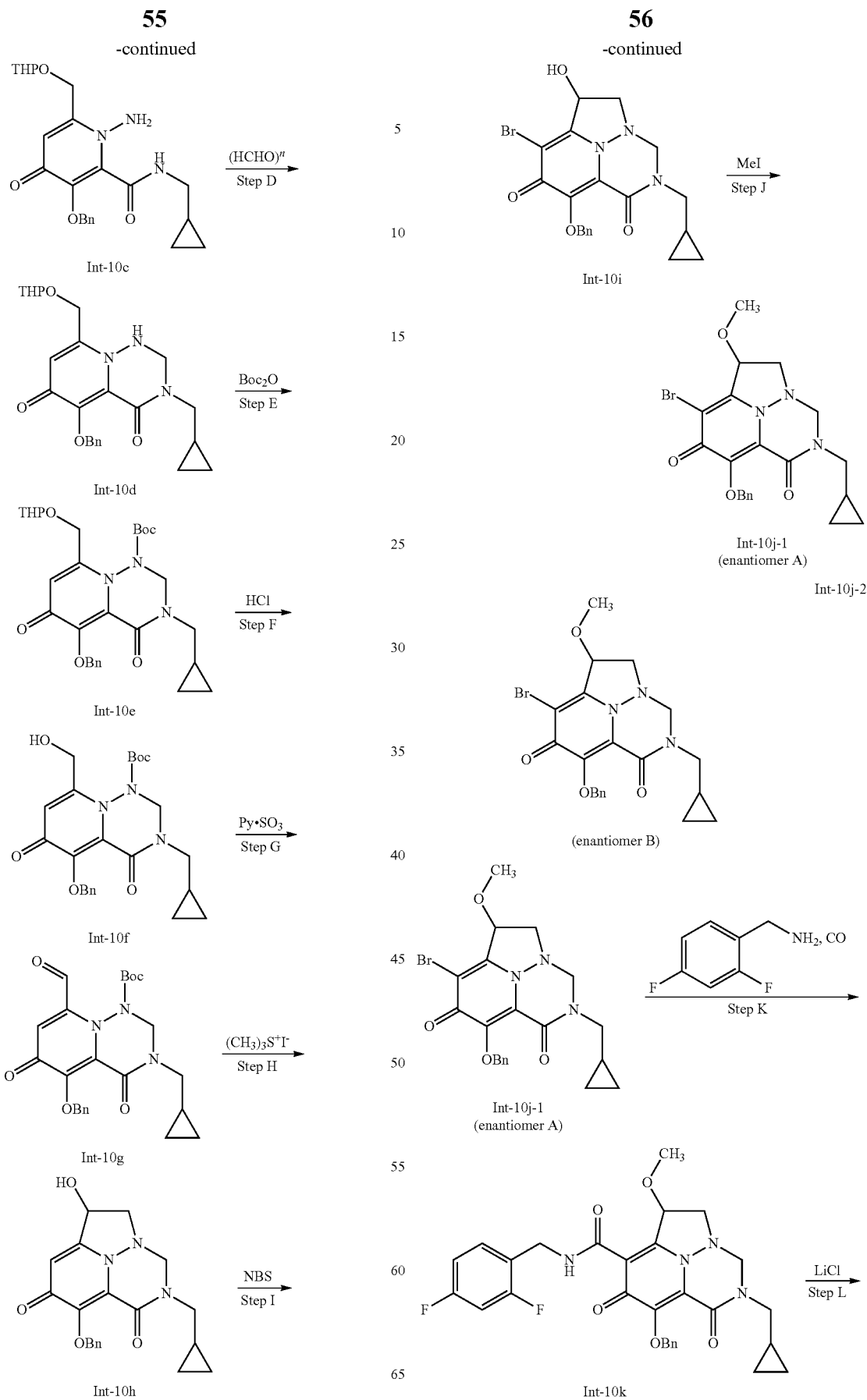

-continued

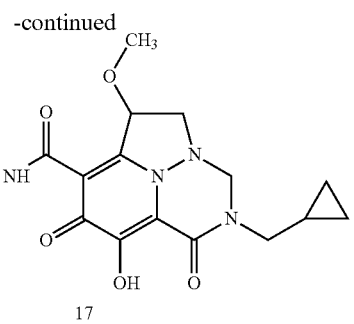

17

Step A—Synthesis of Intermediate Compound Int-10a

To a solution of compound 1 (15 g, 41.6 mmol) in N,N-dimethylformamide (200 mL) was added 6-chlorobenzotriazole-1-yl-oxy-tris-pyrrolidinophosphonium hexafluorophosphate (34.6 g, 62.4 mmol), N,N-diisopropylethylamine (10.76 g, 83 mmol) and cyclopropylmethanamine (5.92 g, 83 mmol), the mixture was allowed to stir at 20° C. for 16 hours. Water (100 mL) was added and the mixture was extracted with ethyl acetate. The combined organic portions were washed with brine (100 mL), dried over anhydrous $Na_2SO_4$, filtered and the filtrate was concentrated in vacuo. The resulting residue was purified using column chromatography on silica gel (petroleum ether/ethyl acetate=5:1) to provide compound Int-10a. $^1$H NMR (400 MHz, $CD_3OD$) δ 7.45-7.46 (m, 2H), 7.36-7.37 (m, 2H), 6.58 (s, 1H), 5.36 (s, 2H), 4.75-4.77 (m, 1H), 4.60 (d, J=16 Hz, 1H), 4.47 (d, J=16 Hz, 1H), 3.83-3.89 (m, 1H), 3.53-3.56 (m, 1H), 3.33-3.37 (m, 2H), 1.57-1.76 (m, 6H), 1.12-1.14 (m, 1H), 0.59-0.60 (m, 2H), 0.36-0.37 (m, 2H). Mass Calc'd for $C_{23}H_{27}NO_6$: 413.2, found 414.2 (M+H)$^+$.

Step B—Synthesis of Intermediate Compound Int-10b

A solution of compound Int-10a (8 g, 19.35 mmol) and ammonium hydroxide (28% aqueous, 60 mL) in ethanol (30 mL) was allowed to stir at 22° C. for 20 hours. The mixture was concentrated in vacuo to provide crude compound Int-10b, which was used without further purification. $^1$H NMR (400 MHz, $CD_3OD$) δ 7.31-7.32 (m, 2H), 7.21-7.22 (m, 3H), 6.44 (s, 1H), 5.28 (s, 2H), 4.42-4.59 (m, 3H), 3.79-3.81 (m, 1H), 3.41-3.44 (m, 1H), 2.97-2.99 (m, 2H), 1.45-1.65 (m, 6H), 0.65-0.75 (m, 1H), 0.28-0.37 (m, 2H), 0.09-0.10 (m, 2H). Mass Calc'd for $C_{23}H_{28}N_2O_5$: 412.2, found 413.2 (M+H)$^+$.

Step C—Synthesis of Intermediate Compound Int-10c

To a solution of Int-10b (3 g, 7.3 mmol) and $K_2CO_3$ (3.0 g, 21.8 mmol) in N,N-dimethylformamide (50 mL) was added O-(2,4-dinitrophenyl)hydroxylamine (2.2 g, 10.9 mmol) in portions with stirring at 25° C. The mixture was allowed to stir at 25° C. for 16 hours. The mixture was filtered and the filtrate was purified using preparative RP-HPLC (water with 0.05% $NH_4OH$/acetonitrile) to provide Int-10c. $^1$H NMR (400 MHz, $CD_3OD$) δ 7.11-7.14 (m, 2H), 7.22-7.24 (m, 3H), 6.45 (s, 1H), 4.94 (s, 2H), 4.43-4.57 (m, 3H), 3.64-3.68 (m, 1H), 3.35-3.38 (m, 1H), 2.96-2.97 (m, 2H), 1.37-1.68 (m, 6H), 0.71-0.75 (m, 1H), 0.22-0.24 (m, 2H), 0.09-0.10 (m, 2H). Mass Calc'd for $C_{23}H_{29}N_3O_5$: 427.2, found 428.2 (M+H)$^+$.

Step D—Synthesis of Intermediate Compound Int-10d

To a solution of Int-10c (4 g, 3.96 mmol) in acetic acid (2 mL) and tetrahydrofuran (40 mL) was added paraformaldehyde (0.309 g, 10.3 mmol). The mixture was allowed to stir at 80° C. for 18 hours. The mixture was concentrated in vacuo and the resulting residue was dissolved in dichloromethane (50 mL), washed with $NaHCO_3$, brine, dried over anhydrous $Na_2SO_4$, filtered and the filtrate was concentrated in vacuo give Int-10d which was used without further purification. Mass Calc'd for $C_{24}H_{29}N_3O_5$: 439.2, found 440.2 (M+H)$^+$.

Step E—Synthesis of Intermediate Compound Int-10e

To a solution of Int-10d (3.5 mg, 7.9 mmol), triethylamine (2.22 mL, 15.9 mmol) and di-t-butyl dicarbonate (3.70 mL, 15.93 mmol) in dichloromethane (100 mL) was added 4-dimethylaminopyridine (0.097 g, 0.796 mmol). The mixture was allowed to stir at 20° C. for 16 hours. The mixture was concentrated in vacuo and the resulting residue was purified using column chromatography on silica gel (petroleum ether:ethyl acetate=1:1 to 1:2) to provide Int-10e. $^1$H NMR (400 MHz, $CD_3OD$) δ 7.47-7.48 (m, 2H), 7.29-7.30 (m, 3H), 6.64 (d, J=14.4 Hz, 1H), 5.18-5.42 (m, 3H), 4.42-4.73 (m, 5H), 3.78-3.80 (m, 1H), 3.50-3.55 (m, 2H), 3.19-2.21 (m, 1H), 1.57-1.77 (m, 6H), 1.45 (s, 1H), 1.05-1.09 (m, 1H), 0.54-0.61 (m, 2H), 0.34-0.35 (m, 2H). Mass Calc'd for $C_{29}H_{37}N_3O_7$: 539.3, found 540.1 (M+H)$^+$.

Step F—Synthesis of Intermediate Compound Int-10f

To a solution of Int-10e (3.2 g, 5.93 mmol) in ethyl acetate (30 mL) was added a solution of HCl in ethyl acetate (4 M, 4 mL) at 0° C. The mixture was allowed to stir at 20° C. for 10 min. The mixture was concentrated in vacuo and the resulting residue was purified using column chromatography on silica gel (ethyl acetate:methanol=100:2) to provide Int-10f. $^1$H NMR (400 MHz, $CD_3OD$) δ 7.12-7.13 (m, 2H), 6.95-6.96 (m, 3H), 6.52 (s, 1H), 5.08 (d, J=14 Hz, 1H), 4.92 (d, J=10 Hz, 1H), 4.86 (d, J=10 Hz, 2H), 4.30 (d, J=16 Hz, 1H), 4.10 (d, J=16 Hz, 1H), 3.18-3.23 (m, 1H), 2.98-3.10 (m, 2H), 2.83-2.88 (m, 1H), 1.11 (s, 9H). 0.65-0.75 (m, 1H), 0.20-0.27 (m, 2H), 0.05-0.10 (m, 2H). Mass Calc'd for $C_{24}H_{29}N_3O_6$: 455.2, found 456.2 (M+H)$^+$.

Step G—Synthesis of Intermediate Compound Int-10g

To a solution of Int-10f (2.2 g, 4.83 mmol), dimethylsulfoxide (6.86 mL, 97 mmol) and N,N-diisopropylethylamine (10.97 mL, 62.8 mmol) in dichloromethane (50 mL) was added sulfur trioxide pyridine complex (9.22 g, 58 mmol). The mixture was allowed to stir at 20° C. for 16 hours. The mixture was diluted with dichloromethane (150 mL). The organic phases were washed with aqueous HCl (1 N, 3×25 mL) and brine, dried over anhydrous $Na_2SO_4$, filtered and the filtrate was concentrated in vacuo to provide Int-10g which was used without further purification. $^1$H NMR (400 MHz, $CDCl_3$) δ 9.54 (s, 1H), 7.23-7.25 (m, 2H), 6.96-7.00 (m, 3H), 6.58 (s, 1H), 5.10-5.23 (m, 2H), 4.36-4.49 (m, 2H), 3.29-3.36 (m, 1H), 2.86-2.92 (m, 1H), 1.07 (s, 9H), 0.65-0.75 (m, 1H), 0.26-0.30 (m, 2H), 0.10-0.16 (m, 2H). Mass Calc'd for $C_{24}H_{27}N_3O_6$: 453.2, found 454.2 (M+H)$^+$.

Step H—Synthesis of Intermediate Compound Int-10h

A solution of trimethylsulfonium iodide (360 mg, 1.76 mmol) in N,N-dimethylformamide (8 mL) was treated with NaH (152 mg, 3.79 mmol) and the mixture was stirred under nitrogen atmosphere at 20° C. for 1.5 hours. A solution of Int-10g (200 mg, 0.441 mmol) in N,N-dimethylformamide (12 mL) was added dropwise to the mixture at 20° C. and the mixture was allowed to stir at 20° C. for 30 min under a nitrogen atmosphere. The mixture was diluted with water (2 mL) at 0° C. and filtered. The filtrate was directly purified using preparative RP-HPLC to provide Int-10h. $^1$H NMR (400 MHz, $CD_3OD$) δ 7.16-7.17 (m, 2H), 6.96-7.00 (m, 3H), 6.84 (s, 1H), 5.20 (t, J=12.4 Hz, 1H), 4.94 (s, 2H), 4.34 (s, 1H), 3.48-3.50 (m, 1H), 3.00-3.16 (m, 3H), 0.70-0.78 (m, 1H), 0.22-0.27 (m, 2H), 0.14-0.26 (m, 2H). Mass Calc'd for $C_{20}H_{21}N_3O_4$: 367.2, found 368.2 (M+H)$^+$.

Step I—Synthesis of Intermediate Compound Int-10i

N-bromosuccinimide (145 mg, 0.817 mmol) was added to a solution of Int-10h (200 mg, 0.554 mmol) in acetonitrile (5 mL). The mixture was allowed to stir at 25° C. for 20 minutes. The mixture was concentrated in vacuo and the resulting residue was purified using preparative TLC on silica gel (ethyl acetate:methanol=14:1) to provide Int-10i. $^1$H NMR (400 MHz, CD$_3$OD) δ 7.54-7.56 (m, 2H), 7.31-7.35 (m, 3H), 5.51-5.54 (m, 1H), 5.31 (d, J=10 Hz, 1H), 5.24 (d, J=10.4 Hz, 1H), 4.76-4.76 (m, 1H), 4.44-4.46 (m, 1H), 3.55-3.62 (m, 2H), 3.36-3.40 (m, 2H), 1.12-1.14 (m, 1H), 0.57-0.61 (m, 2H), 0.35-0.38 (m, 2H). Mass Calc'd for C$_{20}$H$_{20}$BrN$_3$O$_4$: 445.1, found 446.1 (M+H)$^+$.

Step J—Synthesis of Intermediate Compound Int-10j-1 (Enantiomer A) and Int-10j-2 (Enantiomer B)

To a solution of Int-10i (142 mg, 0.318 mmol) in N,N-dimethylformamide (5 mL) was added sodium hydride (25.5 mg, 0.636 mmol) at 25° C. After stirring at 25° C. for 2 min, iodomethane (90 mg, 0.636 mmol) was added. The reaction mixture was allowed to stir at 25° C. for 5 min, and then diluted with water (5 mL) and extracted with ethyl acetate. The combined organic portions were dried over anhydrous Na$_2$SO$_4$, filtered and the filtrate was concentrated in vacuo. The resulting residue was purified using preparative TLC on silica gel (ethyl acetate:methanol=12:1) to provide Int-10j as the racemate. $^1$H NMR (400 MHz, CD$_3$OD) δ 7.54 (d, J=6 Hz, 2H), 7.32-7.34 (m, 3H), 5.22-5.35 (m, 3H), 4.78 (d, J=10.4 Hz, 1H), 4.43 (d, J=10.4 Hz, 1H), 3.85-3.88 (m, 1H), 3.55-3.62 (m, 4H), 3.36-3.38 (m, 2H), 1.12-1.14 (m, 1H), 0.57-0.62 (m, 2H), 0.35-0.37 (m, 2H). Mass Calc'd for C$_{21}$H$_{22}$BrN$_3$O$_4$: 459.1, found 460.0 (M+H)$^+$. Resolution was accomplished with SFC (AD, 250 mm×30 mm, 10 um, SC—CO$_2$/methanol 60/40 at 80 mL/min) to provide Int-10j-1 (enantiomer A) and Int-10j-2 (enantiomer B).

Step K—Synthesis of Intermediate Compound Int-10k

To a solution of compound Int-10j-1 (14 mg, 0.030 mmol), (2,4-difluorophenyl)methanamine (8.71 mg, 0.061 mmol) and N,N-diisopropylethylamine (0.010 mL, 0.061 mmol) in dimethylsulfoxide (2 mL) and methanol (2 mL) was added Pd(Ph$_3$P)$_4$ (3.51 mg, 3.04 mmol). The mixture was allowed to stir at 90° C. under carbon monoxide (1 atm) for 3 hours. The mixture was cooled to room temperature, diluted with aqueous HCl (1 N, 4 mL) and extracted with ethyl acetate. The combined organic portions were washed with brine, dried over anhydrous Na$_2$SO$_4$, filtered and the filtrate was concentrated in vacuo. The crude was purified using preparative TLC on silica gel (100% ethyl acetate) to provide Int-10k. $^1$H NMR (400 MHz, CD$_3$OD) δ 7.29-7.52 (m, 6H), 6.95-6.97 (m, 2H), 5.95 (d, J=4.8 Hz, 1H), 5.19-5.32 (m, 2H), 4.60-4.64 (m, 3H), 4.33-4.36 (m, 1H), 3.62-3.89 (m, 2H), 3.57-3.62 (m, 2H), 3.47 (s, 3H), 0.73-0.75 (m, 1H), 0.56-0.58 (m, 2H), 0.35-0.37 (m, 2H). Mass Calc'd for C$_{29}$H$_{28}$F$_2$N$_4$O$_5$: 550.2, found 551.2 (M+H)$^+$.

Step L—Synthesis of Compound 17

A solution of Int-10k (16 mg, 0.029 mmol) and lithium chloride (4.93 mg, 0.116 mmol) in N,N-dimethylformamide (5 mL) was allowed to stir at 80° C. for 3 hours. The mixture was filtered and the filtrate was purified using preparative RP-HPLC to provide compound 17. $^1$H NMR (400 MHz, CD$_3$OD) δ 7.41-7.47 (m, 1H), 7.91-6.99 (m, 2H), 5.95 (d, J=5.60 Hz, 1H), 4.64-4.68 (m, 2H), 4.53-4.61 (m, 2H), 3.92 (d, J=10.06 Hz, 1H), 3.63-3.65 (m, 2H), 3.47 (s, 3H), 3.18-3.21 (m, 1H), 1.12-1.14 (m, 1H), 0.59-0.60 (m, 2H), 0.36-0.37 (m, 2H). Mass Calc'd for C$_{22}$H$_{22}$F$_2$N$_4$O$_5$: 460.2, found 461.2 (M+H)$^+$.

Example 11

Preparation of Compound 18

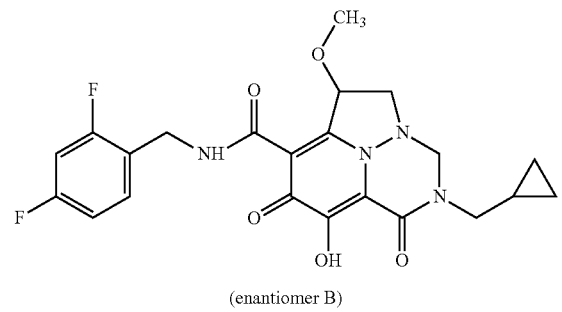

18

(enantiomer B)

Compound 18 was prepared from Int-10j-2 (enantiomer B) using the methodology described in Example 10. $^1$H NMR (400 MHz, CD$_3$OD) δ 7.41-7.47 (m, 1H), 7.91-6.99 (m, 2H), 5.95 (d, J=5.60 Hz, 1H), 4.64-4.68 (m, 2H), 4.54-4.61 (m, 2H), 3.93 (d, J=10.10 Hz, 1H), 3.63-3.65 (m, 2H), 3.47 (s, 3H), 3.18-3.21 (m, 1H), 1.12-1.14 (m, 1H), 0.59-0.60 (m, 2H), 0.36-0.37 (m, 2H). Mass Calc'd for C$_{22}$H$_{22}$F$_2$N$_4$O$_5$: 460.2, found 461.2 (M+H)$^+$.

The following compounds of the present invention were prepared using the methods described in Examples 10 and 11 and substituting the appropriate reactants and/or reagents.

| Compound | Structure | Stereochemistry | Exact Mass [M + H]$^+$ |
|---|---|---|---|
| 19 | 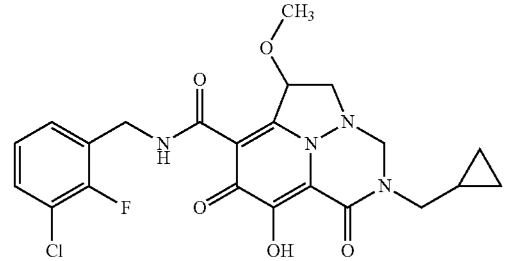 [SMILES: COC1CN2CN(CC3CC3)C(=O)c3c(O)c(=O)c(C(=O)NCc4cccc(Cl)c4F)c1n32] | enantiomer A | Calc'd 477.1, found 477.2 |

-continued
| Compound | Structure | Stereochemistry | Exact Mass [M + H]+ |
|---|---|---|---|
| 20 | | enantiomer B | Calc'd 477.1, found 477.2 |
| 21 | | enantiomer B | Calc'd 477.1, found 477.2 |
| Compound | 1H NMR |
|---|---|
| 19 | 1H NMR (400 MHz, CD3OD) δ 7.31-7.39 (m, 2H), 7.09-7.13 (m, 1H), 5.92 (d, J = 6.4 Hz, 1H), 4.51-4.73 (m, 3H), 3.88-3.92 (m, 2H), 3.59-3.61 (m, 1H), 3.36 (s, 3H), 3.15-3.19 (m, 2H), 1.11-1.13 (m, 1H), 0.56-0.58 (m, 2H), 0.34-0.35 (m, 2H). |
| 20 | 1H NMR (400 MHz, CD3OD) δ 7.35-7.41 (m, 2H), 7.11-7.15 (m, 1H), 5.93 (d, J = 6.4 Hz, 1H), 4.55-4.73 (m, 3H), 3.91-3.94 (m, 2H), 3.61-3.66 (m, 1H), 3.36 (s, 3H), 3.19-3.22 (m, 2H), 1.11-1.13 (m, 1H), 0.59-0.60 (m, 2H), 0.36-0.37 (m, 2H). |
| 21 | 1H NMR (400 MHz, CD3OD) δ 7.10-7.12 (m, 1H), 6.81-6.95 (m, 2H), 5.59 (d, J = 5.2 Hz, 1H), 4.18-4.27 1 (m, 3H), 3.56 (d, J = 10.8 Hz, 1H), 3.25-3.30 (m, H), 3.11 (s, 4H), 2.82-2.86 (m, 2H), 0.78-0.79 (m, 1H), 0.23-0.25 (m, 2H), 0.10-0.15 (m, 2H). |
Example 12
Preparation of Compound 22
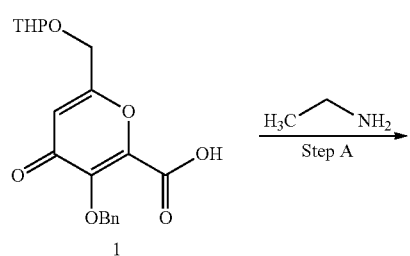
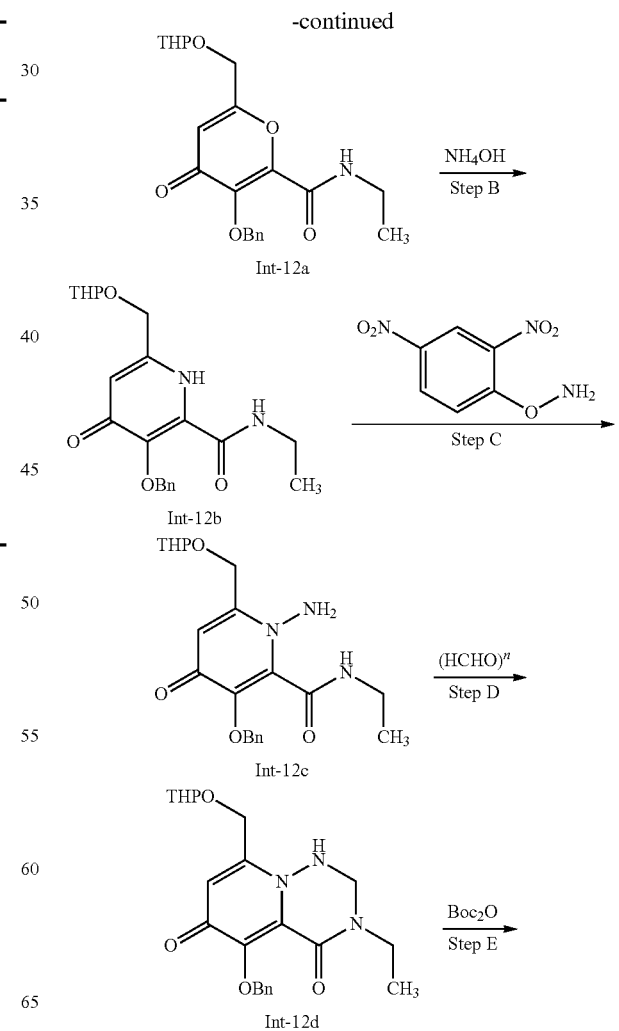

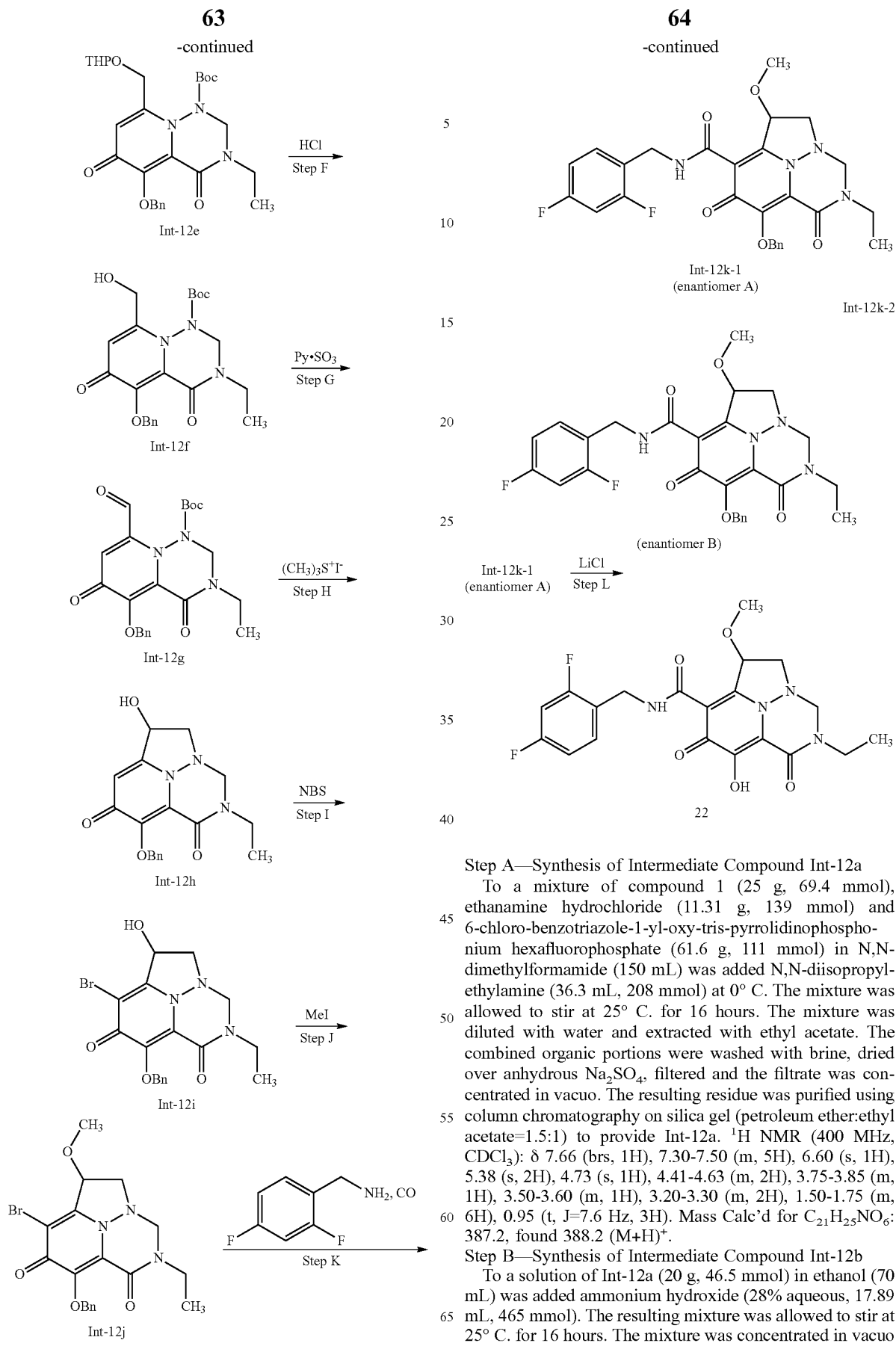

Step A—Synthesis of Intermediate Compound Int-12a

To a mixture of compound 1 (25 g, 69.4 mmol), ethanamine hydrochloride (11.31 g, 139 mmol) and 6-chloro-benzotriazole-1-yl-oxy-tris-pyrrolidinophosphonium hexafluorophosphate (61.6 g, 111 mmol) in N,N-dimethylformamide (150 mL) was added N,N-diisopropylethylamine (36.3 mL, 208 mmol) at 0° C. The mixture was allowed to stir at 25° C. for 16 hours. The mixture was diluted with water and extracted with ethyl acetate. The combined organic portions were washed with brine, dried over anhydrous $Na_2SO_4$, filtered and the filtrate was concentrated in vacuo. The resulting residue was purified using column chromatography on silica gel (petroleum ether:ethyl acetate=1.5:1) to provide Int-12a. $^1$H NMR (400 MHz, $CDCl_3$): δ 7.66 (brs, 1H), 7.30-7.50 (m, 5H), 6.60 (s, 1H), 5.38 (s, 2H), 4.73 (s, 1H), 4.41-4.63 (m, 2H), 3.75-3.85 (m, 1H), 3.50-3.60 (m, 1H), 3.20-3.30 (m, 2H), 1.50-1.75 (m, 6H), 0.95 (t, J=7.6 Hz, 3H). Mass Calc'd for $C_{21}H_{25}NO_6$: 387.2, found 388.2 $(M+H)^+$.

Step B—Synthesis of Intermediate Compound Int-12b

To a solution of Int-12a (20 g, 46.5 mmol) in ethanol (70 mL) was added ammonium hydroxide (28% aqueous, 17.89 mL, 465 mmol). The resulting mixture was allowed to stir at 25° C. for 16 hours. The mixture was concentrated in vacuo to provide Int-12b, which was used without further purification. $^1$H NMR (400 MHz, CD$_3$OD): δ 7.25-7.50 (m, 5H), 6.58 (s, 1H), 5.41 (s, 2H), 4.50-5.00 (m, 3H), 3.80-4.00 (m, 1H), 3.50-3.60 (m, 1H), 3.26 (q, J=7.6 Hz, 2H), 1.50-1.70 (m, 6H), 1.02 (t, J=7.0 Hz, 3H). Mass Calc'd for C$_{21}$H$_{26}$N$_2$O$_5$: 386.2, found 387.2 (M+H)$^+$.

Step C—Synthesis of Intermediate Compound Int-12c

To a solution of Int-12b (19 g, 41.8 mmol) in N,N-dimethylformamide (80 mL) was added K$_2$CO$_3$ (11.55 g, 84 mmol) and O-(2,4-dinitrophenyl)hydroxylamine (12.48 g, 62.7 mmol) at 0° C. The resulting mixture was allowed to stir at 25° C. for 48 hours. The mixture was filtered and the filtrate was concentrated in vacuo. The resulting residue was purified using column chromatography on silica gel (ethyl acetate in petroleum ether 33% to 100% then MeOH in ethyl acetate: 0 to 15%) to provide Int-12c. $^1$H NMR (400 MHz, CD$_3$OD): δ 7.25-7.55 (m, 5H), 6.65 (s, 1H), 5.12 (s, 2H), 4.50-4.80 (m, 3H), 3.83-3.86 (m, 1H), 3.55-3.58 (m, 1H), 3.20-3.30 (m, 2H), 1.55-2.02 (m, 6H), 1.12 (t, J=7.2 Hz, 3H). Mass Calc'd for C$_{21}$H$_{27}$N$_3$O$_5$: 401.2, found 402.1 (M+H)$^+$.

Step D—Synthesis of Intermediate Compound Int-12d

To a solution of Int-12c (11 g, 20.90 mmol) in THF (40 mL) and AcOH (4.00 mL) was added paraformaldehyde (1.556 mL, 20.90 mmol). The resulting mixture was heated at reflux for 16 hours. The reaction mixture was cooled to room temperature, concentrated in vacuo and the resulting residue was treated with saturated aqueous NaHCO$_3$ (2*50 mL). The aqueous was extracted with ethyl acetate and the combined organic layers were washed with brine, dried over anhydrous Na$_2$SO$_4$, filtered and the filtrate was concentrated. The resulting residue was purified using column chromatography on silica gel (petroleum ether in ethyl acetate: 25% to 80%) to provide Int-12d. $^1$H NMR (400 MHz, CD$_3$OD): δ 7.47-7.49 (m, 2H), 7.30-7.34 (m, 3H), 6.68 (s, 1H), 5.20 (s, 2H), 4.75-4.78 (m, 2H), 4.60 (d, J=14.8 Hz, 1H), 4.47 (s, 2H), 3.77-3.90 (t, J=5.2 Hz, 1H), 3.49-3.56 (m, 3H), 1.60-1.78 (m, 6H), 1.19-1.26 (m, 3H). Mass Calc'd for C$_{22}$H$_{27}$N$_3$O$_5$: 413.2, found 414.2 (M+H)$^+$.

Step E—Synthesis of Intermediate Compound Int-12e

To a solution of Int-12d (8.14 g, 17.72 mmol) in dichloromethane (40 mL) was added di-tert-butyl dicarbonate (8.14 mL, 35.4 mmol), triethylamine (5.38 g, 53.2 mmol) and 4-dimethylaminopyridine (0.216 g, 1.772 mmol). The mixture was allowed to stir at 20° C. for 16 hours and then concentrated in vacuo. The resulting residue was purified using column chromatography on silica gel (ethyl acetate in petroleum ether: 25% to 50%) to provide Int-12e. $^1$H NMR (400 MHz, CDCl$_3$): δ 7.61 (d, J=7.2 Hz, 2H), 7.27-7.35 (m, 3H), 6.60 (d, J=10.8 Hz, 1H), 5.44 (d, J=10.8 Hz, 1H), 5.32 (d, J=10.8 Hz, 1H), 5.15 (d, J=12.8 Hz, 1H), 4.32-4.50 (m, 2H), 3.61-3.65 (m, 2H), 3.40-3.54 (m, 2H), 1.52-2.05 (m, 6H), 1.43 (s, 9H), 1.22 (t, J=7.0 Hz, 3H). Mass Calc'd for C$_{27}$H$_{35}$N$_3$O$_7$: 513.2, found 514.3 (M+H)$^+$.

Step F—Synthesis of Intermediate Compound Int-12f

To a solution of Int-12e (6 g, 11.68 mmol) in ethyl acetate (50 mL) was added a solution of HCl in ethyl acetate (4 M, 3 mL) and the mixture was allowed to stir at 20° C. for 10 min. The mixture was concentrated in vacuo and the resulting residue was purified using chromatography on silica gel (ethyl acetate:MeOH=100:2) to provide Int-12f. $^1$H NMR (400 MHz, CD$_3$OD): δ 7.45-7.50 (m, 2H), 7.29-7.40 (m, 3H), 6.68 (s, 1H), 5.10-5.30 (m, 2H), 4.37-4.60 (m, 2H), 3.50-3.60 (m, 3H), 3.30-3.40 (m, 1H), 1.46 (s, 9H), 1.20 (t, J=6.8 Hz, 3H).

Step G—Synthesis of Intermediate Compound Int-12g

To a solution of Int-12f (4.4 g, 10.25 mmol) in dichloromethane (100 mL) was added N,N-diisopropylethylamine (23.26 mL, 133 mmol), DMSO (14.54 mL, 205 mmol) and pyridine-sulfur trioxide complex (19.55 g, 123 mmol). The mixture was allowed to stir at 20° C. for 16 hours. The mixture was washed with aqueous HCl (0.5 M, 50 mL), dried over anhydrous Na$_2$SO$_4$, filtered and the filtrate was concentrated in vacuo to provide Int-12g. $^1$H NMR (400 MHz, CD$_3$OD): δ 9.80 (s, 1H), 7.50-7.60 (m, 2H), 7.26-7.34 (m, 3H), 6.86 (s, 1H), 4.80-5.50 (m, 4H), 3.50-3.70 (m, 1H), 3.25-3.35 (m, 1H), 1.40 (s, 9H), 1.21 (t, J=7.4 Hz, 3H). Mass Calc'd for C$_{22}$H$_{25}$N$_3$O$_6$: 427.2, found 428.1 (M+H)$^+$.

Step H—Synthesis of Intermediate Compound Int-12h

To a solution of trimethylsulfonium iodide (344 mg, 1.684 mmol) in N,N-dimethylformamide (8 mL) was added NaH (135 mg, 3.37 mmol), and the mixture was allowed to stir at 20° C. for 1.5 hours. The mixture was treated with a solution of Int-12g (200 mg, 0.421 mmol) in N,N-dimethylformamide (12.00 mL) and stirred at 20° C. for 30 min. The mixture was treated with water and filtered. The filtrate was purified using preparative RP-HPLC to provide Int-12h. $^1$H NMR (400 MHz, CD$_3$OD): δ 7.51-7.52 (m, 2H), 7.34-7.36 (m, 3H), 7.20 (s, 1H), 5.55-5.58 (d, J=7.2 Hz, 1H), 5.29 (s, 2H), 4.63 (s, 2H), 3.83-3.85 (m, 1H), 3.62-3.68 (t, J=7.2 Hz, 2H), 3.41-3.43 (m, 1H), 1.24-1.28 (d, J=7.0 Hz, 3H). Mass Calc'd for C$_{18}$H$_{19}$N$_3$O$_4$: 341.1, found 341.9 (M+H)$^+$.

Step I—Synthesis of Intermediate Compound Int-12i

To a solution of Int-12h (60 mg, 0.176 mmol) in acetonitrile (8 mL) was added N-bromosuccinimide (37.5 mg, 0.211 mmol). The mixture was allowed to stir at 25° C. for 30 min, concentrated in vacuo and the resulting residue was purified using preparative TLC on silica gel (100% ethyl acetate) to provide Int-12i. $^1$H NMR (400 MHz, CD$_3$OD) δ 7.52-7.53 (m, 2H), 7.31-7.32 (m, 3H), 5.49-7.52 (m, 1H), 5.26 (dd, J=6.4, 6.4 Hz, 2H), 4.63 (d, J=6.4 Hz, 1H), 4.36 (d, J=6.4 Hz, 1H), 3.58-3.61 (m, 3H), 3.35-3.39 (m, 1H), 1.23 (t, J=14 Hz, 3H); Mass Calc'd for C$_{18}$H$_{18}$BrN$_3$O$_4$: 419.0, 421.0, found 420.0, 422.0 (M+H)$^+$.

Step J—Synthesis of Intermediate Compound Int-12j

To a solution of Int-12i (50 mg, 0.119 mmol) in N,N-dimethylformamide (3 mL) was added sodium hydride (2.86 mg, 0.119 mmol) at 0° C. The mixture was allowed to stir at 0° C. for 30 min, treated with iodomethane (16.89 mg, 0.119 mmol) and stirred at 0° C. for 20 min. Water was added and the mixture was extracted with ethyl acetate. The combined organics were dried over Na$_2$SO$_4$, concentrated in vacuo and the resulting residue was purified using preparative TLC (100% ethyl acetate) to provide Int-12j. Mass Calc'd for C$_{19}$H$_{20}$BrN$_3$O$_4$: 433.1, 435.1, found 434.1, 436.1 (M+H)$^+$.

Step K—Synthesis of Intermediate Compound Int-12k-1 (Enantiomer A) and Int-12k-2 (Enantiomer B)

To a solution of Int-12j (40 mg, 0.092 mmol) in methanol (3 mL) and dimethylsulfoxide (1 mL), was added Pd(PPh$_3$)$_4$ (11.60 mg, 0.010 mmol), (2,4-difluorophenyl)methanamine (26.4 mg, 0.184 mmol) and N,N-diisopropylethylamine (11.90 mg, 0.092 mmol). The mixture was allowed to stir at 90° C. for 40 min under carbon monoxide (1 atm). The mixture was cooled to room temperature, diluted with aqueous HCl (1N, 4 mL) and extracted with ethyl acetate. The combined organic portions were washed with brine, dried over anhydrous Na$_2$SO$_4$, filtered and and the filtrate was concentrated in vacuo. The crude was purified using preparative TLC on silica gel (100% ethyl acetate) to provide Int-12k as the racemate. $^1$H NMR (400 MHz, CDCl$_3$) δ 7.54-7.56 (m, 2H), 7.23-7.32 (m, 4H), 6.71-6.78 (m, 2H), 6.03 (s, 1H), 5.26 (dd, J=8, 8 Hz, 2H), 4.54-4.64 (m, 2H), 4.30 (d, J=6.4 Hz, 1H), 4.16 (d, J=6.4 Hz, 1H), 3.70-3.72 (m, 1H), 3.58-3.59 (m, 2H), 3.45 (s, 3H), 3.39-3.41 (m, 1H), 2.88-2.90 (m, 1H), 1.23 (t, J=14 Hz, 3H); Mass Calc'd for C$_{27}$H$_{26}$F$_2$N$_4$O$_5$: 524.2, found 525.2 (M+H)$^+$.

Resolution to the enantiomers was accomplished with SFC (AD, 250 mm×30 mm, 10 um, SC—CO$_2$/methanol 55/45 at 80 mL/min) to provide Int-12k-1 (enantiomer A) and Int-12k-2 (enantiomer B).

Step L—Synthesis of Compound 22

To a solution Int-12k-1 (enantiomer A) (15 mg, 0.028 mmol) in N,N-dimethylformamide (3 mL) was added lithium chloride (12.12 mg, 0.286 mmol). The mixture was allowed to stir at 110° C. for 30 min, cooled to rt and directly purified using preparative RP-HPLC to provide compound 22. $^1$H NMR 0346110-0182-1: (400 MHz, CD$_3$OD) δ 7.40-7.46 (m, 1H), 6.91-6.98 (m, 2H), 5.93-5.94 (m, 1H), 4.82-4.83 (m, 1H), 4.50 (dd, J=8, 8 Hz, 2H), 4.45 (d, J=9.8 Hz, 1H), 3.91 (d, J=9.8 Hz, 1H), 3.61-3.92 (m, 2H), 3.46 (s, 3H), 3.14-3.17 (m, 1H), 1.25 (t, J=14.0 Hz, 3H); Mass Calc'd for C$_{20}$H$_{20}$F$_2$N$_4$O$_5$: 434.1, found 435.2 (M+H)$^+$.

Example 13

Preparation of Compound 23

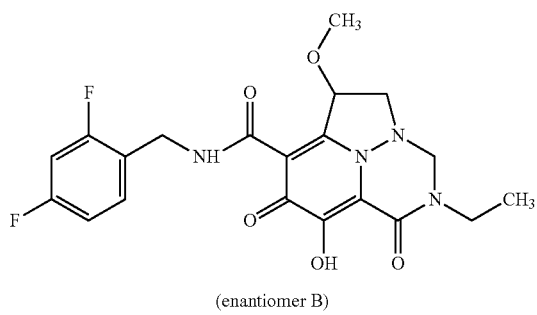

(enantiomer B)

Compound 23 was prepared from Int-12k-2 (enantiomer B) using the methods described in Example 12. $^1$H NMR (400 MHz, CD$_3$OD) δ 7.40-7.46 (m, 1H), 6.91-6.98 (m, 2H), 5.93-5.95 (m, 1H), 4.82-4.85 (m, 1H), 4.50 (dd, J=8.0, 8.0 Hz, 2H), 4.45 (d, J=9.8 Hz, 1H), 3.91 (d, J=9.8 Hz, 1H), 3.61-3.92 (m, 2H), 3.46 (s, 3H), 3.14-3.19 (m, 1H), 1.25 (t, J=14.0 Hz, 3H); Mass Calc'd for C$_{20}$H$_{20}$F$_2$N$_4$O$_5$: 434.1, found 435.2 (M+H)$^+$.

The following compounds of the present invention were prepared using the methods described in Examples 12 and 13 and substituting the appropriate reactants and/or reagents.

| Compound | Structure | Stereochemistry | Exact Mass [M + H]$^+$ |
|---|---|---|---|
| 24 | 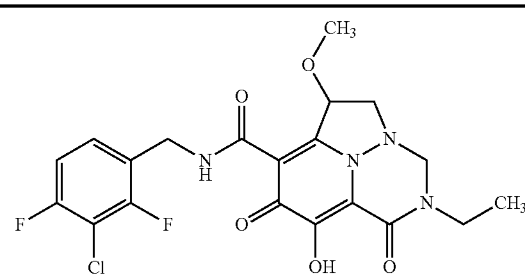 | enantiomer A$^a$ | Calc'd 469.1, found 469.1 |
| 25 | 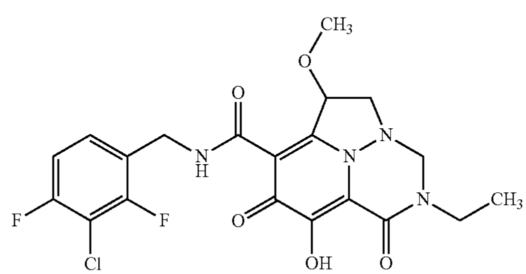 [SMILES: CCN1CN2CC(OC)c3c(C(=O)NCc4ccc(F)c(Cl)c4F)c(=O)c(O)c(n32)C1=O] | enantiomer B$^a$ | Calc'd 469.1, found 469.1 |
| 26 | 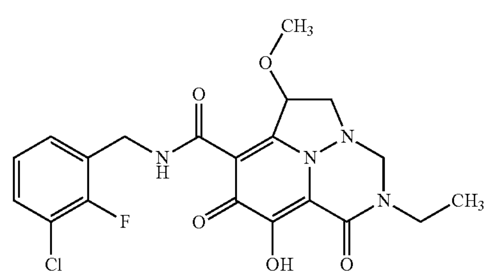 [SMILES: CCN1CN2CC(OC)c3c(C(=O)NCc4cccc(Cl)c4F)c(=O)c(O)c(n32)C1=O] | enantiomer A$^b$ | Calc'd 451.1, found 451.1 |

| Compound | Structure | Stereochemistry | Exact Mass [M + H]+ |
|---|---|---|---|
| 27 | 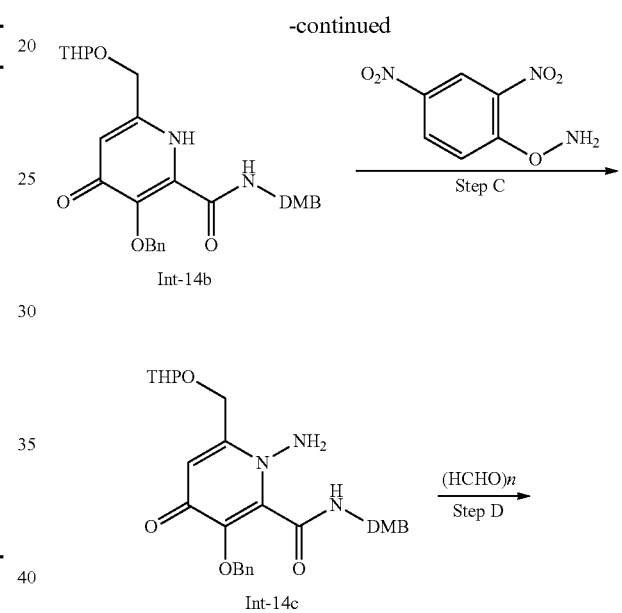 | enantiomer B[b] | Calc'd 451.1, found 451.1 |

[a]SFC (AD, 250 mm × 30 mm, 10 μm, SC—CO$_2$/ethanol + 0.1% NH$_4$OH 65:35 at 80 mL/min)
[b]SFC (OJ, 250 mm × 30 mm, 10 μm, SC—CO$_2$/ethanol 65:35 at 80 mL/min)

| Compound | $^1$H NMR |
|---|---|
| 24 | $^1$H NMR (400 MHz, CD$_3$OD) δ 7.32-7.42 (m, 1H), 7.07 (t, J = 8.22 Hz, 1H), 5.90 (d, J = 5.09 Hz, 1H), 4.78-4.84 (m, 1H), 4.54-4.72 (m, 2H), 4.47 (d, J = 10.17 Hz, 1H), 3.89 (d, J = 10.96 Hz, 1H), 3.55-3.72 (m, 2H), 3.44 (s, 3H), 3.11-3.21 (m, 1H), 1.24 (t, J = 7.04 Hz, 3H). |
| 25 | $^1$H NMR (400 MHz, CD$_3$OD) δ 7.30-7.43 (m, 1H), 7.07 (t, J = 8.41 Hz, 1H), 5.90 (d, J = 5.48 Hz, 1H), 4.82 (d, J = 10.17 Hz, 1H), 4.55-4.73 (m, 2H), 4.47 (d, J = 10.17 Hz, 1H), 3.89 (d, J = 10.96 Hz, 1H), 3.54-3.71 (m, 2H), 3.44 (s, 3H), 3.16 (dd, J = 5.67, 10.76 Hz, 1H), 1.24 (t, J = 7.04 Hz, 3H). |
| 26 | $^1$H NMR (400 MHz, CD$_3$OD) δ 7.31-7.38 (m, 2H), 7.11 (t, J = 8.11 Hz, 1H), 5.91 (d, J = 5.20 Hz, 1H), 4.60-4.72 (m, 2H), 4.44-4.47 (m, 1H), 3.94 (d, J = 10.00 Hz, 1H), 3.89 (d, J = 10.96 Hz, 1H), 3.55-3.68 (m, 2H), 3.44 (s, 3H), 3.13-3.17 (m, 1H), 1.24 (t, J = 7.04 Hz, 3H) |
| 27 | $^1$H NMR (400 MHz, CD$_3$OD) δ 7.31-7.38 (m, 2H), 7.11 (t, J = 8.11 Hz, 1H), 5.91 (d, J = 5.20 Hz, 1H), 4.60-4.72 (m, 2H), 4.44-4.47 (m, 1H), 3.94 (d, J = 10.00 Hz, 1H), 3.89 (d, J = 10.96 Hz, 1H), 3.60-3.68 (m, 2H), 3.44 (s, 3H), 3.13-3.17 (m, 1H), 1.24 (t, J = 7.04 Hz, 3H) |

Example 14

Preparation of Compound 28

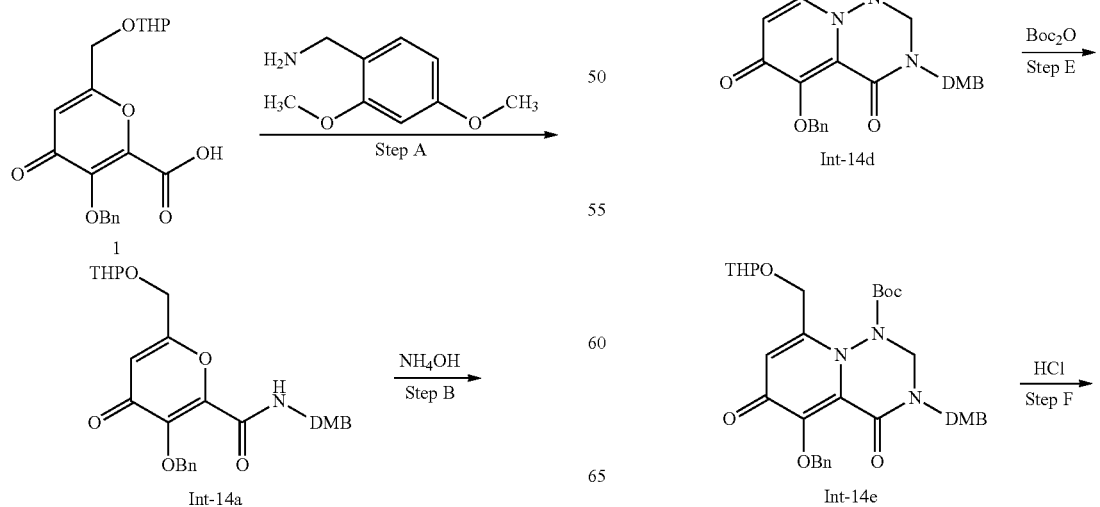

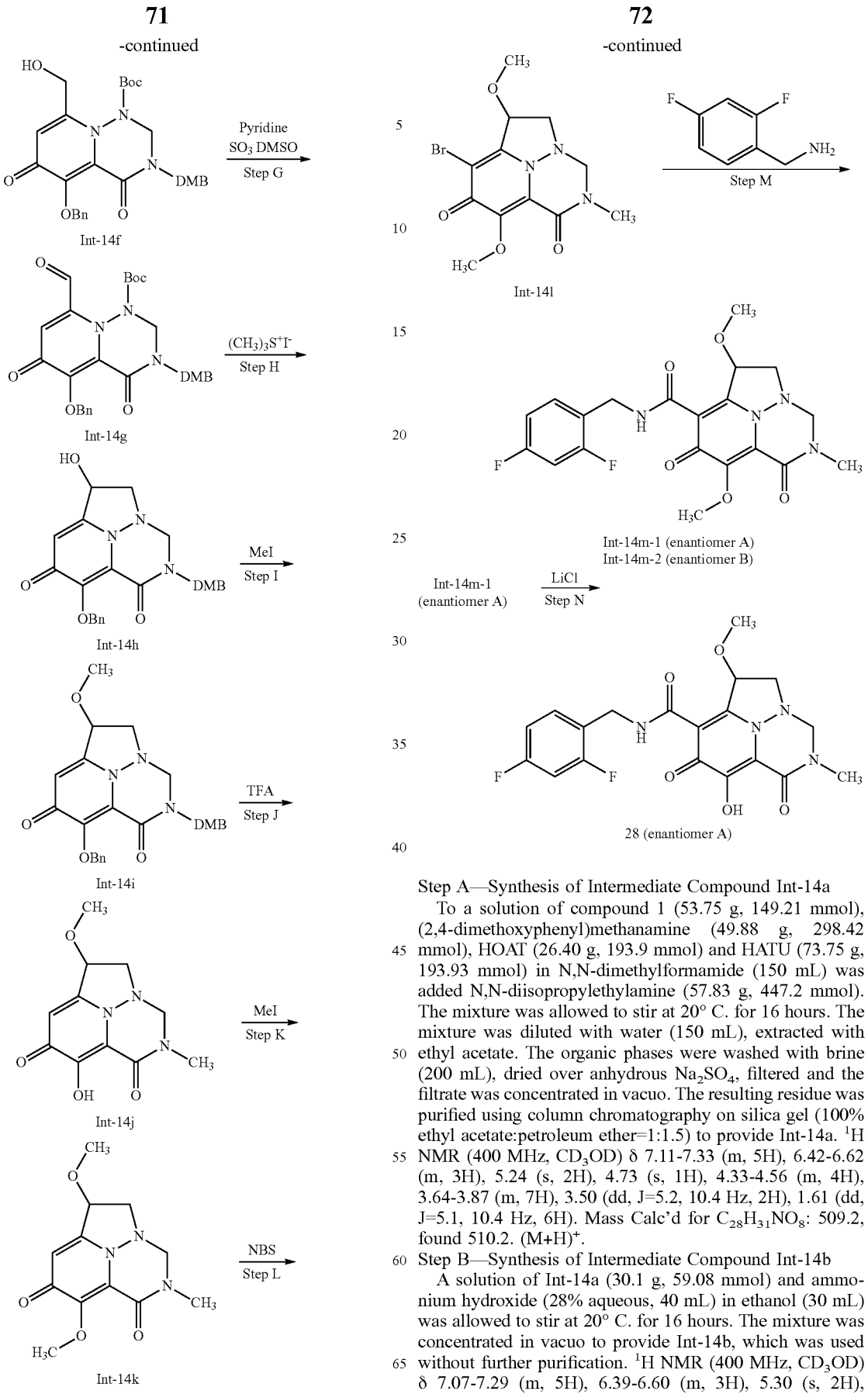

Step A—Synthesis of Intermediate Compound Int-14a

To a solution of compound 1 (53.75 g, 149.21 mmol), (2,4-dimethoxyphenyl)methanamine (49.88 g, 298.42 mmol), HOAT (26.40 g, 193.9 mmol) and HATU (73.75 g, 193.93 mmol) in N,N-dimethylformamide (150 mL) was added N,N-diisopropylethylamine (57.83 g, 447.2 mmol). The mixture was allowed to stir at 20° C. for 16 hours. The mixture was diluted with water (150 mL), extracted with ethyl acetate. The organic phases were washed with brine (200 mL), dried over anhydrous $Na_2SO_4$, filtered and the filtrate was concentrated in vacuo. The resulting residue was purified using column chromatography on silica gel (100% ethyl acetate:petroleum ether=1:1.5) to provide Int-14a. $^1$H NMR (400 MHz, $CD_3OD$) δ 7.11-7.33 (m, 5H), 6.42-6.62 (m, 3H), 5.24 (s, 2H), 4.73 (s, 1H), 4.33-4.56 (m, 4H), 3.64-3.87 (m, 7H), 3.50 (dd, J=5.2, 10.4 Hz, 2H), 1.61 (dd, J=5.1, 10.4 Hz, 6H). Mass Calc'd for $C_{28}H_{31}NO_8$: 509.2, found 510.2. (M+H)$^+$.

Step B—Synthesis of Intermediate Compound Int-14b

A solution of Int-14a (30.1 g, 59.08 mmol) and ammonium hydroxide (28% aqueous, 40 mL) in ethanol (30 mL) was allowed to stir at 20° C. for 16 hours. The mixture was concentrated in vacuo to provide Int-14b, which was used without further purification. $^1$H NMR (400 MHz, $CD_3OD$) δ 7.07-7.29 (m, 5H), 6.39-6.60 (m, 3H), 5.30 (s, 2H), 4.57-4.72 (m, 3H), 4.35-4.46 (m, 2H), 3.70-3.94 (m, 7H), 3.38-3.59 (m, 2H), 1.57 (s, 6H). Mass Calc'd for $C_{28}H_{32}N_2O_7$: 508.2, found 509.2. (M+H)+.

Step C—Synthesis of Intermediate Compound Int-14c

To a solution of Int-14b (30.1 g, 47.34 mmol) and $K_2CO_3$ (13.09 g, 94.8 mmol) in N,N-dimethylformamide (100 mL) was added O-(2,4-dinitrophenyl)hydroxylamine (14.15 g, 70.95 mmol) in portions with stirring at 20° C. The reaction mixture was allowed to stir at 20° C. for 48 hours. The mixture was filtered and the filtrate was purified using preparative RP-HPLC (water with 0.05% $NH_4OH$/acetonitrile) to provide Int-14c. $^1H$ NMR (400 MHz, $CD_3OD$) δ 7.17-7.35 (m, 5H), 6.58-6.66 (m, 1H), 6.45 (d, J=1.6 Hz, 1H), 6.26 (dd, J=2.0, 8.2 Hz, 1H), 5.00-5.14 (m, 2H), 4.55-4.81 (m, 3H), 4.41 (s, 2H), 3.63-3.94 (m, 7H), 3.54 (d, J=11.3 Hz, 2H), 1.50-1.85 (m, 6H). Mass Calc'd for $C_{28}H_{33}N_3O_7$: 523.2, found 524.2. (M+H)+.

Step D—Synthesis of Intermediate Compound Int-14d

Paraformaldehyde (0.614 g, 20.53 mmol) was added to a solution of Int-14c (10.75 g, 20.53 mmol) in tetrahydrofuran (50 mL) and acetic acid (10.75 mL). The mixture was allowed to stir at 80° C. for 18 hours. The mixture was concentrated in vacuo to provide Int-14d, which was used without further purification. $^1H$ NMR (400 MHz, $CD_3OD$) δ 7.18-7.34 (m, 5H), 6.62 (s, 1H), 6.56 (d, J=2.0 Hz, 1H), 6.50 (dd, J=2.0, 8.2 Hz, 1H), 5.12-5.21 (m, 2H), 4.53-4.73 (m, 5H), 4.41 (s, 2H), 3.73-3.84 (m, 7H), 3.41-3.58 (m, 2H), 1.52-1.74 (m, 6H). Mass Calc'd for $C_{29}H_{33}N_3O_7$: 535.2, found 536.2. (M+H)+.

Step E—Synthesis of Intermediate Compound Int-14e

To a solution of Int-14d (6.02 g, 11.2 mmol), triethylamine (4.69 mL, 33.71 mmol) and di-tert-butyl dicarbonate (5.220 mL, 22.49 mmol) in dichloromethane (50 mL) was added 4-dimethylaminopyridine (0.137 g, 1.12 mmol). The mixture was allowed to stir at 25° C. for 16 hours. The mixture was concentrated in vacuo and the resulting residue was purified using column chromatography on silica gel (petroleum ether:ethyl acetate=1:1 to 1:2) to provide Int-14e. $^1H$ NMR (400 MHz, $CD_3OD$) δ 7.07-7.48 (m, 6H), 6.42-6.69 (m, 3H), 5.11-5.35 (m, 3H), 4.60-4.75 (m, 3H), 4.35-4.53 (m, 2H), 3.72-3.92 (m, 6H), 3.37-3.64 (m, 3H), 1.54-1.92 (m, 6H), 1.07-1.49 (m, 9H). Mass Calc'd for $C_{34}H_{41}N_3O_9$: 635.3, found 636.2. (M+H)+.

Step F—Synthesis of Intermediate Compound Int-14f

To a solution of Int-14e (4.95 g, 9.10 mmol) in ethyl acetate (10 mL) was added HCl in ethyl acetate (4 M, 4.14 mL) at 0° C. The mixture was allowed to stir at 25° C. for 10 min. The mixture was concentrated in vacuo and purified using column chromatography on silica gel (ethyl acetate:methanol=100:2) to provide Int-14f. $^1H$ NMR (400 MHz, $CD_3OD$) δ 6.99-7.26 (m, 6H), 6.45-6.62 (m, 3H), 6.15-6.31 (m, 2H), 4.66-4.79 (m, 4H), 4.25-4.41 (m, 2H), 3.74 (d, J=2.0 Hz, 6H), 1.06-1.56 (m, 9H). Mass Calc'd for $C_{29}H_{33}N_3O_8$: 551.2, found 552.1. (M+H)+.

Step G—Synthesis of Intermediate Compound Int-14g

To a solution of Int-14f (2.75 g, 4.99 mmol), dimethylsulfoxide (7.09 mL, 99.7 mmol) and N,N-diisopropylethylamine (11.33 mL, 64.8 mmol) in dichloromethane (50 mL) was added sulfur trioxide pyridine complex (9.53 g, 59.9 mmol). The mixture was allowed to stir at 25° C. for 16 hours. The mixture was diluted with aqueous HCl (1 N, 15 mL), washed with aqueous HCl (1 N, 3×20 mL) and brine, dried over anhydrous $Na_2SO_4$, filtered and the filtrate was concentrated in vacuo to provide Int-14g which was used without further purification. $^1H$ NMR (400 MHz, $CDCl_3$) δ 9.75 (s, 1H), 7.45 (d, J=3.5 Hz, 2H), 7.19-7.32 (m, 3H), 6.81 (s, 1H), 6.30-6.51 (m, 3H), 5.48 (d, J=10.5 Hz, 2H), 5.30 (d, J=5.5 Hz, 1H), 4.83-4.90 (m, 1H), 4.55 (d, J=13.7 Hz, 1H), 4.38 (d, J=14.1 Hz, 1H), 3.76 (d, J=9.8 Hz, 6H), 1.29 (s, 9H). Mass Calc'd for $C_{29}H_{31}N_3O_8$: 549.2, found 550.1. (M+H)+.

Step H—Synthesis of Intermediate Compound Int-14h

To a solution of trimethylsulfonium iodide (1093 mg, 5.33 mmol) in N,N-dimethylformamide (26 mL) was added NaH (215 mg, 5.33 mmol) with stirring at under a nitrogen atmosphere and the mixture was allowed to stir at 25° C. for 2 hours. A solution of Int-14g (2330 mg, 5.33 mmol) in N,N-dimethylformamide (3 mL) was added dropwise to the mixture at 0° C. and the mixture was allowed to stir at 0° C. for 10 min under nitrogen atmosphere. The mixture was diluted with water (2 mL) at 0° C. and filtered. The filtrate was directly purified using preparative RP-HPLC to provide Int-14h. $^1H$ NMR (400 MHz, $CD_3OD$) δ 7.48 (d, J=5.1 Hz, 2H), 7.29 (d, J=5.9 Hz, 3H), 6.65 (s, 1H), 5.37 (t, J=6.3 Hz, 1H), 5.23 (s, 2H), 4.48 (s, 4H), 3.73 (s, 4H), 3.62 (s, 1H), 3.55 (t, J=4.9 Hz, 2H), 3.34 (s, 3H), 3.23 (s, 1H). Mass Calc'd for $C_{25}H_{25}N_3O_6$: 463.2, found 464.1 (M+H)+.

Step I—Synthesis of Intermediate Compound Int-14i

To a solution of Int-14h (600 mg, 1.294 mmol) and sodium hydride (156 mg, 6.48 mmol) in N,N-dimethylformamide (10 mL) was added iodomethane (1102 mg, 7.76 mmol). The mixture was allowed to stir at 25° C. for 16 hours. The mixture was diluted with water (10 mL) and extracted with ethyl acetate. The organic phase was dried over anhydrous $Na_2SO_4$ and filtered. The filtrate was concentrated in vacuo and the resulting residue was purified using preparative TLC on silica gel (dichloromethane:methanol=10:1) to provide Int-14i. $^1H$ NMR (400 MHz, $CD_3OD$) δ 7.25 (d, J=8.6 Hz, 1H), 6.71 (s, 1H), 6.41-6.58 (m, 2H), 5.03-5.13 (m, 1H), 4.88-4.91 (m, 2H), 4.55-4.69 (m, 3H), 4.40 (d, J=10.6 Hz, 1H), 3.54-4.00 (m, 9H), 3.43 (s, 3H). Mass Calc'd for $C_{26}H_{27}N_3O_6$: 477.2, found 478.2 (M+H)+.

Step J—Synthesis of Intermediate Compound Int-14j

A mixture of Int-14i (200 mg, 0.498 mmol) in trifluoroacetic acid (5 mL) was stirred under microwave irradiation at 110° C. for 1 hour. The mixture was concentrated in vacuo and the resulting residue was purified using preparative TLC on silica gel (dichloromethane:methanol=10:1) to provide Int-14j. $^1H$ NMR (400 MHz, $CD_3OD$) δ 5.28 (s, 1H), 4.37-4.63 (m, 3H), 4.00 (s, 3H), 3.66 (s, 2H), 3.50 (s, 3H). Mass Calc'd for $C_{H}H_{13}N_3O_4$: 251.1, found 252.2 (M+H)+.

Step K—Synthesis of Intermediate Compound Int-14k

To a solution of Int-14j (60 mg, 0.238 mmol) and $K_2CO_3$ (66.0 mg, 00.478 mmol) in N,N-dimethylformamide (2 mL) was added MeI (0.044 mL, 0.716 mmol). The mixture was allowed to stir at 25° C. for 16 hours. The mixture was purified using preparative RP-HPLC to provide Int-14k. $^1H$ NMR (400 MHz, $CD_3OD$) δ 5.40-5.55 (m, 1H), 4.73-4.90 (m, 3H), 4.12-4.30 (m, 3H), 3.80-3.92 (m, 2H), 3.55-3.64 (m, 3H), 3.19-3.27 (m, 3H). Mass Calc'd for $C_{12}H_{15}N_3O_4$: 265.1, found 266.2 (M+H)+.

Step L—Synthesis of Intermediate Compound Int-14l

To a solution of Int-14k (40 mg, 0.159 mmol) in acetonitrile (3 mL) was added N-bromosuccinimide (42.5 mg, 0.239 mmol). The mixture was allowed to stir at 20° C. for 3 hours. The mixture was directly purified using preparative TLC on silica gel (dichloromethane:methanol=10:1) to provide Int-14l. $^1H$ NMR (400 MHz, $CD_3OD$) δ 5.30 (s, 1H), 4.67 (s, 1H), 4.64 (s, 1H), 3.92 (s, 3H), 3.52 (s, 3H), 3.31-3.34 (m, 2H), 3.15 (s, 3H). Mass Calc'd for $C_{12}H_{14}BrN_3O_4$: 343.0, 345.0, found 344.1, 346.1 (M+H)+.

Step M—Synthesis of Intermediate Compound Int-14m-1 (Enantiomer A) and Int-14m-2 (Enantiomer B)

To a solution of Int-14l (30 mg, 0.087 mmol), (2,4-difluorophenyl)methanamine (37.42 mg, 0.261 mmol) and N,N-diisopropylethylamine (0.076 mL, 0.436 mmol) in dimethylsulfoxide (1 mL) and methanol (3 mL) was added Pd(Ph$_3$P)$_4$ (50.4 mg, 0.0435 mmol) in one portion. The mixture was allowed to stir at 90° C. under carbon monoxide (1 atm) for 5 hours. The mixture was cooled to rt and filtered. The filtrate was directly purified using preparative RP-HPLC to provide Int-14m as the racemate. $^1$H NMR (400 MHz, CD$_3$OD) δ: 7.40-7.50 (m, 1H), 6.85-7.00 (m, 2H), 6.94 (d, J=5.6 Hz, 1H), 4.58-4.70 (m, 2H), 4.40 (d, J=10.4 Hz, 1H), 3.94 (s, 3H), 3.85 (d, J=10.4 Hz, 1H), 3.46 (s, 3H), 3.10-3.15 (m, 4H), 2.70 (d, =12.0 Hz, 1H). Mass Calc'd for C$_{20}$H$_{20}$F$_2$N$_4$O$_5$: 434.1, found 435.2 (M+H)$^+$.

Resolution to the enantiomers was accomplished with SFC (AD, 250 mm×30 mm, 10 μm, SC—CO$_2$/i-PrOH=60/40 at 80 mL/min) to provide Int-14m-1 (enantiomer A) and Int-14m-2 (enantiomer B)

Step N—Synthesis of Compound 28

A solution of Int-14m-1 (3.0 mg, 6.9 μmol) and lithium chloride (2.9 mg, 0.069 mmol) in N,N-dimethylformamide (2 mL) was allowed to stir at 80° C. for 5 hours. The mixture was cooled to rt and filtered. The filtrate was directly purified using preparative RP-HPLC to provide compound 28. $^1$H NMR (400 MHz, CD$_3$OD) δ 7.42 (d, J=7.2 Hz, 1H), 6.93 (d, J=10.8 Hz, 2H), 5.94 (s, 1H), 4.61 (d, J=14.0 Hz, 2H), 4.44 (s, 2H), 3.81-4.00 (m, 2H), 3.37-3.56 (m, 3H), 3.04-3.24 (m, 3H). Mass Calc'd for C$_{19}$H$_{18}$F$_2$N$_4$O$_5$: 420.1, found 421.2 (M+H)$^+$.

Example 15

Preparation of Compound 29

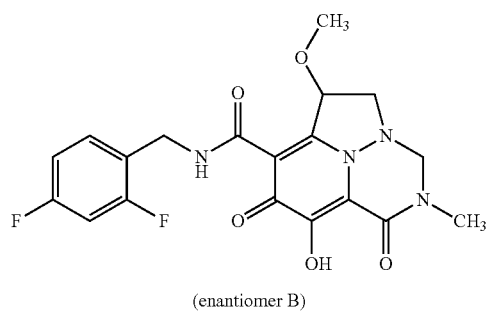

(enantiomer B)

Compound 29 was prepared from Int-14m-2 (enantiomer B) using the methods described in Example 14. $^1$H NMR (400 MHz, CD$_3$OD) δ 7.42 (dd, J=7.6, 14.7 Hz, 1H), 6.85-7.01 (m, 2H), 5.93 (d, J=5.2 Hz, 1H), 4.53-4.67 (m, 2H), 4.44 (d, J=8.4 Hz, 2H), 3.89 (d, J=10.4 Hz, 2H), 3.39-3.57 (m, 3H), 3.03-3.21 (m, 3H). Mass Calc'd for C$_{19}$H$_{18}$F$_2$N$_4$O$_5$: 420.1, found 421.2 (M+H)$^+$.

The following compounds of the present invention were prepared using the methods described in Examples 14 and 15 and substituting the appropriate reactants and/or reagents.

| Compound | Structure | Stereochemistry | Exact Mass [M + H]$^+$ |
|---|---|---|---|
| 30 | 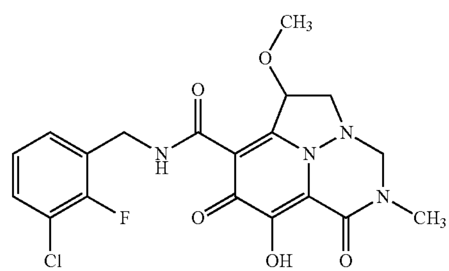 [SMILES: COC1CN2CN(C)C(=O)c3c(O)c(=O)c(C(=O)NCc4cccc(Cl)c4F)c1n32] | enantiomer A[a] | Calc'd 437.1, found 437.2 |
| 31 | 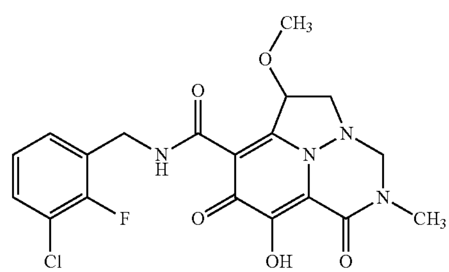 [SMILES: COC1CN2CN(C)C(=O)c3c(O)c(=O)c(C(=O)NCc4cccc(Cl)c4F)c1n32] | enantiomer B[a] | Calc'd 437.1, found 437.2 |
| 32 | 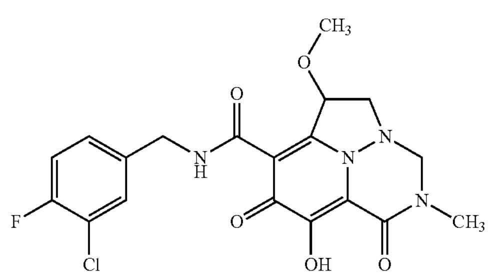 [SMILES: COC1CN2CN(C)C(=O)c3c(O)c(=O)c(C(=O)NCc4ccc(F)c(Cl)c4)c1n32] | enantiomer A[b] | Calc'd 437.1, found 437.2 |

| Compound | Structure | Stereochemistry | Exact Mass [M + H]+ |
|---|---|---|---|
| 33 | 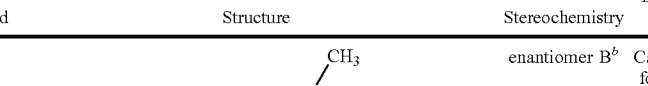 | enantiomer B[b] | Calc'd 437.1, found 437.2 |

[a]SFC (OJ, 250 mm × 30 mm, 10 μm, SC—CO$_2$/ethanol = 65/35 at 80 mL/min)
[b]SFC (AS, 250 mm × 30 mm, 50 μm, SC—CO$_2$/ethanol = 60/40 at 40 mL/min)

| Compound | $^1$H NMR |
|---|---|
| 30 | $^1$H NMR (400 MHz, CD$_3$OD) δ 7.31-7.38 (m, 1H), 7.07 (t, J = 15.2 Hz, 1H), 5.90 (d, J = 5.2 Hz, 1H), 4.75-4.77 (m, 3H), 4.43-4.69 (m, 1H), 3.88 (d, J = 10.8 Hz, 1H), 3.44 (s, 3H), 3.32-3.33 (m, 1H), 3.15 (s, 3H). |
| 31 | $^1$H NMR (400 MHz, CD$_3$OD) δ 7.31-7.38 (m, 1H), 7.08 (t, J = 15.2 Hz, 1H), 5.90 (d, J = 5.2 Hz, 1H), 4.75-4.77 (m, 3H), 4.43-4.69 (m, 1H), 3.88 (d, J = 10.8 Hz, 1H), 3.44 (s, 3H), 3.32-3.33 (m, 1H), 3.15 (s, 3H). |
| 32 | $^1$H NMR (400 MHz, CD$_3$OD) δ 7.44-7.46 (m, 1H), 7.15-7.29 (m, 2H), 5.92 (d, J = 4.8 Hz, 1H), 4.75-4.78 (m, 1H), 4.43-4.57 (m, 2H), 3.88 (d, J = 10.8 Hz, 1H), 3.45-3.51 (m, 5H), 3.15 (s, 3H). |
| 33 | $^1$H NMR (400 MHz, CD$_3$OD) δ 7.44-7.46 (m, 1H), 7.15-7.29 (m, 2H), 5.92 (d, J = 5.2 Hz, 1H), 4.75-4.78 (m, 1H), 4.43-4.61 (m, 2H), 3.88 (d, J = 10.8 Hz, 1H), 3.45-3.51 (m, 5H), 3.15 (s, 3H). |

Example 16

Preparation of Compound 34

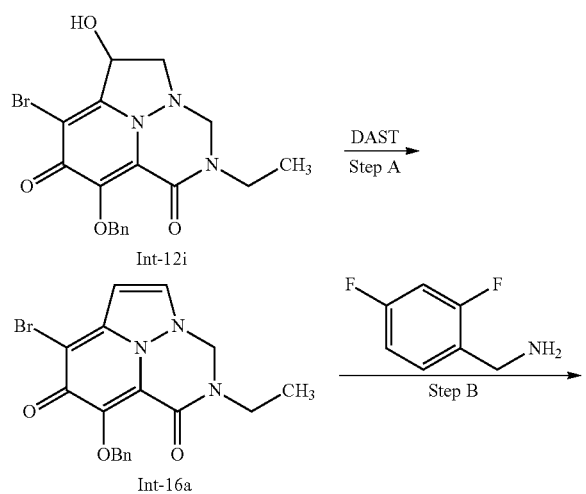

Step A—Synthesis of Intermediate Compound Int-16a

A solution of Int-12i (50 mg, 0.119 mmol) and diethylaminosulfur trifluoride (DAST) (19.2 mg, 0.12 mmol) in dichloromethane (5 mL) was allowed to stir at 20° C. for 16 hours. The mixture was diluted with water (5 mL) and extracted with dichloromethane. The combined organic portions were washed with brine (15 mL), dried over anhydrous Na$_2$SO$_4$, filtered and the filtrate was concentrated in vacuo. The resulting residue was purified using preparative TLC (ethyl acetate:methanol=10:1) to provide Int-16a. $^1$H NMR (400 MHz, CD$_3$OD) δ 7.98 (brs, 1H), 7.60 (d, J=6.2 Hz, 2H), 7.31 (d, J=7.8 Hz, 3H), 6.59-6.68 (m, 1H), 5.51 (brs, 2H), 5.29 (s, 2H), 3.68 (d, J=7.0 Hz, 2H), 1.26 (t, J=6.8 Hz, 3H). Mass Calc'd for C$_{18}$H$_{16}$BrN$_3$O$_3$: 401.0, 403.0, found 402.1, 404.1 (M+H)+.

Step B—Synthesis of Intermediate Compound Int-16b

To a mixture of Int-16a (40 mg, 0.28 mmol), N,N-diisopropylethylamine (0.081 mL, 0.49 mmol), (oxydi-2,1-phenylene)bis(diphenylphosphine) (DPEphos) (15.1 mg, 0.03 mmol) was added dimethylsulfoxide (2 mL). The mixture was allowed to stir at 20° C. for 5 min and then treated with added Pd(OAc)$_2$ (4.2 mg, 0.02 mmol). The mixture was stirred under carbon monoxide (1 atm) at 90° C. for 3 hours. The mixture was diluted with aqueous HCl (1 N, 3 mL) and extracted with ethyl acetate. The combined organic portions were washed with brine, dried over anhydrous Na$_2$SO$_4$, filtered and the filtrate was concentrated in vacuo. The crude was purified using preparative TLC on silica gel (ethyl acetate:methanol=9:1) to provide Int-16b. $^1$H NMR (400 MHz, CD$_3$OD) δ 8.00 (brs, 1H), 7.54-7.65

(m, 1H), 7.18-7.53 (m, 5H), 6.92 (brs, 2H), 6.41-6.61 (m, 1H), 5.40-5.62 (m, 2H), 5.15-5.40 (m, 2H), 4.61 (brs, 2H), 3.65 (brs, 1H), 3.44 (brs, 1H), 1.26 (brs, 3H). Mass Calc'd for $C_{26}H_{22}F_2N_4O_4$: 492.2 found, 493.3 (M+H)$^+$.

Step C—Synthesis of Compound 34

A solution of lithium chloride (8.1 mg, 0.19 mmol) and Int-16b (18.7 mg, 0.04 mmol) in N,N-dimethylformamide (2 mL) was allowed to stir at 80° C. for 3 hours. The mixture was filtered and the filtrate was directly purified using preparative RP-HPLC to provide compound 34. $^1$H NMR (400 MHz, CD$_3$OD) δ 7.84-8.05 (m, 1H), 7.43 (brs, 2H), 6.91-6.98 (m, 1H), 5.62-5.74 (m, 1H), 4.85-4.89 (m, 2H), 4.65 (brs, 2H), 3.69-3.85 (m, 2H), 1.30 (d, J=11.7 Hz, 3H). Mass Calc'd for $C_{19}H_{16}F_2N_4O_4$: 402.1, found 403.2 (M+H)$^+$.

Example 17

Preparation of Compound 35

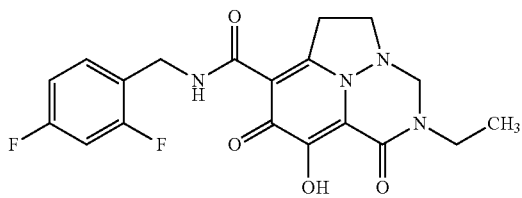

35

A mixture of compound 34 (30 mg, 0.061 mmol) and Pd/C (5 mg) in methanol (10 mL) was allowed to stir at 20° C. under hydrogen (1 atm) for 13 hours. The mixture was filtered and the filtrate was concentrated in vacuo. The resulting residue was purified using preparative RP-HPLC to provide compound 35. $^1$H NMR (400 MHz, dimethylsulfoxide-d6) δ 10.77-10.80 (m, 1H), 7.33-7.41 (m, 1H), 7.19-7.23 (m, 1H), 7.00-7.05 (m, 1H), 4.46-4.48 (m, 4H), 3.45-3.90 (m, 2H), 2.63 (s, 2H), 2.29 (m, 2H), 1.08-1.14 (m, 3H). Mass Calc'd for $C_{19}H_{18}F_2N_4O_4$: 404.1, found 405.2 (M+H)$^+$.

Example 18

Preparation of Compound 36

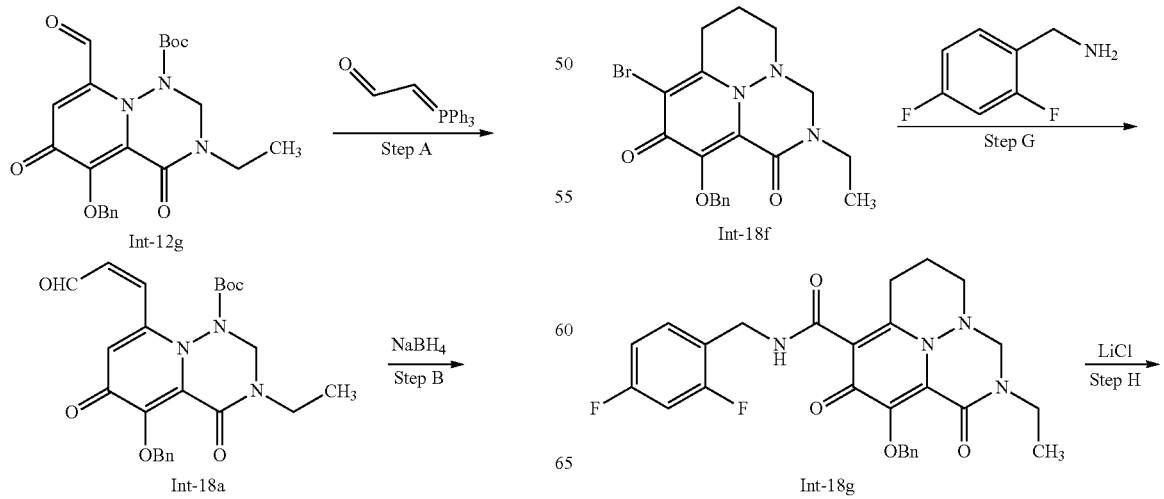

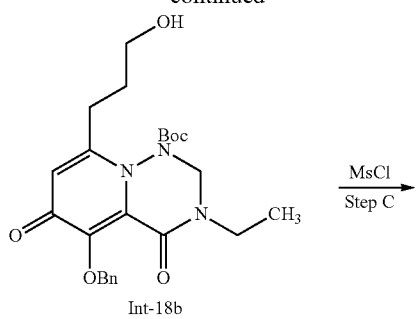

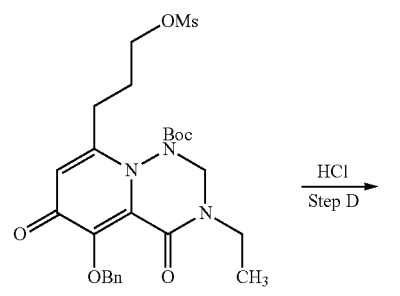

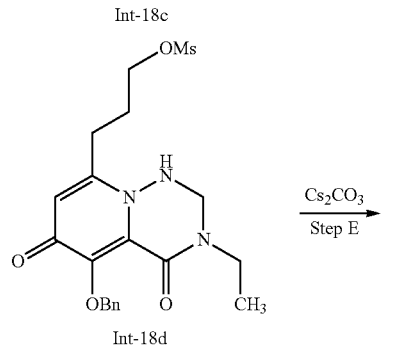

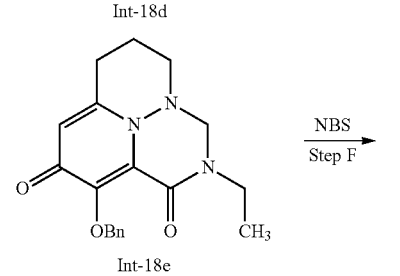

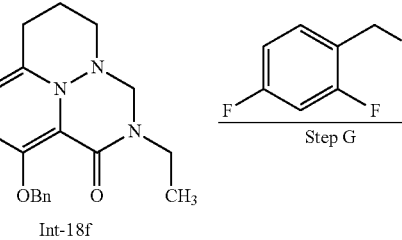

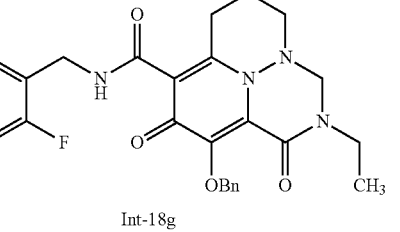

81

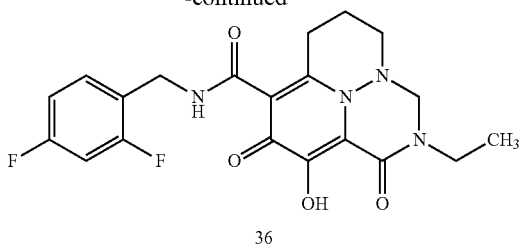

36

Step A—Synthesis of Intermediate Compound Int-18a

To a solution of 2-(triphenylphosphoranylidene)acetaldehyde (256 mg, 0.842 mmol) in tetrahydrofuran (15 mL) was added Int-12g (300 mg, 0.702 mmol) at 10° C. under nitrogen. The mixture was allowed to stir at 10° C. for 18 hours. The mixture was quenched with water (30 mL) and extracted with ethyl acetate. The combined organic portions were dried over anhydrous $Na_2SO_4$, filtered and the filtrate was concentrated in vacuo to provide Int-18a. $^1$H NMR (400 MHz, $CD_3OD$) δ 9.95-9.97 (m, 1H), 7.51-7.60 (m, 2H), 7.21-7.24 (m, 3H), 6.52 (s, 1H), 5.31-5.33 (m, 1H), 5.14-5.17 (m, 1H), 5.02-5.05 (m, 1H), 4.81-4.84 (m, 1H), 3.53-3.60 (m, 2H), 3.18-3.26 (m, 2H), 1.28 (s, 9H), 1.08-1.14 (m, 3H). Mass Calc'd for $C_{24}H_{27}N_3O_6$: 453.2, found 454.1 $(M+H)^+$.

Step B—Synthesis of Intermediate Compound Int-18b

To a solution of Int-18a (200 mg, 0.442 mmol) in tetrahydrofuran (6 mL) was added $NaBH_4$ (50.06 mg, 1.324 mmol). The mixture was allowed to stir at 10° C. for 3 hours. The mixture was quenched with water (15 mL) and extracted with ethyl acetate. The combined organic layers were dried over anhydrous $Na_2SO_4$, filtered and the filtrate was concentrated in vacuo. The resulting residue was purified using preparative TLC on silica gel (ethyl acetate:methanol=10:1) to provide Int-18b. $^1$H NMR (400 MHz, $CD_3OD$) δ 7.46-7.47 (m, 2H), 7.32-7.34 (m, 3H), 6.45 (s, 1H), 5.17-5.34 (m, 3H), 4.79-4.82 (m, 1H), 3.62-3.63 (m, 3H), 3.55-3.59 (m, 1H), 3.16-3.17 (m, 1H), 2.74-2.77 (m, 1H), 2.65-2.68 (m, 1H), 1.81-1.87 (m, 2H), 1.47 (s, 9H), 1.20-1.24 (m, 3H). Mass Calc'd for $C_{24}H_{31}N_3O_6$: 457.2, found 458.1 $(M+H)^+$.

Step C—Synthesis of Intermediate Compound Int-18c

To a solution of Int-18b (100 mg, 0.218 mmol) in dichloromethane (4 mL) was added triethylamine (66.4 mg, 0.656 mmol), followed by methanesulfonyl chloride (50.08 mg, 0.438 mmol). The mixture was allowed to stir at 10° C. for 18 hours. The reaction was quenched with water (10 mL), extracted with ethyl acetate. The combined organic layers were dried over anhydrous $Na_2SO_4$, filtered and concentrated in vacuo to provide Int-18c. $^1$H NMR (400 MHz, $CDCl_3$) δ 7.53-7.55 (m, 2H), 7.20-7.26 (m, 3H), 6.19 (s, 1H), 5.29-5.31 (m, 1H), 5.14-5.15 (m, 1H), 5.00-5.03 (m, 1H), 4.66-4.69 (m, 1H), 4.15-4.19 (m, 2H), 3.52-3.56 (m, 1H), 3.29-3.30 (m, 1H), 3.06-3.07 (m, 1H), 2.92 (s, 3H), 2.63-2.67 (m, 1H), 2.46-2.50 (m, 1H), 1.40 (s, 9H), 1.12-1.37 (m, 3H). Mass Calc'd for $C_{25}H_{33}N_3O_8S$: 535.2, found 536.2 $(M+H)^+$.

Step D—Synthesis of Intermediate Compound Int-18d

A solution of Int-18c (100 mg, 0.185 mmol) in 1% HCl in methanol (5 mL) was allowed to stir at 55° C. for 16 hours. The mixture was concentrated in vacuo to provide Int-18d, which was used without further purification. Mass Calc'd for $C_{20}H_{25}N_3O_6S$: 435.1, found 436.1 $(M+H)^+$.

82

Step E—Synthesis of Intermediate Compound Int-18e

To a solution of Int-18d (80 mg, 0.185 mmol) in N,N-dimethylformamide (1 mL) was added cesium carbonate (297.5 mg, 0.920 mmol). The mixture was allowed to stir at 55° C. for 4 hours and then filtered and the filtrate was concentrated in vacuo to provide Int-18e, which was used without further purification. $^1$H NMR 0356873-0093-1a: (400 MHz, $CD_3OD$) δ 7.39-7.40 (m, 2H), 7.23-7.24 (m, 3H), 6.33 (s, 1H), 5.10 (s, 2H), 4.36-4.50 (m, 3H), 3.46-3.56 (m, 3H), 3.15-3.19 (m, 2H), 1.97-2.00 (m, 2H), 1.10-1.13 (m, 3H). Mass Calc'd for $C_{19}H_{21}N_3O_3$: 339.2, found 339.9 $(M+H)^+$.

Step F—Synthesis of Intermediate Compound Int-18f

To a solution of Int-18e (40 mg, 0.117 mmol) in acetonitrile (3 mL) was added N-bromosuccinimide (105 mg, 0.589 mmol). The mixture was allowed to stir at 20° C. for 10 min. The crude product was purified using preparative TLC on silica gel (100% ethyl acetate) to provide Int-18f. $^1$H NMR (400 MHz, $CD_3OD$) δ 7.49-7.50 (m, 2H), 7.31-7.33 (m, 3H), 5.20 (s, 2H), 4.59 (s, 2H), 3.52-3.54 (m, 2H), 3.26-3.28 (m, 2H), 3.06-3.10 (m, 2H), 2.09-2.12 (m, 2H), 1.19-1.22 (m, 3H). Mass Calc'd for $C_{19}H_{20}BrN_3O_3$: 417.1, 419.1, found 418.1, 420.1 $(M+H)^+$.

Step G—Synthesis of Intermediate Compound Int-18g

To a solution of Int-18f (33 mg, 0.079 mmol) in dimethylsulfoxide (1 mL) and methanol (4 mL) was added (2,4-difluorophenyl)methanamine (22.4 mg, 0.16 mmol), DIPEA (0.3 mL) and $Pd(PPh_3)_4$ (44 mg). The mixture was allowed to stir at 80° C. for 1 hour, cooled to room temperature, diluted with water (3 mL) and extracted with ethyl acetate. The combined organic portions were dried over anhydrous $Na_2SO_4$, filtered and the filtrate was concentrated in vacuo. The resulting residue was purified using preparative TLC on silica gel (ethyl acetate:methanol=14:1) to provide Int-18g. $^1$H NMR (400 MHz, $CD_3OD$) δ 7.39-7.49 (m, 3H), 7.21-7.23 (m, 3H), 6.84-6.89 (m, 2H), 5.11 (s, 2H), 4.60 (s, 2H), 4.49 (s, 2H), 3.46-3.48 (m, 2H), 3.42-3.44 (m, 2H), 3.15-3.17 (m, 2H), 1.93-1.98 (m, 2H), 1.10-1.14 (m, 3H). Mass Calc'd for $C_{27}H_{26}F_2N_4O_4$: 508.2, found 509.3 $(M+H)^+$.

Step H—Synthesis of Compound 36

To a solution of Int-18g (13.2 mg, 0.026 mmol) in N,N-dimethylformamide (5 mL) was added LiCl (11.04 mg, 0.259 mmol). The mixture was heated to 100° C. for 30 min, cooled to rt and filtered. The filtrate was directly purified using preparative RP-HPLC to provide compound 36. $^1$H NMR (400 MHz, $CD_3OD$) δ 7.50-7.56 (m, 1H), 6.92-6.95 (m, 2H), 4.80 (s, 2H), 4.55 (s, 2H), 3.57-3.62 (m, 2H), 3.42-3.44 (m, 2H), 3.20-3.23 (m, 2H), 2.01-2.04 (m, 2H), 1.22-1.25 (m, 3H). Mass Calc'd for $C_{20}H_{20}F_2N_4O_4$: 418.1, found 419.0 $(M+H)^+$.

Example 19

Preparation of Compound 37

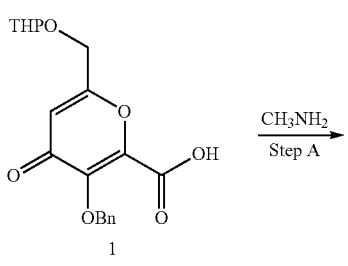

-continued

Int-19a → (NH₄OH, Step B)

Int-19b → (2,4-dinitrophenyl-O-NH₂, Step C)

Int-19c → (3-oxotetrahydrofuran, Step D)

Int-19d → (Boc₂O, Step E)

Int-19e → (HCl, Step F)

Int-19f → (Py·SO₃, Step G)

-continued

Int-19g → ((CH₃)₃S⁺I⁻, Step H)

Int-19h → (NBS, Step I)

Int-19i → (MeI, Step J)

Int-19j → (2,4-difluorobenzylamine, Step K)

Int-19k-1a (diastereomer 1, enantiomer A)
Int-19k-1b (diastereomer 1, enantiomer B)
Int-19k-2a (diastereomer 2, enantiomer A)
Int-19k-2b (diastereomer 2, enantiomer B)

Int-19k-1a (diastereomer 1, enantiomer A) → (LiCl, Step L)

-continued

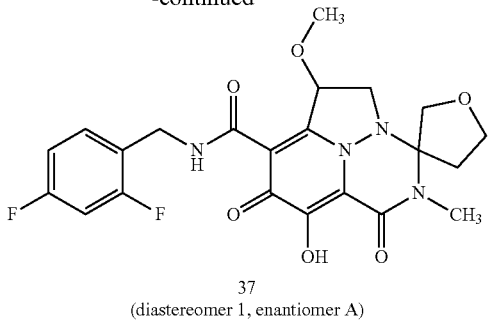

37
(diastereomer 1, enantiomer A)

Step A—Synthesis of Intermediate Compound Int-19a

To a stirred solution of compound 1 (10 g, 27.8 mmol), 6-chloro-benzotriazole-1-yl-oxy-tris-pyrrolidinophosphonium hexafluorophosphate (24.63 g, 44.4 mmol) and methanamine hydrochloride (3.75 g, 55.5 mmol) in N,N-dimethylformamide (100 mL) was added N,N-diisopropylethylamine (14.54 mL, 83 mmol) at 0° C. The resulting mixture was allowed to stir at 20° C. for 16 hours. The mixture was poured into water (500 mL) and extracted with ethyl acetate. The combined organic portions were washed with brine, dried over anhydrous sodium sulfate, filtered and the filtrate was concentrated in vacuo. The resulting residue was purified using column chromatography on silica gel (ethyl acetate in petroleum ether: 0 to 50%) to provide Int-19a. $^1$H NMR (400 MHz, CDCl$_3$) δ 8.02 (brs, 1H), 7.39-7.41 (m, 5H), 6.61 (s, 1H), 5.38 (s, 2H), 4.74-4.75 (m, 1H), 4.62 (d, J=15.2 Hz, 1H), 4.44 (d, J=15.2 Hz, 1H), 3.79-3.84 (m, 1H), 3.53-3.56 (m, 1H), 3.89 (s, 3H), 1.56-3.04 (m, 6H). Mass Calc'd for $C_{20}H_{23}NO_6$: 373.2, found 374.2 (M+H)$^+$.

Step B—Synthesis of Intermediate Compound Int-19b

A solution of Int-19a (9.85 g, 20.06 mmol) and ammonium hydroxide (28% aqueous, 170 mL) in ethanol (100 mL) was allowed to stir at 20° C. for 16 hours. The mixture was concentrated in vacuo to provide Int-19b, which was used without further purification. $^1$H NMR (400 MHz, CDCl$_3$) δ 8.20 (brs, 1H), 7.27-7.41 (m, 5H), 6.40 (s, 1H), 5.46 (s, 2H), 4.68-4.69 (m, 1H), 4.65 (d, J=15.2 Hz, 1H), 4.55 (d, J=15.2 Hz, 1H), 3.99-4.00 (m, 1H), 3.57-3.60 (m, 1H), 3.88 (s, 3H), 1.59-1.88 (m, 6H). Mass Calc'd for $C_{20}H_{24}N_2O_5$: 372.2, found 373.1 (M+H)$^+$.

Step C—Synthesis of Intermediate Compound Int-19c

To a stirred solution of Int-19b (9.35 g, 20.09 mmol) and K$_2$CO$_3$ (3.78 g, 20.09 mmol) in N,N-dimethylformamide (50 mL) was added O-(2,4-dinitrophenyl)hydroxylamine (8.00 g, 40.2 mmol) at 0° C. The resulting mixture was allowed to stir at 20° C. for 24 hours. The mixture was filtered and the filtrate was purified using preparative RP-HPLC (water with 0.05% NH$_4$OH/acetonitrile) to provide Int-19c. $^1$H NMR (400 MHz, CD$_3$OD) δ 7.28-7.41 (m, 5H), 6.63 (s, 1H), 5.11 (s, 2H), 4.85-4.86 (m, 1H), 4.76-4.84 (m, 1H), 3.82-3.88 (m, 1H), 3.54-3.57 (m, 1H), 3.82 (s, 3H), 1.57-1.58 (m, 6H). Mass Calc'd for $C_{24}H_{25}N_3O_5$: 387.2, found 388.1 (M+H)$^+$.

Step D—Synthesis of Intermediate Compound Int-19d

A solution of Int-19c (168 mg, 0.412 mmol) and acetic acid (0.1 mL) in tetrahydrofuran (2 mL) was added dihydrofuran-3(2H)-one (643 mg, 7.47 mmol). The resulting mixture was heated at 75° C. for 20 hours. The mixture was filtered and the filtrate was purified using preparative RP-HPLC (water with 0.05% NH$_4$OH/acetonitrile) to provide Int-19d. $^1$H NMR (400 MHz, CD$_3$OD) δ 7.36 (d, J=3.2 Hz, 2H), 7.29 (t, J=5.6 Hz, 3H), 6.66 (s, 1H), 5.25 (s, 2H), 4.48-4.87 (m, 2H), 4.50-4.56 (m, 1H), 3.98-3.99 (m, 2H), 3.81-3.86 (m, 2H), 3.53-3.55 (m, 2H), 3.02 (s, 3H), 1.56-1.89 (m, 8H). Mass Calc'd for $C_{24}H_{29}N_3O_6$: 455.2, found 456.0 (M+H)$^+$.

Step E—Synthesis of Intermediate Compound Int-19e

To a solution of Int-19d (2 g, 4.53 mmol) in dichloromethane (50 mL) was added 4-dimethylaminopyridine (0.055 g, 0.453 mmol), triethylamine (1.263 mL, 9.06 mmol) and di-tert-butyl dicarbonate (3.104 mL, 9.06 mmol). The mixture was allowed to stir at 20° C. for 16 hours. The mixture was concentrated in vacuo and the resulting residue was purified using column chromatography silica gel (petroleum ether/ethyl acetate=1:1) to provide Int-19e. $^1$H NMR (400 MHz, CD$_3$OD) δ 7.63 (d, J=13.8 Hz, 2H), 7.27-7.35 (m, 3H), 6.60-6.65 (m, 1H), 5.45 (d, J=10.8 Hz, 1H), 5.21 (d, J=10.8 Hz, 1H), 4.61-4.74 (m, 2H), 4.51-4.54 (m, 1H), 3.81-3.98 (m, 2H), 3.71-3.79 (m, 2H), 3.53-3.55 (m, 2H), 3.10 (s, 3H), 1.40-3.08 (m, 8H), 1.39 (s, 9H). Mass Calc'd for $C_{29}H_{37}N_3O_8$: 555.3, found 556.1 (M+H)$^+$.

Step F—Synthesis of Intermediate Compound Int-19f

To a solution of Int-19e (1.8 g, 3.24 mmol) in ethyl acetate (20 mL) was added a solution of HCl in ethyl acetate (4 M, 1 mL), the mixture was allowed to stir at 20° C. for 10 minutes. The mixture was concentrated in vacuo and the resulting residue was purified using column chromatography on silica gel (ethyl acetate:methanol=100:2) to provide Int-19f. $^1$H NMR (400 MHz, CD$_3$OD) δ 7.26-7.32 (m, 5H), 6.68 (s, 1H), 5.42-5.44 (m, 1H), 5.19-5.28 (m, 1H), 4.52-4.56 (m, 1H), 4.36-4.40 (m, 1H), 3.96-4.04 (m, 2H), 3.62-3.75 (m, 2H), 3.08 (s, 3H), 3.17-3.20 (m, 2H), 1.38 (s, 9H). Mass Calc'd for $C_{24}H_{29}N_3O_7$: 471.2, found 473.1 (M+H)$^+$.

Step G—Synthesis of Intermediate Compound Int-19g

To a solution of Int-19f (1.1 g, 3.333 mmol) in dichloromethane (20 mL) was added N,N-diisopropylethylamine (5.30 mL, 30.3 mmol), dimethylsulfoxide (3.31 mL, 46.7 mmol) and sulfur trioxide pyridine complex (4.46 g, 28.0 mmol), the mixture was allowed to stir at 20° C. for 16 hours. The mixture was washed with aqueous HCl (0.5 M, 10 mL), dried over anhydrous sodium sulfate, filtered and the filtrate was concentrated in vacuo to provide Int-19g, which was used without further purification. $^1$H NMR (400 MHz, CDCl$_3$) δ 9.79 (s, 1H), 7.41-7.43 (m, 1H), 7.19-7.23 (m, 1H), 6.79 (s, 1H), 5.55-5.61 (m, 1H), 5.27-5.31 (m, 1H), 3.56-3.59 (m, 2H), 3.00-3.05 (m, 2H), 3.55 (s, 3H), 3.17-3.20 (m, 2H), 1.36 (s, 9H). Mass Calc'd for $C_{24}H_{27}N_3O_7$: 469.2, found 488.3 (M+H$_3$O)$^+$.

Step H—Synthesis of Intermediate Compound Int-19h

A solution of trimethylsulfonium iodide (348 mg, 1.704 mmol) in N,N-dimethylformamide (8 mL)) was treated with sodium hydride (147 mg, 3.66 mmol) at 20° C. The mixture was stirred under nitrogen at 20° C. for 1.5 hours. A solution of Int-19g (200 mg, 0.426 mmol) in N,N-dimethylformamide (12 mL) was added dropwise to the mixture at 20° C. The mixture was stirred at 20° C. for 10 min under nitrogen atmosphere and then diluted with water (3 mL) at 0° C. The mixture was directly purified using preparative RP-HPLC to provide Int-19h. $^1$H NMR (400 MHz, CD$_3$OD) δ 7.30-7.45 (m, 5H), 7.06 (s, 1H), 5.43-5.47 (m, 1H), 5.32 (m, 2H), 3.63-3.99 (m, 6H), 3.10-3.15 (m, 3H), 3.09 (s, 3H). Mass Calc'd for $C_{20}H_{21}N_3O_5$: 383.1, found 384.1 (M+H)$^+$.

Step I—Synthesis of Intermediate Compound Int-19i

A solution of Int-19h (84 mg, 0.219 mmol) in acetonitrile (3 mL) was treated with N-bromosuccinimide (58.5 mg, 0.329 mmol). The mixture was allowed to stir at 20° C. for 10 mins and then directly purified using preparative TLC on silica gel (ethyl acetate:methanol=14:1) to provide Int-19i.

¹H NMR (400 MHz, CD₃OD) δ 7.42-7.43 (m, 2H), 7.29-7.30 (m, 3H), 5.45-5.49 (m, 1H), 5.35-5.37 (m, 1H), 5.23-5.33 (m, 1H), 3.59-4.08 (m, 6H), 3.63-3.99 (m, 4H), 3.13 (s, 3H), 3.10-3.15 (m, 3H). Mass Calc'd for $C_{20}H_{20}BrN_3O_5$: 461.1, 463.1, found 462.1, 464.2 (M+H)⁺.

Step J—Synthesis of Intermediate Compound Int-19j

To a solution of Int-19i (100 mg, 0.216 mmol) in N,N-dimethylformamide (5 mL) was added sodium hydride (26.0 mg, 0.649 mmol) and iodomethane (307 mg, 3.163 mmol) at 18° C., the mixture was allowed to stir at 18° C. for 5 minutes. Water (5 mL) was added and the mixture was extracted with ethyl acetate. The combined organic portions were washed with brine and concentrated in vacuo. The resulting residue was purified using preparative TLC on silica gel (ethyl acetate:methanol=14:1) to provide Int-19j. ¹H NMR (400 MHz, CD₃OD) δ 7.39-7.42 (m, 2H), 7.26-7.28 (m, 3H), 5.33-5.38 (m, 1H), 5.18-5.23 (m, 2H), 3.52-3.41 (m, 2H), 3.50 (s, 3H), 3.11 (s, 3H), 3.10-3.15 (m, 3H). Mass Calc'd for $C_{21}H_{22}BrN_3O_5$: 475.1, 477.1, found 476.1, 478.1 (M+H)⁺.

Step K—Synthesis of Intermediate Compound Int-19k-1a, Int-19k-1b, Int-19k-2a and Int-19k-2b A solution of Int-19j (90 mg, 0.189 mmol) in dimethylsulfoxide (2 mL) and methanol (2 mL) was treated with (2,4-difluorophenyl)methanamine (54.1 mg, 0.378 mmol), N,N-diisopropylethylamine (0.066 mL, 0.378 mmol) and Pd(Ph₃P)₄ (21.83 mg, 0.019 mmol). The mixture was heated at 90° C. under carbon monoxide (1 atm) for 3 hours. Ethyl acetate (10 mL) was added and the reaction mixture was filtered. The filtrate was washed with aqueous HCl (0.5 M, 4 mL), dried over anhydrous sodium sulfate, filtered and the filtrate was concentrated in vacuo. The resulting residue was purified using preparative TLC on silica gel (100% ethyl acetate) to provide Int-19k-1 (diastereomer 1, higher $R_f$ on silica gel) and Int-19k-2 (diastereomer 2, lower $R_f$ on silica gel).

Int-19k-1 (diastereomer 1) ¹H NMR (400 MHz, CD₃OD) δ 7.19-7.62 (m, 7H), 6.83-6.88 (m, 1H), 5.81-5.82 (m, 1H), 5.27-5.31 (m, 1H), 5.13-5.16 (m, 1H), 4.49-4.55 (m, 2H), 3.73-4.05 (m, 6H), 3.55 (s, 3H), 3.04 (s, 3H), 3.09-3.12 (m, 2H). Mass Calc'd for $C_{29}H_{28}F_2N_4O_6$: 566.2, found 567.3 (M+H)⁺.

Int-19k-2 (diastereomer 2) ¹H NMR (400 MHz, CD₃OD) δ 7.19-7.66 (m, 7H), 6.86-6.88 (m, 1H), 5.76-5.77 (m, 1H), 5.24-5.27 (m, 1H), 5.13-5.16 (m, 1H), 4.53-4.59 (m, 2H), 3.46-4.02 (m, 6H), 3.35 (s, 3H), 3.04 (s, 3H), 3.05-3.23 (m, 2H). Mass Calc'd for $C_{29}H_{28}F_2N_4O_6$: 566.2, found 567.3 (M+H)⁺.

Resolution of Int-19k-1 (diastereomer 1) was accomplished with SFC (OJ, 250 mm×30 mm, 5 μm, 30% methanol with 0.05% NH₄OH in SC—CO₂, 80 mL/min) to provide Int-19k-1a (diastereomer 1, enantiomer A) and Int-19k-1b (diastereomer 1, enantiomer B) Resolution of Int-19k-2 (diastereomer 2) was accomplished with SFC (OJ, 250 mm×30 mm, 5 μm, 30% methanol with 0.05% NH₄OH in SC—CO₂, 80 mL/min) to provide Int-19k-2a (diastereomer 2, enantiomer A) and Int-19k-2b (diastereomer 2, enantiomer B)

Step L—Synthesis of Compound 37 (diastereomer 1, enantiomer A)

To a solution of Int-19k-1a (diastereomer 1, enantiomer A) (5 mg, 8.83 μmol) in N,N-dimethylformamide (1 mL) was added lithium chloride (0.374 mg, 8.83 μmol). The mixture was heated at 80° C. for 3 hours, cooled to rt and directly purified using preparative RP-HPLC to provide compound 37. ¹H NMR (400 MHz, CD₃OD) δ 7.40-7.46 (m, 1H), 6.90-6.98 (m, 2H), 5.93 (d, J=4.4 Hz, 1H), 4.60-4.68 (m, 3H), 4.32 (d, J=11.6 Hz, 1H), 3.84-4.12 (m, 4H), 3.45 (s, 3H), 3.21 (s, 3H), 3.47-3.52 (m, 1H), 3.06-3.14 (m, 1H). Mass Calc'd for $C_{22}H_{22}F_2N_4O_6$: 476.2, found 477.2 (M+H)⁺.

The following compounds of the present invention were prepared using the methods described in Example 19 and substituting the appropriate reactants and/or reagents.

| Compound | Structure | prepared from: | Stereochemistry | Exact Mass [M + H]⁺ |
|---|---|---|---|---|
| 38 | 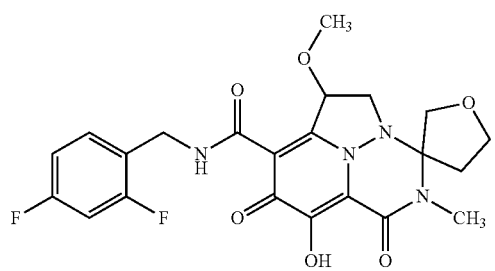 [SMILES: COC1CN2n3c(c(O)c(=O)c(C(=O)NCc4ccc(F)cc4F)c31)C(=O)N(C)C21CCOC1] | Int-19k-1b | diast 1, ent B | Calc'd 477.2, found 477.2 |
| 39 | 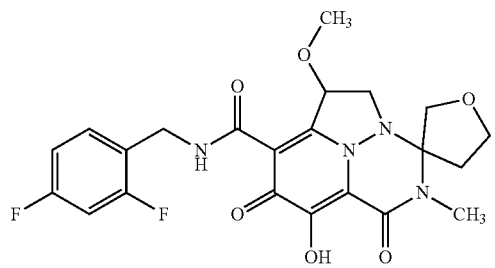 [SMILES: COC1CN2n3c(c(O)c(=O)c(C(=O)NCc4ccc(F)cc4F)c31)C(=O)N(C)C21CCOC1] | Int-19k-2a | diast 2, ent A | Calc'd 477.2, found 477.2 |

| Compound | Structure | prepared from: | Stereo-chemistry | Exact Mass [M + H]+ |
|---|---|---|---|---|
| 40 | 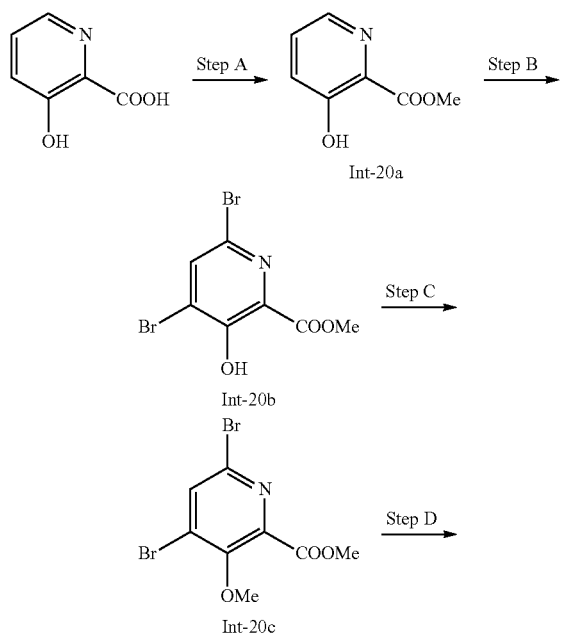 | Int-19k-2b | diast 2, ent B | Calc'd 477.2, found 477.2 |

| Compound | 1H NMR |
|---|---|
| 38 | 1H NMR (400 MHz, CD3OD) δ 7.40-7.46 (m, 1H), 6.90-6.98 (m, 2H), 5.93 (d, J = 5.6 Hz, 1H), 4.60-4.68 (m, 3H), 4.32 (d, J = 12 Hz, 1H), 3.84-4.12 (m, 4H), 3.46 (s, 3H), 3.22 (s, 3H), 3.47-3.50 (m, 1H), 3.03-3.14 (m, 1H). |
| 39 | 1H NMR (400 MHz, CD3OD) δ 7.40-7.46 (m, 1H), 6.90-6.98 (m, 2H), 5.90 (d, J = 5.6 Hz, 1H), 4.60-4.68 (m, 3H), 4.17-4.20 (m, 2H), 3.56-4.14 (m, 3H), 3.46 (s, 3H), 3.24 (s, 3H), 3.73-3.78 (m, 1H), 3.47-3.51 (m, 1H). |
| 40 | 1H NMR (400 MHz, CD3OD) δ 7.40-7.46 (m, 1H), 6.90-6.98 (m, 2H), 5.90 (d, J = 6 Hz, 1H), 4.60-4.68 (m, 3H), 4.17-4.20 (m, 2H), 3.56-4.04 (m, 3H), 3.46 (s, 3H), 3.24 (s, 3H), 3.73-3.78 (m, 1H), 3.47-3.51 (m, 1H). |

Example 20

Preparation of Compound Int-20f

Step A—Synthesis of Compound Int-20a

To a solution of 3-hydroxypicolinic acid (340 g, 2.44 mol) in 2.8 L of MeOH stirred at 15° C., was added $H_2SO_4$ (720 g, 7.33 mol). The reaction was heated to 65° C. with an oil bath and stirred for 2 hours. After it was cooled to room temperature, the reaction content was neutralized to pH=7 by slow addition of saturated $Na_2CO_3$ aqueous solution. The resulting mixture was extracted with ethyl acetate. The combined organic layers were washed with brine, dried over anhydrous $Na_2SO_4$. After filtration, the filtrate was concentrated under vacuum to give compound Int-20a. The crude material was used in the next reaction without further purification. 1H NMR (400 MHz, CDCl3) δ 10.62 (s, 1H), 6.28 (d, J=4.4 Hz, 2H), 4.05 (s, 3H).

Step B—Synthesis of Compound Int-20b

To a mixture of in compound Int-20a (50 g, 327 mmol) in $H_2O$ (5.0 L) stirred at 15° C., was add bromine (157 g, 979 mmol). The mixture was stirred at 15° C. for 5 hours. The resulting mixture was filtered, the filter cake was washed with water and dried under vacuum to give compound Int-20b. The crude material was used in the next reaction without further purification. 1H NMR (400 MHz, CDCl3) δ 11.37 (s, 1H), 7.87 (s, 1H), 4.07 (s, 3H).

Step C—Synthesis of Compound Int-20c

To a solution of compound Int-20b (200 g, 643 mmol) in acetone (4.0 L) stirred at 15° C., was added Cs$_2$CO$_3$ (377 g, 1.160 mol) followed by dropwise addition of iodomethane (274 g, 1930 mmol). The reaction was heated at 60° C. for 2 hours. After it was cooled to room temperature, the reaction mixture was filtered. The filter cake was washed with acetone, and purified by silica gel chromatography eluting with petroleum ether:EtOAc=25:1~10:1 to give compound Int-20c. $^1$H NMR (400 MHz, CDCl$_3$) δ 7.85 (s, 1H), 3.99 (s, 3H), 3.98 (s, 3H).

Step D—Synthesis of Compound Int-20d

To a solution of compound Int-20c (350 g, 1080 mmol, 1.0 eq) in THF (1.8 L) stirred at 15° C., was added H$_2$O (350 mL) followed by lithium hydroxide monohydrate (54 g, 1300 mmol). The reaction mixture was stirred at 25° C. for 2 hours. The solvent was removed under vacuum to give compound Int-20d as a yellow solid. The crude material was used in the next reaction without further purification. $^1$H NMR (400 MHz, DMSO-d$_6$) δ 7.73 (s, 1H), 3.83 (s, 3H).

Step E—Synthesis of Compound Int-20e

To a solution of compound Int-20d (240 g, 757 mmol) and DMF (1.50 L) stirred at 0~5° C., was slowly added NaH (115 g, 2.88 mol, 60% wt.). It was stirred at 0~5° C. for 30 min, and then a solution of (4-methoxyphenyl)methanol (157 g, 1.14 mol) in DMF (1.50 L) was added. The reaction was stirred at 0~5° C. for 30 min, then warmed to 15° C. and stirred for 2 hours. The reaction was quenched by adding 1 L of saturated NH$_4$Cl aqueous solution, and acidified with 4 N HCl aqueous solution until pH=4~5. The resulting mixture was extracted with ethyl acetate. The organic layer was washed with brine, dried over anhydrous Na$_2$SO$_4$, then concentrated under vacuum to give compound Int-20e. Mass Calc'd for C$_{15}$H$_{14}$NBrO$_5$: 367.0, found 389.8 (M+Na)$^+$.

Step F—Synthesis of Compound Int-20f

To a mixture of compound 6 (290 g, 788 mmol) and K$_2$CO$_3$ (272 g, 1970 mmol) in DMF (2.5 L) stirred at 15° C., was slowly added iodomethane (355 g, 2360 mmol). The reaction was stirred at 15° C. for 12 h. The reaction mixture was diluted with 1.5 L of water and extracted with ethyl acetate. The organic layer was washed with brine, dried over anhydrous Na$_2$SO$_4$, then concentrated under vacuum. The residue was purified by silica gel chromatography eluting with petroleum ether:ethyl acetate:dichloromethane=10:1~2:1. The product containing fractions were combined and concentrated under vacuum. The residue was recrystallized from ethyl acetate/petroleum ether. The solid was collected by filtration, washed with petroleum ether, and dried under vacuum to give compound Int-20f. $^1$H NMR (400 MHz, CDCl$_3$): δ 7.35 (d, J=8.8 Hz, 2H), 7.16 (s, 1H), 6.95 (d, J=8.8 Hz, 2H), 5.10 (s, 2H), 3.95 (s, 3H), 3.91 (s, 3H), 3.84 (s, 3H).

Example 21

Preparation of Compound 41

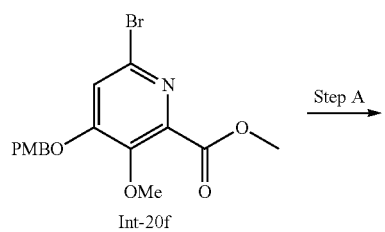

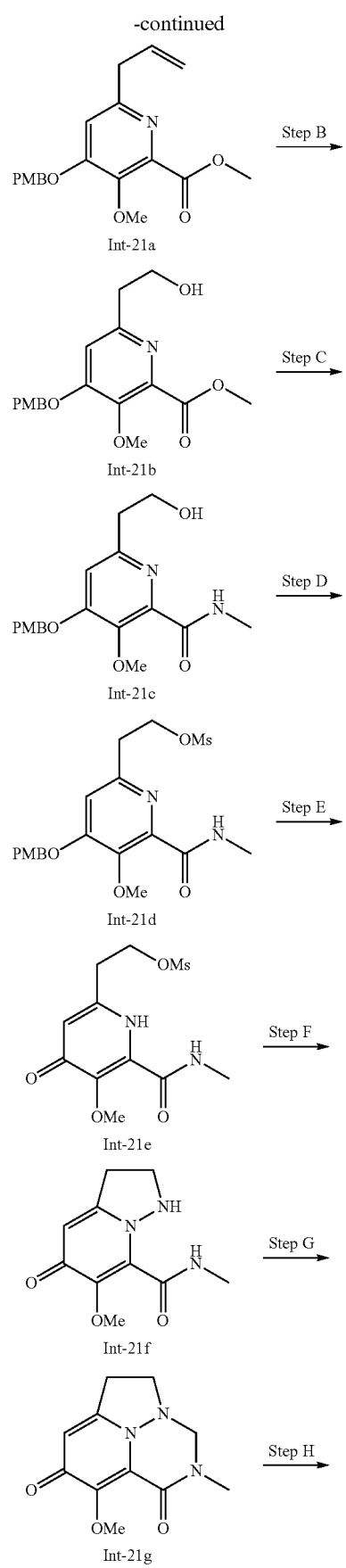

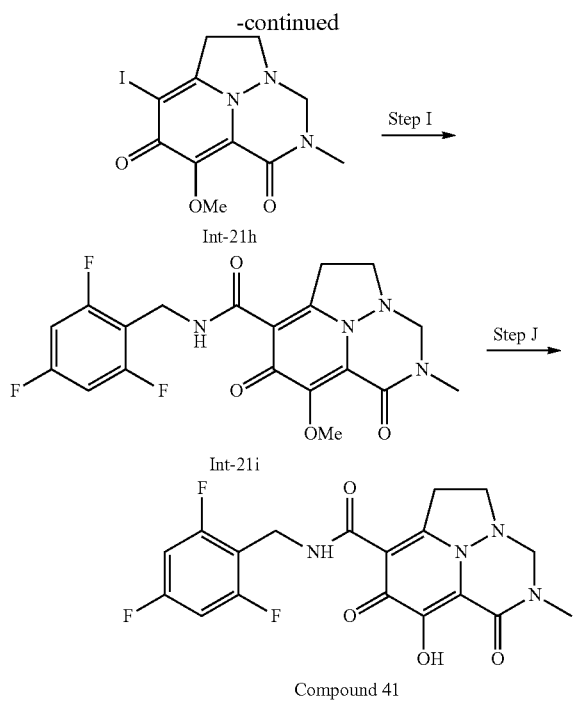

Step A—Synthesis of Compound Int-21a

To a solution of compound Int-20f (10 g, 26.2 mmol) in toluene (100 mL) was added allyltributylstannane (17.33 g, 52.3 mmol) and tetrakis(triphenylphosphine)palladium(0) (1.512 g, 1.308 mmol) at 25° C. The solution was degassed and purged with nitrogen three times, and the resulting mixture was stirred at 110° C. for 16 h under a nitrogen balloon. The reaction mixture was quenched with water (40 mL), and extracted with EtOAc (50 mL×3). The combined organic phase was dried over anhydrous $Na_2SO_4$, filtered and concentrated in vacuo. The residue was purified by silica gel chromatography eluting with petroleum ether/EtOAc=3/1 to give compound Int-21a. $^1$H NMR (400 MHz, $CDCl_3$) δ: 7.33-7.35 (m, 2H), 6.88-6.94 (m, 3H), 5.94-6.04 (m, 1H), 5.13-5.17 (m, 2H), 5.08 (s, 2H), 3.94 (s, 3H), 3.88 (s, 3H), 3.82 (s, 3H), 3.54 (d, J=6.8 Hz, 2H). Mass Calc'd for $C_{19}H_{21}NO_5$: 343.1, found 344.1 (M+H)$^+$.

Step B—Synthesis of Compound Int-21b

A solution of compound Int-21a (6.2 g, 18.06 mmol) in dichloromethane (60 mL) was bubbled with $O_3$ gas at −78° C. for 15 min. Then, sodium borohydride (1.025 g, 27.1 mmol) was added and the mixture was stirred at 0° C. for 1 h. The reaction mixture was quenched with water (40 mL), and extracted with ethyl acetate (40 mL×3). The combined organic phase was dried over anhydrous $Na_2SO_4$, filtered and concentrated in vacuo. The residue was purified by silica gel chromatography eluting with dichloromethane/MeOH=10/1 to give compound Int-21b. Mass Calc'd for $C_{18}H_{21}NO_6$: 347.1, found 348.1 (M+H)$^+$.

Step C—Synthesis of Compound Int-21c

To a solution of compound Int-21b (2.4 g, 6.91 mmol) in THF (35 mL) stirred at 25° C., was added a solution of 2 N methanamine in THF (34.5 mL, 69.1 mmol). The reaction was stirred at 25° C. for 16 h. The resulting mixture was concentrated in vacuo, and the residue was purified by silica gel chromatography eluting with dichloromethane/MeOH=10/1 to give compound Int-21c. $^1$H NMR (400 MHz, $CDCl_3$) δ: 7.41 (s, 1H), 7.34 (d, J=8.4 Hz, 2H), 6.92 (m, 3H), 5.09 (s, 2H), 3.99 (t, J=5.6 Hz, 2H), 3.89 (s, 3H), 3.82 (s, 3H) 2.98 (t, J=5.2 Hz, 2H), 2.93 (t, J=5.6 Hz, 3H). Mass Calc'd for $C_{18}H_{22}N_2O_5$: 346.1, found 347.0 (M+H)$^+$.

Step D—Synthesis of Compound Int-21d

To a stirred solution of compound Int-21c (2.3 g, 6.64 mmol) in dichloromethane (30 mL) stirred at 0° C., was added triethylamine (2.78 mL, 19.92 mmol) and methanesulfonic anhydride (1.735 g, 9.96 mmol). The mixture was stirred at 25° C. for 2 h. It was quenched with water (20 mL), and extracted with EtOAc (30 mL×3). The combined organic phase was dried over anhydrous $Na_2SO_4$, filtered and concentrated in vacuo. The residue was purified by silica gel chromatography eluting with dichloromethane/MeOH=10/1 to compound Int-21d. $^1$H NMR (400 MHz, $CDCl_3$) δ: 7.64 (s, 1H), 7.34 (d, J=8.4 Hz, 2H), 6.92 (m, 3H), 5.10 (s, 2H), 4.65 (t, J=6.0 Hz, 2H), 3.92 (s, 3H), 3.82 (s, 3H) 3.12 (t, J=6.0 Hz, 2H), 2.97 (d, J=5.2 Hz, 3H), 2.89 (s, 3H). Mass Calc'd for $C_{19}H_{24}N_2O_7S$: 424.1, found 424.9 (M+H)$^+$.

Step E—Synthesis of Compound Int-21e

To a solution of compound Int-21d (2.1 g, 4.95 mmol) in MeOH (25 mL) was added Pd/C (0.526 g, 0.495 mmol) at 25° C. The reaction mixture was stirred at 25° C. for 3 h under a balloon of hydrogen. The resulting mixture was filtered and the filtrate was concentrated in vacuo. The residue was purified by by silica gel chromatography eluting with dichloromethane/MeOH=10/1 to give compound Int-21e. $^1$H NMR (400 MHz, $CDCl_3$) δ: 8.31 (s, 1H), 6.40 (s, 1H), 4.49 (t, J=6.0 Hz, 2H), 4.14 (s, 3H), 3.10 (s, 3H), 3.04 (m, 5H). Mass Calc'd for $C_{11}H_{16}N_2O_6S$: 304.1, found 304.9 (M+H)$^+$.

Step F—Synthesis of Compound Int-21f

To a solution of compound Int-21e (300 mg, 0.986 mmol) in MeCN (6 mL) was added cesium carbonate (1285 mg, 3.94 mmol) and O-(2,4-dinitrophenyl)hydroxylamine (393 mg, 1.972 mmol) at 25° C. The reaction was stirred at 25° C. for 3 h. The resulting mixture was filtered, and the filtrate was purified by a preparative-HPLC (Column: Waters XSELECT C18 150 mm*30 mm*5 um, Condition: water (0.1% TFA)-ACN Begin B 0% End B 20% Gradient Time (min) 10, 100% B Hold Time (min) 2, FlowRate (mL/min) 25) to give compound Int-21f. Mass Calc'd for $C_{10}H_{13}N_3O_3$: 223.1, found 224.0 (M+H)$^+$.

Step G—Synthesis of Compound Int-21g

To a solution of compound Int-21f (60 mg, 0.269 mmol) in 1,1-dichloroethane (3 mL) was added dimethoxymethane (614 mg, 8.06 mmol) and methanesulfonic acid (155 mg, 1.613 mmol) at 25° C. The solution was stirred at 120° C. for 4 h under a balloon of nitrogen. The mixture was concentrated in vacuo, and the residue was purified by preparative-HPLC (Column: Waters XSELECT C18 150 mm*30 mm*5 um, Condition: water (0.1% TFA)-ACN Begin B 0% End B 20% Gradient Time (min) 10, 100% B Hold Time (min) 2, FlowRate (mL/min) 25) to give compound Int-21g. Mass Calc'd for $C_{11}H_{13}N_3O_3$: 235.1, found 236.1 (M+H)$^+$.

Step H—Synthesis of Compound Int-21h.

To a solution of compound Int-21g (37 mg, 0.157 mmol) in MeOH (4 mL) was added NIS (70.8 mg, 0.315 mmol) and m-CPBA (27.1 mg, 0.157 mmol) at 25° C. The reaction was stirred at 70° C. for 1 h under a balloon of nitrogen, and then cooled to rt. The mixture was filtered and the filtrate was purified by preparative-HPLC (Column: Waters XSELECT C18 150 mm*30 mm*5 um, Condition: water (0.1% TFA)-ACN Begin B 0% End B 40% Gradient Time (min) 10 100% B Hold Time (min) 2 FlowRate (mL/min) 25) to give compound Int-21h as a yellow oil. $^1$H NMR (400 MHz, CDCl$_3$) δ: 4.59 (s, 2H), 3.92 (s, 3H), 3.54 (m, 2H), 3.46 (m, 2H), 3.15 (s, 3H). Mass Calc'd for C$_{11}$H$_{12}$IN$_3$O$_3$: 361.0, found 362.0 (M+H)$^+$.

Step I—Synthesis of Compound Int-21i

To a solution of compound Int-21h (28 mg, 0.078 mmol) in DMSO (3 mL) was added (2,4,6-trifluorophenyl)methanamine (125 mg, 0.775 mmol), DIPEA (0.135 mL, 0.775 mmol) and Pd(PPh$_3$)$_4$ (17.92 mg, 0.016 mmol). The mixture was degassed and purged with CO three times. The resulting mixture was stirred at 90° C. under a balloon of carbon monoxide for 2 h. It was quenched with water (10 mL), and extracted with EtOAc (20 mL×3). The combined organic layer was dried over anhydrous Na$_2$SO$_4$, filtered and concentrated in vacuo. The residue was purified by silica gel chromatography eluting with dichloromethane/MeOH=10/1 to give compound Int-21i. $^1$H NMR (400 MHz, CDCl$_3$) δ: 10.82 (s, 1H), 6.59 (m, 2H), 4.54 (m, 2H), 4.34 (s, 2H), 4.00 (s, 3H), 3.97 (m, 2H), 3.32 (m, 2H), 3.12 (s, 3H). Mass Calc'd for C$_{19}$H$_{17}$F$_3$N$_4$O$_4$: 422.1, found 422.9 (M+H)$^+$.

Step J—Synthesis of Compound 41

To a solution of compound Int-21i (18 mg, 0.043 mmol) in ACN (2 mL) stirred at 25° C., was added magnesium bromide (23.54 mg, 0.128 mmol). The mixture was stirred at 25° C. for 1 h under a balloon of nitrogen. The reaction mixture was diluted with MeOH (1 mL), and the resulting solution was purified by preparative-HPLC (Column: Boston Green ODS 150 mm*30 mm, 5 um, Condition: water (0.1% TFA)-ACN Begin B 30%, End B 60%, Gradient Time (min) 10, 100% B Hold Time (min) 2, FlowRate (mL/min) 25) to give compound 41 as a white solid. $^1$H NMR (400 MHz, CDCl$_3$) δ: 10.75 (s, 1H), 6.65 (t, J=8.0 Hz, 2H), 4.62 (d, J=5.6 Hz, 2H), 4.46 (s, 2H), 3.95 (m, 2H), 3.41 (m, 2H), 3.18 (s, 3H). Mass Calc'd for C$_{18}$H$_{15}$F$_3$N$_4$O$_4$: 408.1, found 408.9 (M+H)$^+$.

Example 22

Preparation of Compound 42 and Compound 43

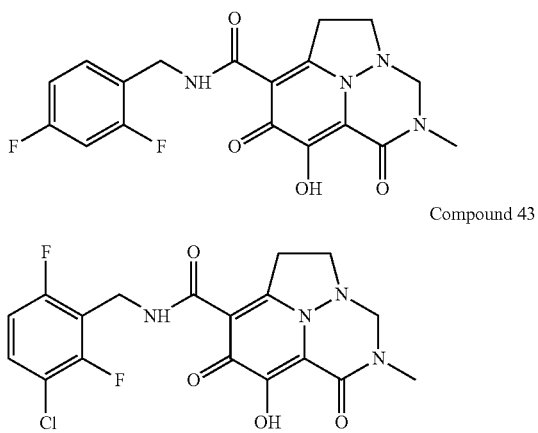

Compound 42

Compound 43

Compounds 42 and 43 were prepared using the methods described in Example 21, replacing (2,4,6-trifluorophenyl) methanamine with appropriate benzylamines in step I.

Compound 42: $^1$H NMR (400 MHz, CDCl$_3$) δ: 10.80 (s, 1H), 7.35 (m, 1H), 6.82 (m, 2H), 4.60 (d, J=4.8 Hz, 2H), 4.48 (s, 2H), 3.94 (m, 2H), 3.42 (m, 2H), 3.19 (s, 3H). Mass Calc'd for C$_{18}$H$_{16}$F$_2$N$_4$O$_4$: 390.1, found 391.0 (M+H)$^+$.

Compound 43: $^1$H NMR (400 MHz, CDCl$_3$) δ: 10.80 (s, 1H), 7.29 (m, 1H), 6.85 (m, 1H), 4.70 (d, J=5.6 Hz, 2H), 4.47 (s, 2H), 3.95 (m, 2H), 3.42 (m, 2H), 3.19 (s, 3H). Calc'd for C$_{18}$H$_{15}$ClF$_2$N$_4$O$_4$: 424.1, found 425.0 (M+H)$^+$.

Assay for Inhibition of HIV Replication

This assay may be useful for assessing the ability of a compound of the present invention to inhibit HIV replication. The assay is a kinetic assay that employs a reporter cell line (MT4-gag-GFP) to quantify the number of new cells infected in each round of replication.

MT4-GFP cells (250,000 cells/ml) are bulk-infected with HIV-1 (NL4-3 strain) at low multiplicity of infection (MOI) in RPMI+10% FBS for 24 hours. Cells are then washed once in RPMI+10% FBS and resuspended in RPMI+0% normal human serum (NHS). Test compounds are serial-diluted in DMSO on ECHO. The infected MT4-GFP cells are added to a 384-well poly-D-lysine coated black plate with clear bottom in which the diluted test compounds are placed. The cells are seeded at 8,000 cells per well and the final DMSO concentration is adjusted to 0.4%. The infected cells (Green GFP cells) are then quantified at both 24 and 48 hours post incubation using Acumen eX3. Viral reproductive ratio ($R_0$) is determined using the number of infected cells at 48 hours divided by the number of infected cells at 24 hours. Percent viral growth inhibition is calculated by [1-(R—R$_{tripledrug}$)/ (R$_{DMSO}$—R$_{tripledrug}$)]*100. Compound potency IP or IC$_{50}$ may be determined using a 4-parameter dose response curve analysis.

Illustrative compounds of the present invention were tested using this assay protocol and results are presented in the table below.

| Compound No. | VIKING IP$_{50}$ (nM) with 0% NHS |
|---|---|
| 2 | 195 |
| 3 | 19.8 |
| 4 | 2.0 |
| 5 | 1.7 |
| 6 | 74.6 |
| 7 | 13.3 |
| 8 | 4.7 |
| 9 | 1.4 |
| 10 | 1.4 |
| 11 | 1.1 |
| 12 | 2.3 |
| 13 | 1.0 |
| 14 | 4.6 |
| 15 | 1.9 |
| 16 | 1.5 |
| 17 | 1.4 |
| 18 | 0.4 |
| 19 | 2.4 |
| 20 | 1.2 |
| 21 | 1.0 |
| 22 | 2.1 |
| 23 | 4.1 |
| 24 | 1.5 |
| 25 | 0.9 |
| 26 | 1.5 |
| 27 | 1.2 |
| 28 | 4.0 |
| 29 | 9.9 |
| 30 | 1.5 |
| 31 | 0.5 |
| 32 | 1.2 |
| 33 | 0.8 |
| 34 | 11.5 |
| 35 | 2.2 |
| 36 | 11.4 |

-continued

| Compound No. | VIKING IP$_{50}$ (nM) with 0% NHS |
|---|---|
| 37 | 8.5 |
| 38 | 2.6 |
| 39 | 2.4 |
| 40 | 3.8 |
| 41 | 2.9 |
| 42 | 1.6 |
| 43 | 1.8 |

Treatment or Prevention of HIV Infection

The Tricyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Tricyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Tricyclic Heterocycle Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Tricyclic Heterocycle Compounds are also useful in the preparation and execution of screening assays for antiviral compounds. For example the Tricyclic Heterocycle Compounds may be useful for identifying resistant HIV cell lines harboring mutations, which are excellent screening tools for more powerful antiviral compounds. Furthermore, the Tricyclic Heterocycle Compounds may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Tricyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Tricyclic Heterocycle Compound (which may include two or more different Tricyclic Heterocycle Compounds), or a pharmaceutically acceptable salt or prodrug thereof, and (ii) at least one additional therapeutic agent that is other than a Tricyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Tricyclic Heterocycle Compound is administered during a time when the additional therapeutic agent(s) exert their prophylactic or therapeutic effect, or vice versa.

In another embodiment, at least one Tricyclic Heterocycle Compound and the additional therapeutic agent(s) are administered in doses commonly employed when such agents are used as monotherapy for treating a viral infection.

In another embodiment, at least one Tricyclic Heterocycle Compound and the additional therapeutic agent(s) are administered in doses lower than the doses commonly employed when such agents are used as monotherapy for treating a viral infection.

In still another embodiment, at least one Tricyclic Heterocycle Compound and the additional therapeutic agent(s) act synergistically and are administered in doses lower than the doses commonly employed when such agents are used as monotherapy for treating a viral infection.

In one embodiment, at least one Tricyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.
In another embodiment, the viral infection is AIDS.

The at least one Tricyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tricyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| Doravirine | nnRTI |
| efavirenz, EFV, Sustiva ®, Stocrin ® | nnRTI |
| efavirenz + emtricitabine + tenofovir DF, Atripla ® | nnRTI + nRTI |
| EfdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
PI = protease inhibitor;
nRTI = nucleoside reverse transcriptase inhibitor;
II = integrase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with darunavir.

In another embodiment, the compound of formula (I) is used in combination with emtricitabine and tenofovir.

In still another embodiment, the compound of formula (I) is used in combination atazanavir.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Tricyclic Heterocycle Compounds may be administered as a component of a composition that comprises a pharmaceutically acceptable carrier or vehicle. The present invention provides pharmaceutical compositions comprising an effective amount of at least one Tricyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tricyclic Heterocycle Compounds are administered orally.

In another embodiment, the one or more Tricyclic Heterocycle Compounds are administered intravenously.

In one embodiment, a pharmaceutical preparation comprising at least one Tricyclic Heterocycle Compound is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Tricyclic Heterocycle Compound(s) by weight or volume. In various embodiments, the present compositions can contain, in one embodiment, from about 1% to about 70% or from about 5% to about 60% of the Tricyclic Heterocycle Compound(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Tricyclic Heterocycle Compounds may be administered at varying frequencies. In one embodiment, a unit dosage of a Tricyclic Heterocycle Compound may be administered once daily. In another embodiment, a unit dosage of a Tricyclic Heterocycle Compound may be administered twice weekly. In another embodiment, a unit dosage of a Tricyclic Heterocycle Compound may be administered once weekly. In still another embodiment, a unit dosage of a Tricyclic Heterocycle Compound may be administered once biweekly. In another embodiment, a unit dosage of a Tricyclic Heterocycle Compound may be administered once monthly. In yet another embodiment, a unit dosage of a Tricyclic Heterocycle Compound may be administered once bimonthly. In another embodiment, a unit dosage of a Tricyclic Heterocycle Compound may be administered once every 3 months. In a further embodiment, a unit dosage of a Tricyclic Heterocycle Compound may be administered once every 6 months. In another embodiment, a unit dosage of a Tricyclic Heterocycle Compound may be administered once yearly.

The amount and frequency of administration of the Tricyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Tricyclic Heterocycle Compound, or a pharmaceutically acceptable salt or prodrug of said compound and a pharmaceutically acceptable carrier, vehicle or diluent.

In another aspect the present invention provides a kit comprising an amount of at least one Tricyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Tricyclic Heterocycle Compounds and the one or more additional therapeutic agents are provided in the same container. In one embodiment, the one or more Tricyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

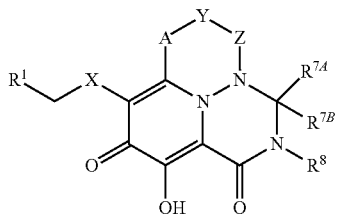

or a pharmaceutically acceptable salt thereof,
wherein:
A is —CH($R^2$)—;
X is 5 or 6-membered monocyclic heteroaryl or —N($R^5$)(C=O);
Y is selected from —O—, —N($R^5$)— or —CH($R^3$)—, or -A-Y— is —C($R^2$)=CH—;
Z is —CH($R^4$)— or a bond, such that: (i) when Y is —O— or —N($R^5$)—, then Z is a bond, (b) when Y is —CH($R^3$)—, then Z is a bond or —CH($R^4$)—, and (iii) when -A-Y— is —C($R^2$)=CH—, then Z is a bond;

$R^1$ is a phenyl group which is optionally substituted with from 1 to 3 groups, each independently selected from $C_1$-$C_6$ alkyl, halo, —O—($C_1$-$C_6$ alkyl), $C_1$-$C_6$ haloalkyl, —O—($C_1$-$C_6$ haloalkyl), —CN, —NO$_2$, —N($R^4$)$_2$, —(C=O)O$R^6$, —(C=O)N($R^4$)$_2$ and —NH(C=O)$R^6$;

$R^2$ is selected from H, $C_1$-$C_6$ alkyl, —O—($C_1$-$C_6$ alkyl) and —N($R^4$)$_2$;

$R^3$ is selected from H, $C_1$-$C_6$ alkyl and —O—($C_1$-$C_6$ alkyl);

each occurrence of $R^4$ is independently selected from H, $C_1$-$C_6$ alkyl and —O—($C_1$-$C_6$ alkyl);

each occurrence of $R^5$ is independently H or $C_1$-$C_6$ alkyl;

each occurrence of $R^6$ is independently selected from H, $C_1$-$C_6$ alkyl and $C_3$-$C_7$ cycloalkyl;

$R^{7A}$ is H;

$R^{7B}$ is H, or $R^{7A}$ and $R^{7B}$, together with the common carbon atom to which they are each attached, join to form a spirocyclic $C_3$-$C_7$ cycloalkyl group or a spirocyclic 4- to 7-membered monocyclic heterocycloalkyl group; and $R^8$ is selected from $C_1$-$C_6$ alkyl, —($C_1$-$C_6$ alkylene)-O—($C_1$-$C_6$ alkyl), $C_3$-$C_7$ cycloalkyl and —($C_1$-$C_6$ alkylene)-$C_3$-$C_7$ cycloalkyl.

2. The compound of claim 1, or a pharmaceutically acceptable salt thereof,
wherein:
the group -A-Y—Z— is selected from —CH($R^2$)CH$_2$—, —CH($R^2$)—CH($R^3$)—CH($R^4$)— and —C($R^2$)=CH—;
X is diazolyl or —N($R^5$)(C=O);
$R^1$ is a phenyl group which is optionally substituted with from 1 to 3 groups, each independently selected from Cl and F;
$R^2$ is H or —O—($C_1$-$C_6$ alkyl);
each occurrence of $R^4$ is independently selected from H and $C_1$-$C_6$ alkyl;
each occurrence of $R^5$ is independently H or $C_1$-$C_6$ alkyl;
$R^{7A}$ is H;
$R^{7B}$ is H, or $R^{7A}$ and $R^{7B}$, together with the common carbon atom to which they are each attached, join to form a spirocyclic 4- to 7-membered monocyclic heterocycloalkyl group; and
$R^8$ is selected from $C_1$-$C_6$ alkyl, —($C_1$-$C_6$ alkylene)-O—($C_1$-$C_6$ alkyl) and —($C_1$-$C_6$ alkylene)-$C_3$-$C_7$ cycloalkyl.

3. The compound of claim 1, wherein the -A-Y—Z— group is —CH($R^2$)—CH$_2$—, or a pharmaceutically acceptable salt thereof.

4. The compound of claim 1, wherein the -A-Y—Z— group is —CH($R^2$)—CH($R^3$)—CH($R^4$)—, or a pharmaceutically acceptable salt thereof.

5. The compound of claim 1, wherein the -A-Y—Z— group is —C($R^2$)=CH—, or a pharmaceutically acceptable salt thereof.

6. The compound of claim 1, wherein X is —NH(C=O), or a pharmaceutically acceptable salt thereof.

7. The compound of claim 1, wherein X is 5-membered heteroaryl, or a pharmaceutically acceptable salt thereof.

8. The compound of claim 1, wherein $R^1$ is phenyl, which is substituted with from 1-3 groups, each independently selected from F and Cl, or a pharmaceutically acceptable salt thereof.

9. The compound of claim 1, wherein $R^1$ is selected from:

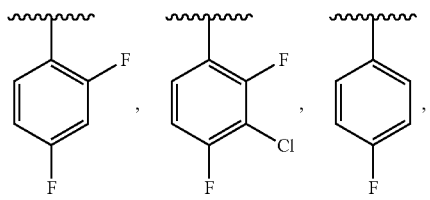

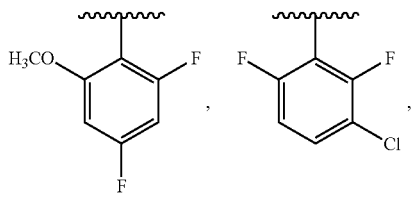

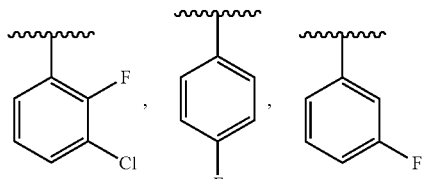

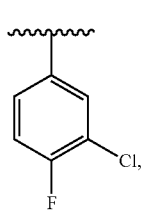

or a pharmaceutically acceptable salt thereof.

10. The compound of claim 1, wherein $R^{7A}$ and $R^{7B}$ are each H, or a pharmaceutically acceptable salt thereof.

11. The compound of claim 1, wherein $R^{7A}$ and $R^{7B}$, together with the common carbon atoms to which they are attached, join to form a 4 to 7-membered heterocycloalkyl group, or a pharmaceutically acceptable salt thereof.

12. The compound of claim 1, wherein $R^8$ is methyl, ethyl, isopropyl, —CH$_2$CH$_2$OCH$_3$ and —CH$_2$-cyclopropyl, or a pharmaceutically acceptable salt thereof.

13. A compound selected from:

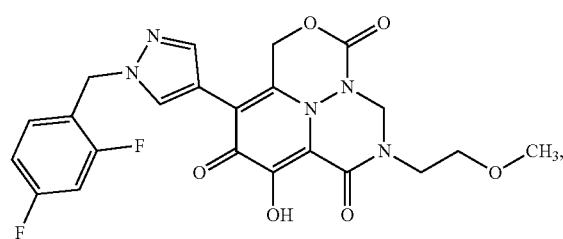

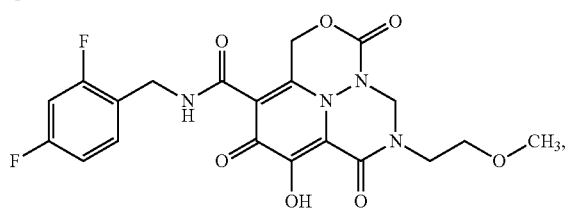

-continued

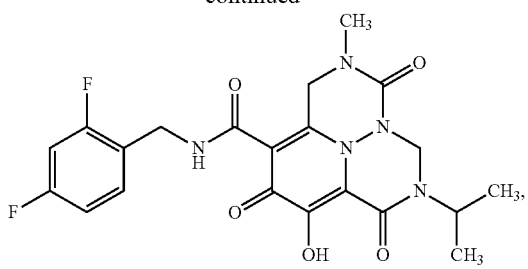

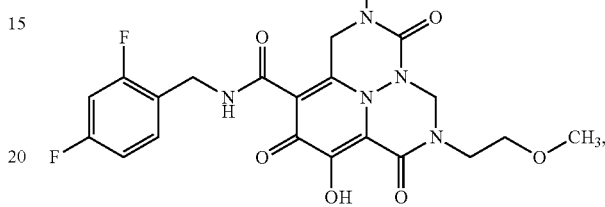

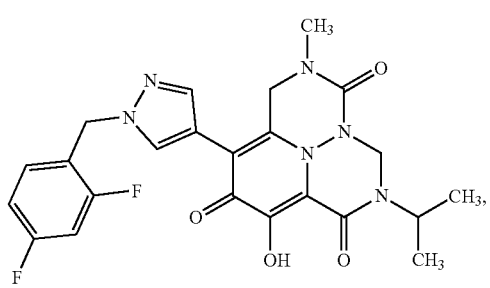

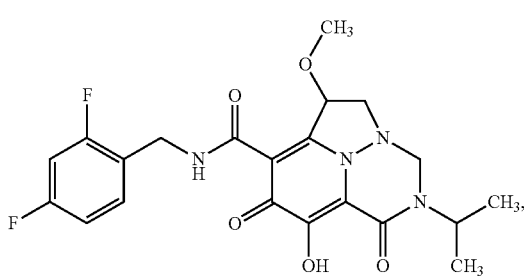

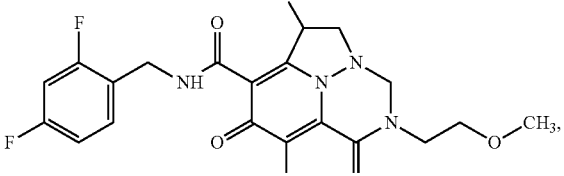

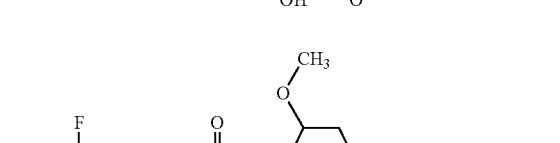

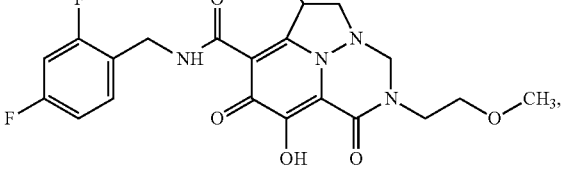

107
-continued
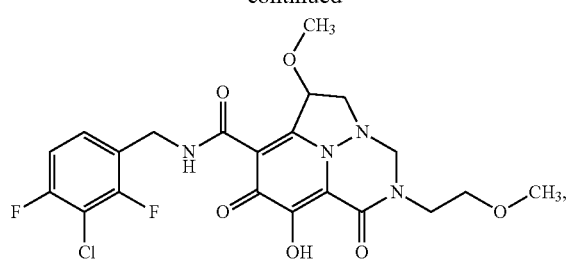
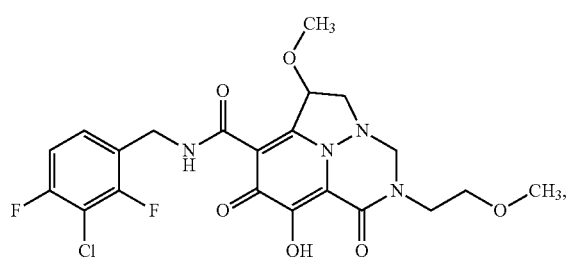
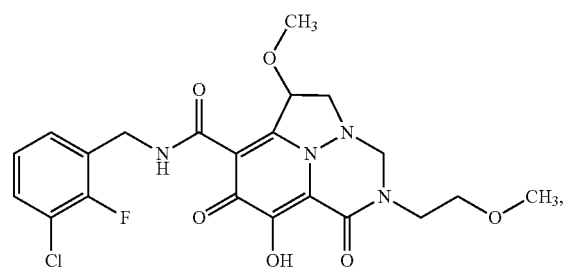
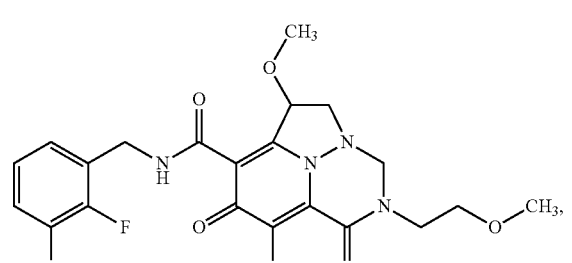
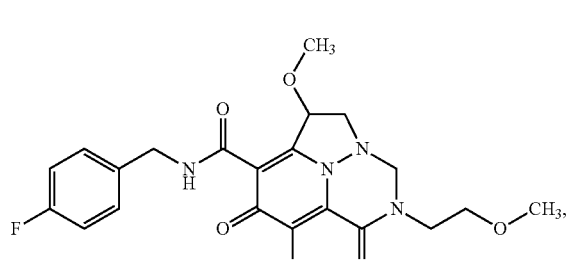
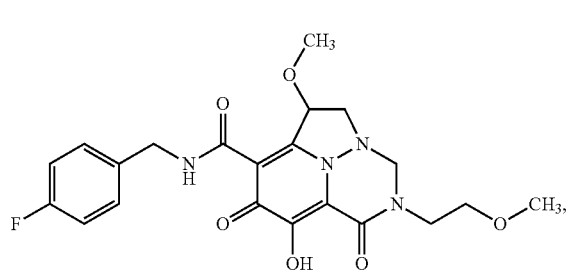
108
-continued
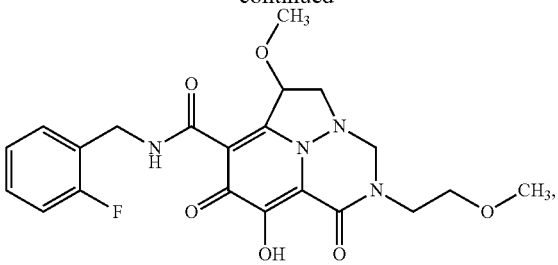
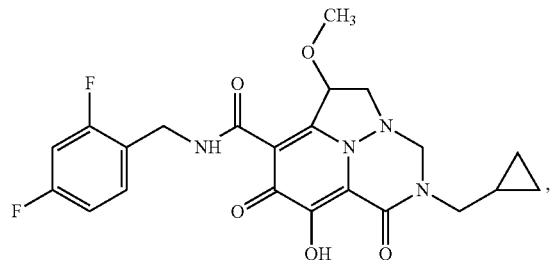
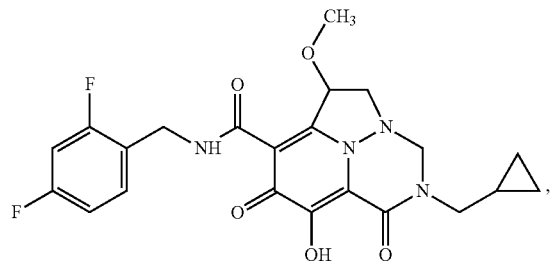
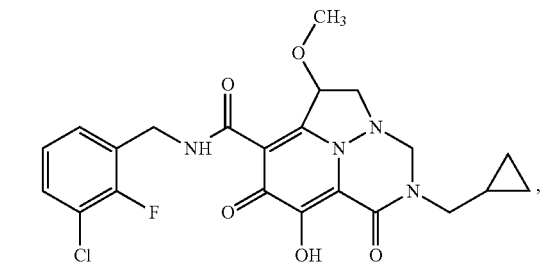
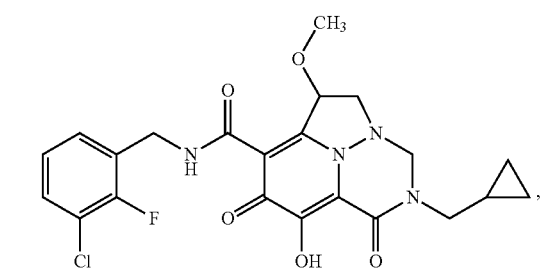
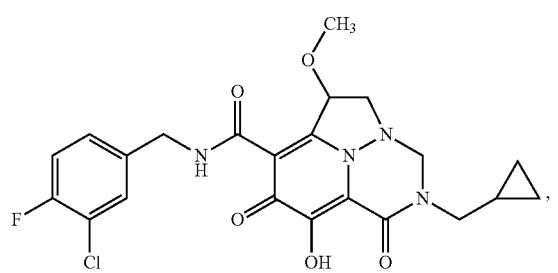

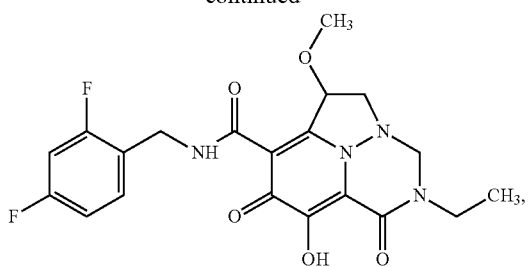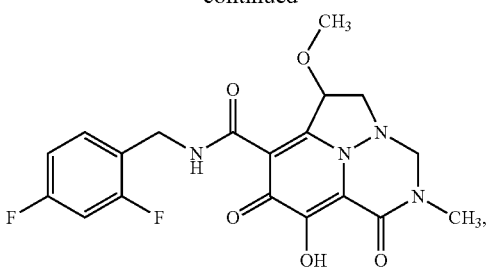

111

-continued

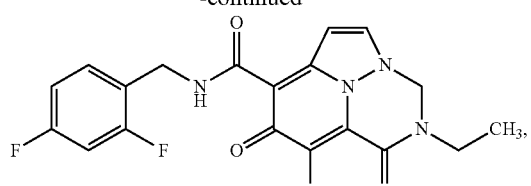

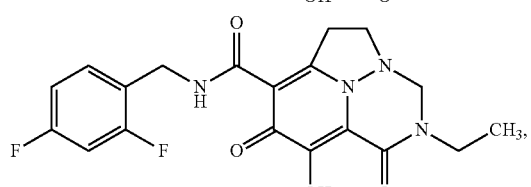

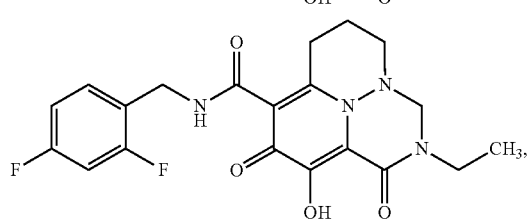

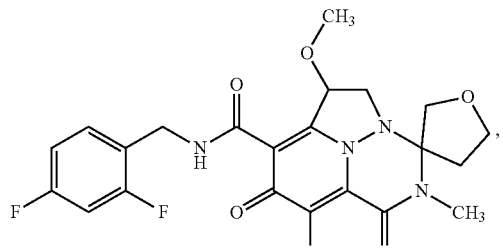

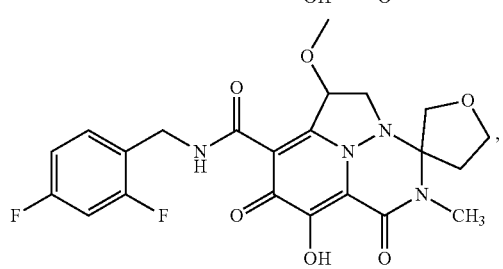

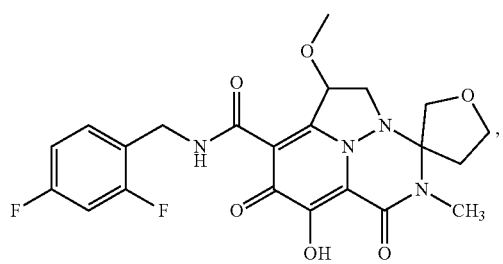

112

-continued

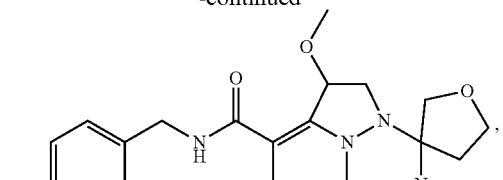

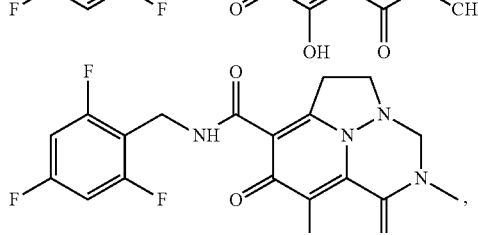

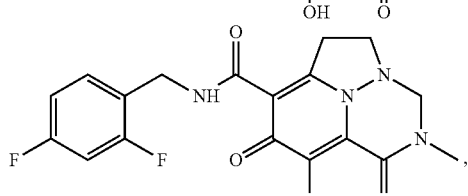

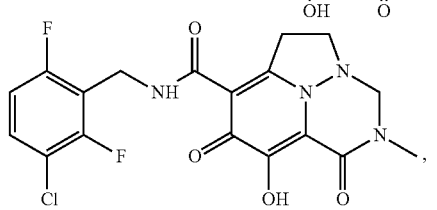

or a pharmaceutically acceptable salt thereof.

14. A pharmaceutical composition comprising an effective amount of a compound according to claim 1, or a pharmaceutically acceptable salt thereof, and a pharmaceutically acceptable carrier.

15. A method for the treatment of infection by HIV or for the treatment or delay in the onset or progression of AIDS in a subject in need thereof, which comprises administering to the subject an effective amount of the compound according to claim 1, or a pharmaceutically acceptable salt thereof.

16. The pharmaceutical composition of claim 14, further comprising one or more additional therapeutic agents selected from, lamivudine, abacavir, ritonavir, darunavir, atazanavir, emtricitabine, tenofovir, rilpivirine and lopinavir.

17. The method of claim 15, further comprising administering to the subject one or more additional therapeutic agents selected from, abacavir, lamivudine, ritonavir and lopinavir, wherein the amounts administered of the compound of claim 1 and the one or more additional therapeutic agents, are together effective to treat infection by HIV or to treat or delay the onset or progression of AIDS.

* * * * *